(12) United States Patent
Neev et al.

(10) Patent No.: US 12,146,140 B2
(45) Date of Patent: *Nov. 19, 2024

(54) T-LYMPHOCYTE BINDING APTAMERS

(71) Applicant: Aummune Ltd., Tel Aviv-Jaffa (IL)

(72) Inventors: Guy Neev, Bnei Dror (IL); Irit Carmi-Levy, Tel Aviv (IL); Erez Lavi, Yavne (IL); Neta Zilony-Hanin, Azor (IL); Zohar Pode, Tel Aviv (IL); Neria Reiss, Dolev (IL); Ohad Glaich, Givatayim (IL); Ronit Farhi, Pardes hanna (IL)

(73) Assignee: Aummune Ltd., Tel Aviv-Jaffa (IL)

( * ) Notice: Subject to any disclaimer, the term of this patent is extended or adjusted under 35 U.S.C. 154(b) by 26 days.

This patent is subject to a terminal disclaimer.

(21) Appl. No.: 17/542,046

(22) Filed: Dec. 3, 2021

(65) Prior Publication Data

US 2022/0186223 A1 Jun. 16, 2022

Related U.S. Application Data

(60) Provisional application No. 63/257,402, filed on Oct. 19, 2021, provisional application No. 63/121,080, filed on Dec. 3, 2020.

(51) Int. Cl.
*C12N 15/115* (2010.01)
*A61P 35/00* (2006.01)

(52) U.S. Cl.
CPC ............ *C12N 15/115* (2013.01); *A61P 35/00* (2018.01); *C12N 2310/16* (2013.01); *C12N 2310/3513* (2013.01); *C12N 2310/3519* (2013.01); *C12N 2320/30* (2013.01)

(58) Field of Classification Search
CPC .............. C12N 15/115; C12N 2310/16; C12N 2310/3513; C12N 2310/3519; C12N 2320/30; C12N 2310/17; C12N 2310/315; C12N 2310/317; C12N 2310/51; C12N 2320/31; A61P 35/00
See application file for complete search history.

(56) References Cited

U.S. PATENT DOCUMENTS

| 2019/0101529 A1* | 4/2019 | Wang ................. G01N 33/6896 |
| 2022/0186223 A1 | 6/2022 | Neev et al. |

FOREIGN PATENT DOCUMENTS

| WO | WO-2014016368 A1 * | 1/2014 | ........... C12N 15/115 |
| WO | WO-2017143150 A1 * | 8/2017 | ........... C12N 15/115 |
| WO | WO-2018/017827 A1 | 1/2018 | |
| WO | WO-2019/035763 A1 | 2/2019 | |
| WO | WO-2020/065404 A2 | 4/2020 | |
| WO | WO-2021/234453 A1 | 11/2021 | |
| WO | WO-2021/234456 A2 | 11/2021 | |
| WO | WO-2022/118077 A2 | 6/2022 | |

OTHER PUBLICATIONS

U.S. Appl. No. 17/926,071, filed May 2023.*

(Continued)

*Primary Examiner* — Kimberly Chong
*Assistant Examiner* — Ruth Sophia Arieti
(74) *Attorney, Agent, or Firm* — Foley Hoag LLP; Brendan T. Jones; Mi Cai

(57) ABSTRACT

Provided herein are aptamers that target T-lymphocytes and methods of use thereof.

17 Claims, 28 Drawing Sheets

Specification includes a Sequence Listing.

(56) References Cited

OTHER PUBLICATIONS

U.S. Appl. No. 17/926,067, filed May 2023.*
Huda and Pan. 2017. Tau in Tauopathies That Leads to Cognitive Disorders and in Cancer. Chapter 5 in Cognitive Disorders (Year: 2017).*
Lee et al. 2019. Cytohesin-2 Is Upregulated in Malignant Melanoma and Contributes to Tumor Growth. Annal. Dermatol. 31[1]:93-96 (Year: 2019).*
AlzForum Mar. 7, 2020. Tau Receptor Identified on Cell Surface. Available online at https://www.alzforum.org/news/conference-coverage/tau-receptor-identified-cell-surface (Year: 2020).*
Zhou and Rossi. 2016. Aptamers as targeted therapeutics: current potential and challenges. Drug Discov. 16:181-202 (Year: 2016).*
Leko and Rosenberg. 2020. Identifying and Targeting Human Tumor Antigens for T Cell-Based Immunotherapy of Solid Tumors. Cancer Cell 38:454-472 (Year: 2020).*
Minati et al. 2020. A Roadmap Toward the Definition of Actionable Tumor-Specific Antigens. Frontiers Immunol. 11: Article 583287 (Year: 2020).*
NHS. Cancer. 2022. Available online at nhs.uk/conditions/cancer/symptoms/ Accessed on Jan. 4, 2024 (Year: 2022).*
Stanford. Cancer Types. 2024. Available online at https://stanfordhealthcare.org/medical-conditions/cancer/cancer-types.html Accessed on Jan. 4, 2024 (Year: 2024).*
Invitation to Pay Additional Fees for International Application No. PCT/IB2021/000345 notification mailed Sep. 22, 2021.
Invitation to Pay Additional Fees for International Application No. PCT/IB2021/000849 dated Jun. 22, 2022.
Kacherovsky et al., "Traceless aptamer-mediated isolation of CD8+ T cells for chimeric antigen receptor T-cell therapy," Nature Biomedical Engineering, 3(10): 783-795 (2019).
Khedri et al., "Cancer immunotherapy via nucleic acid aptamers," International Immunopharmacology, 29(2): 926-936 (2015).
McNamara II et al., "Multivalent 4-1BB binding aptamers costimulate CD8+ T cells and inhibit tumor growth in mice," The Journal of Clinical Investigation, 118(1): 376-386 (2008).
Vandghanooni et al., "Bispecific therapeutic aptamers for targeted therapy of cancer: a review on cellular perspective," Journal of Molecular Medicine, 96(9): 885-902 (2018).
Dobranowski et al., "Perspectives on the discovery of NOTCH2-specific inhibitors," Chemical Biology and Drug Design 91(3): pp. 691-706 (2017).
International Preliminary Report on Patentability for Application No. PCT/IB2021/000345 dated Dec. 1, 2022.
International Search Report and Written Opinion for Application No. PCT/IB2021/000849 dated Aug. 12, 2022.

\* cited by examiner

A.

B.

```
                            SEQUENCE LISTING

<160> NUMBER OF SEQ ID NOS: 74

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atcgtataag ggctgcttag gattgcgata atacggtcaa                              40

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
catttcatag ggctgcttag gattgcgaag gtaatgccag                              40

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cccttacccc ttttaggtct gcttaggatt gcgaaaaaag                              40

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ttgtaaggac tgcttaggat tgcgaaaaca atattcgtat                              40

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
```
cttttaggtc tgcttaggat tgcgaaaaaa g                                    31

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tccatgggtc tgctctagga ttgcgttcat ggtctccccg                           40

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aattacaacc ttggattgca aagggctgct gtgttgttta                           40

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
atcggagctg ttccttgata ccgattcaaa aagttcgtac                           40

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aatttgtagg gactgctcag gattgcggat acaaattaat                           40

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
agacattggg gactgctcgg gattgcgaat ctatgtctcc                           40

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11 cccttttttta actaggtctg cttaggattg cgaatgttaa                           40

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
acctcaaaag cgcgggctgc tcaaaggatt gcgtagcttt                            40

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gggggttaag ggctgcttag gattgcgata atacggtcaa                           40

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aacatataac tgctcaataa tatagataaa atactcacaa                           40

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ctctacctga ctgtaacctc tcgctccccc ccattcgcgc                           40

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ttgtccctct acgccgccct ttactaccac tcctgcgatt                           40

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tccagcacac cgaccgcccc tctacattac cccctggact                           40

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 18
cccctccatt cccccgcctc gtccacccta ctccttagtc                           40

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 19
catcgacgcc cacacaccac ttcccgttcc cctgcatcat                           40

<210> SEQ ID NO 20
<211> LENGTH: 63
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 20
tcgtcgtcgc ggttcgcgtc cgtatcgtat aagggctgct taggattgcg ataatacggt    60
caa                                                                  63

<210> SEQ ID NO 21
<211> LENGTH: 64
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<221> NAME/KEY: modified_base
<222> LOCATION: (64)..(64)
<223> OTHER INFORMATION: Inverted deoxythymidine

<400> SEQUENCE: 21
tcgtcgtcgc ggttcgcgtc cgtatcgtat aagggctgct taggattgcg ataatacggt    60
caat                                                                 64

<210> SEQ ID NO 22
<211> LENGTH: 74
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<221> NAME/KEY: modified_base
<222> LOCATION: (74)..(74)
<223> OTHER INFORMATION: Inverted deoxythymidine

<400> SEQUENCE: 22
cggacgcgaa ccgcgacgac gatgattgat ctattttcca tatcgcgttg agtgtaaagc    60
cacgaagggt tatt                                                      74

<210> SEQ ID NO 23
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(60)
<223> OTHER INFORMATION: a, c, t, or g
<220> FEATURE:
<223> OTHER INFORMATION: See specification as filed for detailed
      description of substitutions and preferred embodiments

<400> SEQUENCE: 23
tcactatcgg tccagacgta nnnnnnnnnn nnnnnnnnnn nnnnnnnnnn nnnnnnnnnn    60
tattgcgccg aggttcttac                                                80

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcactatcgg tccagacgta                                                20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tcactatcgg tccagacgta                                                20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gtaagaacct cggcgcaata                                                20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tacgtctgga ccgatagtga                                                20

<210> SEQ ID NO 28
<211> LENGTH: 50
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 28
tccttgtcag cactttcaga gcactttccc gtagaactta agggacatgc        50

<210> SEQ ID NO 29
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29
gattgatcta ttttccatat cgcgttgagt gtaaagccac gaagggttat        50

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
attggagttt tccaatcaga aaggattcgg tcagctgcac        40

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31
tggaaacagc tgcaactttt ctgggacgtg aatgcctcgc        40

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32
actcaaaaat taggcaggtg taagtataac tcgtgcctgc        40

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 33
gcaggcggaa aatgtcaggg cacgttggtc acgtattttt        40

<210> SEQ ID NO 34
<211> LENGTH: 40
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 34
agcaatcata tggctgtgct catttaataa gcaagctggg                             40

<210> SEQ ID NO 35
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cggacgcgaa cgccgacgac gattccttgt cagcactttc agagcacttt cccgtagaac       60
ttaagggaca tgc                                                          73

<210> SEQ ID NO 36
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cggacgcgaa ccgcgacgac gatgattgat ctattttcca tatcgcgttg agtgtaaagc       60
cacgaagggt tat                                                          73

<210> SEQ ID NO 37
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cggacgcgaa ccgcgacgac gatgattgat ctattttcca tatcgcgttg agtgtaaagc       60
cacgaagggt tat                                                          73

<210> SEQ ID NO 38
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cggacgcgaa ccgcgacgac gatgattgat ctattttcca tatcgcgttg agtgtaaagc       60
cacgaagggt tat                                                          73

<210> SEQ ID NO 39
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
```
cggacgcgaa ccgcgacgac gatgattgat ctattttcca tatcgcgttg agtgtaaagc    60
cacgaagggt tat                                                       73

<210> SEQ ID NO 40
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cggacgcgaa ccgcgacgac gatattggag ttttccaatc agaaaggatt cggtcagctg    60
cac                                                                  63

<210> SEQ ID NO 41
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cggacgcgaa ccgcgacgac gattggaaac agctgcaact tttctgggac gtgaatgcct    60
cgc                                                                  63

<210> SEQ ID NO 42
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cggacgcgaa ccgcgacgac gatactcaaa aattaggcag gtgtaagtat aactcgtgcc    60
tgc                                                                  63

<210> SEQ ID NO 43
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cggacgcgaa ccgcgacgac gatgcaggcg gaaaatgtca gggcacgttg gtcacgtatt    60
ttt                                                                  63

<210> SEQ ID NO 44
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cggacgcgaa ccgcgacgac gatagcaatc atatggctgt gctcatttaa taagcaagct    60
ggg                                                                  63

<210> SEQ ID NO 45
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
atttgtataa tgtctgatta agttccttgt cagcactttc agagcacttt cccgtagaac    60
ttaagggaca tgc                                                       73

<210> SEQ ID NO 46
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
atttgtataa tgtctgatta agtgattgat ctattttcca tatcgcgttg agtgtaaagc    60
cacgaagggt tat                                                       73

<210> SEQ ID NO 47
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
atttgtataa tgtctgatta agtattggag ttttccaatc agaaaggatt cggtcagctg    60
cac                                                                  63

<210> SEQ ID NO 48
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
atttgtataa tgtctgatta agttggaaac agctgcaact tttctgggac gtgaatgcct    60
cgc                                                                  63

<210> SEQ ID NO 49
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
atttgtataa tgtctgatta agtactcaaa aattaggcag gtgtaagtat aactcgtgcc    60
tgc                                                                  63

<210> SEQ ID NO 50
<211> LENGTH: 69
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 50
cgttataatt gttaattctt ccttgtcagc actttcagag cactttcccg tagaacttaa    60
gggacatgc                                                            69

<210> SEQ ID NO 51
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
cgttataatt gttaattctg attgatctat tttccatatc gcgttgagtg taaagccacg    60
aagggttat                                                            69

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tcgtcgtcgc ggttcgcgtc cg                                             22

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
cggacgcgaa cgccgacgac ga                                             22

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
cgtcgtcggt cgtcgtcgct cg                                             22

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
cgagcgacga cgaccgacga cg                                             22
```

```
<210> SEQ ID NO 56
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (64)..(64)
<223> OTHER INFORMATION: Inverted deoxythymidine

<400> SEQUENCE: 56
cggacgcgaa ccgcgacgac gatagcaatc atatggctgt gctcatttaa taagcaagct      60
gggt                                                                    64

<210> SEQ ID NO 57
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (64)..(64)
<223> OTHER INFORMATION: Inverted deoxythymidine

<400> SEQUENCE: 57
cggacgcgaa ccgcgacgac gatgtgttag tgatgcgagc tccttaccat tagatagagg      60
ctgt                                                                    64

<210> SEQ ID NO 58
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (64)..(64)
<223> OTHER INFORMATION: Inverted deoxythymidine

<400> SEQUENCE: 58
cggacgcgaa ccgcgacgac gataaactct atcgtccaga gagaatgtct gcctactgat      60
ttgt                                                                    64

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
agggctgctt aggattgcga taata                                             25

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
```
agggctgctt aggattgcga aggta                                              25

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gggtctgctc taggattgcg ttcatg                                             26

<210> SEQ ID NO 62
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ggagctgttc cttgataccg attcaa                                             26

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gggactgctc aggattgcgg ataca                                              25

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
aggtctgctt aggattgcga aaaaa                                              25

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gggactgctc gggattgcga atcta                                              25

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
aggtctgctt aggattgcga atgtt                                              25

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
aggactgctt aggattgcga aaaca                                              25

<210> SEQ ID NO 68
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
cgggctgctc aaaggattgc gtagctt                                            27

<210> SEQ ID NO 69
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ataactgctc aataatatag ataaaa                                             26

<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
taagggctgc ttaggattgc gataata                                            27

<210> SEQ ID NO 71
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
atagggctgc ttaggattgc gaaggta                                            27

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ttaggtctgc ttaggattgc gaaaaaa                                            27

```
<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
taaggactgc ttaggattgc gaaaaca                                            27

<210> SEQ ID NO 74
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
tggggactgc tcgggattgc gaatcta                                            27
```

T-LYMPHOCYTE BINDING APTAMERS

RELATED APPLICATIONS

This application claims the benefit of priority to U.S. Provisional Patent Application Ser. Nos. 63/121,080, filed Dec. 3, 2020 and U.S. Provisional Patent Application Ser. Nos. 63/257,402, filed Oct. 19, 2021, each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Feb. 7, 2022, is named AUB-00301_SL.txt and is 20,120 bytes in size.

BACKGROUND

T cells have been established as core effectors for cancer immunotherapy, especially owing to their abundance, killing efficacy and capacity to proliferate. T-cell engagers are bispecific molecules directed against a constant-component of the T-cell/CD3 complex on one end and a tumor-associated antigen (TAA) on the other end. This structure and specificity allows a bispecific T cell engagers to physically link a T cell to a tumor cell, ultimately stimulating T cell activation and subsequent tumor killing. (Huehls A M et al (2015) *Immunol Cell Biol* 93(3): 290-296; Ellerman D (2019) *Methods* 154:102-117) Bispecific molecules harnessing and redirecting T-cells towards tumor cells are thus a promising therapeutic agent. Over the past three decades, a myriad of T-bispecific antibodies have been developed. To date, only a single T-bispecific antibody, blinatumomab, has been approved for clinical use in humans, as compared approximately 30 other IgG-based antibody drugs for cancer therapy. The lag is largely attributed to the difficulties in protein engineering during the manufacture of these antibodies and the uncertain clinical toxicities of these novel constructs (Wu and Cheung (2018) *Pharmacol. Ther.* 182: 161-175).

Aptamers are single stranded oligonucleotides which can specifically bind a variety of targets, including proteins, sugars, and small organic compounds. There is increasing interest in using aptamers for the development of both therapeutics and diagnostics.

Although aptamers recognize and bind targets of interest similarly to antibodies, they have a number of advantages, such as shorter generation time, lower costs of manufacturing, low batch-to-batch variability, higher modifiability, better thermal stability and low immunogenicity (Zhang, Lai, and Juhas (2019) *Molecules* 24: pii: E941. doi: 10.3390/molecules24050941).

Thus, aptamers that are capable of targeting T cells would have great potential for use as anti-cancer therapeutics.

SUMMARY

In certain aspects, provided herein are aptamers that bind to T cells and/or that induce T cell stimulation and/or T cell-mediated cytotoxicity. In some aspects, provided herein are pharmaceutical compositions comprising such aptamers, methods of using such aptamers to treat cancer and/or to kill cancer cells and/or stimulate T lymphocytes and methods of making such aptamers.

In certain aspects, provided herein are aptamers comprising a nucleic acid sequence that is at least 60% identical (e.g., at least 65% identical, at least 70% identical, at least 75% identical, at least 80% identical, at least 85% identical, at least 90% identical, at least 92% identical, at least 94% identical, at least 96% identical, at least 98% identical) to any one of SEQ ID NOs: 1-21. In certain embodiments, the aptamers comprise at least 20 (e.g., at least 25, at least 30, at least 35, at least 40, at least 41, at least 42, at least 43, at least 44, at least 45, at least 46, at least 47, at least 48, at least 49, or at least 50) consecutive nucleotides of any one of SEQ ID NO: 1-21. In certain embodiments, the aptamers comprise at least 40 (e.g., at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63) consecutive nucleotides of any one of SEQ ID NO: 1-21 In some embodiments, the aptamers comprise a nucleic acid sequence of any one of SEQ ID NOs: 1-21 (e.g., any one of SEQ ID NOs: 1, 20 and 21). In some embodiments, the aptamers provided herein have a sequence consisting essentially of any one of SEQ ID NOs: 1-21 (e.g., any one of SEQ ID NOs: 1, 20 or 21). In certain embodiments, the aptamers provided herein have a sequence consisting of any one of SEQ ID NO: 1-21 (e.g., any one of SEQ ID NOs: 1, 20 and 21).

In certain embodiments, the aptamers provided herein are no more than 100 nucleotides in length (e.g., no more than 90 nucleotides in length, no more than 85 nucleotides in length, no more than 80 nucleotides in length, no more than 75 nucleotides in length, no more than 73 nucleotides in length, no more than 70 nucleotides in length, no more than 63 in length, no more than 65 nucleotides in length, no more than 60 nucleotides in length, no more than 59 nucleotides in length, no more than 58 nucleotides in length, no more than 57 nucleotides in length, no more than 56 nucleotides in length, no more than 55 nucleotides in length, no more than 54 nucleotides in length, no more than 53 nucleotides in length, no more than 52 nucleotides in length, no more than 51 nucleotides in length, or no more than 50 nucleotides in length).

In some embodiments, the aptamers provided herein are able to bind to a T cell. In some embodiments, the aptamers provided herein bind to the T cell surface protein CD3 (e.g. CD3 epsilon chain, CD3ε). In some embodiments, the aptamers are able to induce T cell-mediated cytotoxicity. In some embodiments, the aptamers are able to induce cell death of a cancer cell (e.g., a human cancer cell) through T cell-mediated cytotoxicity. In some embodiments, the cancer cell is a patient-derived cancer cell. In some embodiments, the cancer cell is a solid tumor cell. In certain embodiments, the cancer cell is a colorectal carcinoma cell. In some embodiments, the cancer cell is a lung carcinoma cell. In some embodiments, the aptamers induce cell death of a cancer cell in vitro. In certain embodiments, the aptamers induce cell death of a cancer cell in vivo (e.g., in a human and/or an animal model). In some embodiments, the aptamers are able to induce T cell stimulation. In some embodiments, the aptamers are able to induce T cell proliferation.

In some embodiments, the aptamers provided herein comprise one or more chemical modifications. In some embodiments, the aptamers are chemically modified with poly-ethylene glycol (PEG) (e.g., attached to the 5' end of the aptamer). In some embodiments, the aptamers comprise a 5' end cap. In certain embodiments, the aptamers comprise a 3' end cap (e.g., is an inverted thymidine, biotin). In some embodiments, the aptamers comprise one or more (e.g., at least 1, 2, 3, 4, 5, 6, 7, 8, 9, 10 11, 12, 13, 14, 15, 16, 17, 18, 19, 20, 21, 22, 23, 24, 25, 26, 27, 28, 29, 30 31, 32, 33, 34, 35, 36, 37, 38, 39, 40, 41, 42, 43, 44, 45, 46, 47, 48, 49, 50, 51, 52, 53, or 54) 2' sugar substitutions (e.g. a 2'-fluoro, a 2'-amino, or a 2'-O-methyl substitution). In certain embodiments, the aptamers comprise locked nucleic acid (LNA), unlocked nucleic acid (UNA) and/or 2'deozy-2'fluoro-D-arabinonucleic acid (2'-F ANA) sugars in their backbone. In certain embodiments, the aptamers comprise one or more (e.g., at least 1, 2, 3, 4, 5, 6, 7, 8, 9, 10 11, 12, 13, 14, 15, 16, 17, 18, 19, 20, 21, 22, 23, 24, 25, 26, 27, 28, 29, 30 31, 32, 33, 34, 35, 36, 37, 38, 39, 40, 41, 42, 43, 44, 45, 46, 47, 48, 49, 50, 51, 52, 53, or 54) methylphosphonate internucleotide bonds and/or a phosphorothioate (PS) internucleotide bonds. In certain embodiments, the aptamers comprise one or more (e.g., at least 1, 2, 3, 4, 5, 6, 7, 8, 9, 10 11, 12, 13, 14, 15, 16, 17, 18, 19, 20, 21, 22, 23, 24, 25, 26, 27, 28, 29, 30 31, 32, 33, 34, 35, 36, 37, 38, 39, 40, 41, 42, 43, 44, 45, 46, 47, 48, 49, 50, 51, 52, 53, or 54) triazole internucleotide bonds. In certain embodiments, the aptamers are modified with a cholesterol or a dialkyl lipid (e.g., on their 5' end). In some embodiments, the aptamers comprise one or more modified bases.

In certain embodiments, the aptamers provided herein are DNA aptamers (e.g., D-DNA aptamers or enantiomer L-DNA aptamers). In some embodiments, the aptamers provided herein are RNA aptamers (e.g., D-RNA aptamers or enantiomer L-RNA aptamers). In some embodiments, the aptamers comprise a mixture of DNA and RNA.

In certain aspects, provided herein are aptamer conjugates comprising an aptamer provided herein linked to a cancer cell-binding moiety (e.g., a small molecule, another aptamer, a polypeptide, a nucleic acid, a protein, and/or an antibody). In some embodiments, the aptamer is covalently linked to the cancer cell-binding moiety. In some embodiments, the aptamer is non-covalently linked to the cancer cell-binding moiety. In some embodiments, the aptamer is directly linked to the cancer cell-binding moiety. In some embodiments, the aptamer is linked to the cancer cell-binding moiety via a linker. In some embodiments, the cancer-cell binding moiety binds to an antigen expressed on a cancer cell. In some embodiments, the antigen expressed on the cancer cell is selected from Prostate-specific antigen (PSA), Prostate Membrane Antigen (PSMA), Cancer antigen 15-3 (CA-15-3), Carcinoembryonic antigen (CEA), Cancer antigen 125 (CA-125), Alpha-fetoprotein (AFP), NY-ESO-1, MAGEA-A3, WT1, hTERT, Tyrosinase, gp 100, MART-1, melanA, B catenin, CDC27, HSP70-2-m, HLA-A2-R17OJ, AFP, EBV-EBNA, HPV16-E7, MUC-1, HER-2/neu, Mammaglobin-A or MHC-TAA peptide complexes. In some embodiments, the cancer-cell binding moiety induces cell death (e.g., apoptosis) when contacted to a cancer cell (e.g., a human cancer cell). In some embodiments, the cancer cell is a patient-derived cancer cell. In some embodiments, the cancer cell is a solid tumor cell. In certain embodiments, the cancer cell is a colorectal carcinoma cell. In some embodiments, the cancer cell is a breast cancer cell. In some embodiments, the cancer-cell binding moiety induces cell death when contacted to a cancer cell in vitro. In certain embodiments, the cancer-cell binding moiety induces cell death when contacted to a cancer cell in vivo (e.g., in a human and/or an animal model).

In certain aspects, provided herein are pharmaceutical compositions comprising an aptamer (e.g., a therapeutically effective amount of an aptamer) provided herein. In certain aspects, provided herein are pharmaceutical compositions comprising an aptamer conjugate (e.g., a therapeutically effective amount of an aptamer conjugate) provided herein. In some embodiments, the pharmaceutical compositions provided herein further comprise a pharmaceutically acceptable carrier. In some embodiments, the pharmaceutical compositions provided herein are formulated for parenteral administration.

In certain embodiments, the pharmaceutical compositions provided herein are for use in treating cancer. In some embodiments, the cancer is a solid tumor. In certain embodiments, the cancer is a colorectal carcinoma. In some embodiments, the cancer is a lung carcinoma.

In certain aspects, provided herein is a method of treating cancer in a subject, the method comprising administering to the subject an aptamer (e.g., a therapeutically effective amount of an aptamer) or a pharmaceutical composition provided herein. In certain aspects, provided herein is a method of treating cancer in a subject, the method comprising administering to the subject an aptamer conjugate (e.g., a therapeutically effective amount of an aptamer conjugate) or a pharmaceutical composition provided herein. In some embodiments, the administration is parenteral administration (e.g., subcutaneous administration). The administration may be an intratumoral injection, a subcutaneous injection or an intravesical instillation.

In some embodiments, the cancer is a solid tumor. In certain embodiments, the cancer is a colorectal carcinoma. In some embodiments, the cancer is a breast cancer, head and neck squamous cell carcinoma, adenoid cystic carcinoma, basal cell carcinoma, bladder cancer, pancreatic cancer, hepatocellular carcinoma, melanoma, or merkel cell carcinoma. In certain embodiments, the subject is a subject who has received chemotherapy. In certain embodiments, the subject is a subject who has had a tumor surgically removed (e.g., who has had a breast cancer tumor surgically removed).

In some embodiments, the therapeutic methods provided herein further comprise administering to the subject an additional cancer therapy. In some embodiments, the additional cancer therapy comprises chemotherapy. In certain embodiments, the additional cancer therapy comprises radiation therapy. In some embodiments, the additional cancer therapy comprises surgical removal of a tumor. In certain embodiments, the additional cancer therapy comprises administration of an immune checkpoint inhibitor, e.g., an anti-PD-1 antibody, an anti-PD-L1 antibody, an anti-PD-L2 antibody, an anti-CTLA4 antibody, an anti-TIGIT antibody, an anti-PVR antibody or an anti-Nectin antibody) to the subject.

In certain aspects, provided herein is a method of killing a cancer cell, the method comprising contacting the cancer cell with an aptamer or an aptamer conjugate provided herein. In some embodiments, the cancer cell is killed by apoptosis. In some embodiments, the cancer cell is a solid tumor cell. In certain embodiments, the cancer cell is a colorectal carcinoma cell. In some embodiments, the cancer cell is a breast cancer cell. In some embodiments, the cancer cell is killed when contacted with the cancer cell in vitro. In certain embodiments, the cancer cell is killed when contacted with the cancer cell in vivo (e.g., in a human and/or an animal model).

In certain aspects, provided herein is a method of making an aptamer. In some embodiments, the method comprises synthesizing (e.g., chemically synthesizing) a nucleic acid comprising a sequence that is at least 60% identical (e.g., at least 65% identical, at least 70% identical, at least 75% identical, at least 80% identical, at least 85% identical, at least 90% identical, at least 92% identical, at least 94% identical, at least 96% identical, at least 98% identical) to any one of SEQ ID NOs: 1-21 (e.g., any one of SEQ ID NOs: 1, 20 and 21). In certain embodiments, the method comprises synthesizing a nucleic acid comprising a sequence that comprises at least 20 (e.g., at least 25, at least 30, at least 35, at least 40, at least 41, at least 42, at least 43, at least 44, at least 45, at least 46, at least 47, at least 48, at least 49, or at least 50) consecutive nucleotides of any one of SEQ ID NO: 1-21 (e.g., any one of SEQ ID NOs: 1, 20, and 21). In certain embodiments, the aptamers comprise at least 40 (e.g., at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, or at least 73) consecutive nucleotides of any one of SEQ ID NO: 1-21 (e.g., any one of SEQ ID NOs: 1, 20 and 21). In certain embodiments, the method comprises synthesizing a nucleic acid comprising a sequence of any one of SEQ ID NOs: 1-21 (e.g., any one of SEQ ID NOs: 1, 20 and 21). In some embodiments, the method comprises synthesizing a nucleic acid having a sequence consisting essentially of SEQ ID NOs: 1-21 (e.g., any one of SEQ ID NOs: 1, 20 and 21). In certain embodiments, the method comprises synthesizing a nucleic acid having a sequence consisting of SEQ ID NO: 1-21 (e.g., any one of SEQ ID NOs: 1, 20 and 21).

BRIEF DESCRIPTION OF FIGURES

FIG. 3A shows analysis of single aptamer sequences from $8^{th}$, $9^{th}$, $10^{th}$, and $11^{th}$ SELEX rounds enriched libraries on dot plot where the X-axis represents mean P-negative and the Y-axis represents mean P-positive, as defined in example 2. The diagonal line represent the threshold between specific-binder aptamers and low, non-specific, binding aptamer sequences. Top 5 candidates selected for further examination indicated with their names. FIG. 3B shows sequences LOGO display of the shared motif (using GLAM2 software) of top 14 specific-binder aptamers (upper) and top 4 selected aptamers (lower). FIG. 3B discloses SEQ ID NOS 59-68, 59, and 69-74, respectively, in order of appearance. FIG. 3C shows secondary structural analysis (mfold) of the 5 selected candidates. Motif nucleotides location are marked with a red asterisk. FIG. 3C discloses SEQ ID NOS 1, 2, 3, 5, and 4, respectively, in order of appearance.

(FIG. 5A). Jurkat cells and Daudi cells were incubate with CpG'-Cy5 labelled CS6, CS7 and CS8c and analyzed by flow cytometry. MFI quantification is indicated below (FIG. 5B). Isolated pan T cells and pan B cells were incubate with CpG'-Cy5 labeled CS6 and analyzed by flow cytometry. Representation of dot plots with Cy5 (X-axis)/SSC (Y-axis) of T cells and B cells as well as MFI quantification are presented (FIG. 5C).

DETAILED DESCRIPTION

General

Figure 1A:
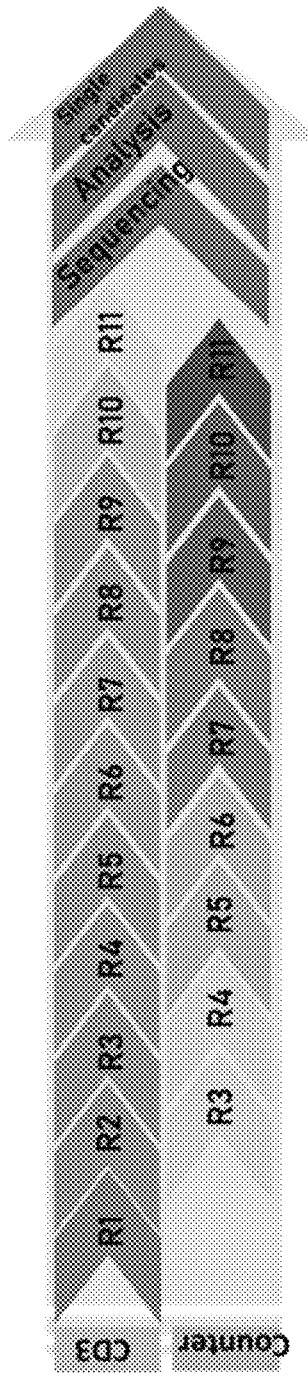
FIGS. 1A and 1B shows the scheme of binding SELEX process.

In certain aspects, provided herein are aptamers that selectively bind to T cells and/or selectively induces T cell stimulation and/or T cell-mediated cytotoxicity. In some aspects, provided herein are pharmaceutical compositions comprising such aptamers, methods of using such aptamers to treat cancer and/or to kill cancer cells and methods of making such aptamers.

Definitions

For convenience, certain terms employed in the specification, examples, and appended claims are collected here.

The articles "a" and "an" are used herein to refer to one or to more than one (e.g., to at least one) of the grammatical object of the article. By way of example, "an element" means one element or more than one element.

The terms "oligonucleotide" and "nucleic acid molecule" refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, synthetic polynucleotides, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component.

As used herein, the term "aptamer" refers to a short (e.g., less than 200 bases), single stranded nucleic acid molecule (ssDNA oligonucleotide and/or ssRNA) able to specifically bind to a target molecule, e.g., a protein or peptide, or to a topographic feature on a target cell.

The term "binding" or "interacting" refers to an association, which may be a stable association, between two molecules, e.g., between an aptamer and target, e.g., due to, for example, electrostatic, hydrophobic, ionic, pi-stacking, coordinative, van der Waals, covalent and/or hydrogen-bond interactions under physiological conditions.

As used herein, two nucleic acid sequences "complement" one another or are "complementary" to one another if they base pair one another at each position.

The term "modulation" or "modulate", when used in reference to a functional property or biological activity or process (e.g., enzyme activity or receptor binding), refers to the capacity to either up regulate (e.g., activate or stimulate), down regulate (e.g., inhibit or suppress) or otherwise change a quality of such property, activity, or process. In certain instances, such regulation may be contingent on the occurrence of a specific event, such as activation of a signal transduction pathway, and/or may be manifest only in particular cell types.

As used herein, "specific binding" refers to the ability of an aptamer to bind to a predetermined target. Typically, an aptamer specifically binds to its target with an affinity corresponding to a $K_D$ of about 10-7 M or less, about 10-8 M or less, or about 10-9 M or less and binds to the target with a $K_D$ that is significantly less (e.g., at least 2 fold less, at least 5 fold less, at least 10 fold less, at least 50 fold less, at least 100 fold less, at least 500 fold less, or at least 1000 fold less) than its affinity for binding to a non-specific and unrelated target (e.g., IgG1 globulin, BSA, casein, or an unrelated target, such as an HEK 293 cell or an *E. coli* cell) or than affinity of a different aptamer sequence to the cognate target.

Aptamers

In certain aspects, provided herein are aptamers that bind to T cells and/or induces T cell stimulation and/or induces T cell-mediated cytotoxicity. In some aspects, provided herein are pharmaceutical compositions comprising such aptamers, methods of using such aptamers to treat cancer and/or to kill cancer cells and methods of making such aptamers.

In certain aspects, provided herein are aptamers comprising a nucleic acid sequence that is at least 60% identical (e.g., at least 65% identical, at least 70% identical, at least 75% identical, at least 80% identical, at least 85% identical, at least 90% identical, at least 92% identical, at least 94% identical, at least 96% identical, at least 98% identical) to any one of SEQ ID NOs: 1-21). In certain embodiments, the aptamers comprise at least 20 (e.g., at least 25, at least 30, at least 35, at least 40, at least 41, at least 42, at least 43, at least 44, at least 45, at least 46, at least 47, at least 48, at least 49, at least 50) consecutive nucleotides of any one of SEQ ID NO: 1-21. In certain embodiments, the aptamers comprise at least 40 (e.g., at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, or at least 73) consecutive nucleotides of any one of SEQ ID NO: 1-21. In some embodiments, the aptamers comprise a nucleic acid sequence of any one of SEQ ID NOs: 1-21. In some embodiments, the aptamers provided herein have a sequence consisting essentially of any one of SEQ ID NOs: 1-21). In certain embodiments, the aptamers provided herein have a sequence consisting of any one of SEQ ID NO: 1-21.

The terms "identical" or "percent identity," in the context of two or more nucleic acids, refer to two or more sequences or subsequences that are the same or have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/or the like).

In certain embodiments, the aptamers are no more than 100 nucleotides in length (e.g., no more than 90 nucleotides in length, no more than 85 nucleotides in length, no more than 80 nucleotides in length, no more than 75 nucleotides in length, no more than 70 nucleotides in length, no more than 65 nucleotides in length, no more than 60 nucleotides in length, no more than 59 nucleotides in length, no more than 58 nucleotides in length, no more than 57 nucleotides in length, no more than 56 nucleotides in length, no more than 55 nucleotides in length, no more than 54 nucleotides in length, no more than 53 nucleotides in length, no more than 52 nucleotides in length, no more than 51 nucleotides in length, or no more than 50 nucleotides in length.

In some embodiments, the aptamers provided herein are able to bind to a T cell. In some embodiments, the aptamers provided herein bind to cluster of differentiation 3 (CD3) (e.g., to the CD3 epsilon chain). In some embodiments, the aptamers are able to induce T cell stimulation. In some embodiments, the aptamers are able to induce T cell-mediated cytotoxicity. In some embodiments, the aptamers are able to induce cell death of a cancer cell (e.g., a human cancer cell) through T cell-mediated cytotoxicity. In some embodiments, the cancer cell is a patient-derived cancer cell. In some embodiments, the cancer cell is a solid tumor cell. In certain embodiments, the cancer cell is a colorectal carcinoma cell. In some embodiments, the cancer cell is a lung cancer cell. In some embodiments, the aptamers induce cell death of a cancer cell in vitro. In certain embodiments, the aptamers induce cell death of a cancer cell in vivo (e.g., in a human and/or an animal model).

In some embodiments, the aptamers provided herein comprise one or more chemical modifications. Exemplary modifications are provided in Table 1.

In certain embodiments, the aptamers comprise one or more (e.g., at least 1, 2, 3, 4, 5, 6, 7, 8, 9, 10 11, 12, 13, 14, 15, 16, 17, 18, 19, 20, 21, 22, 23, 24, 25, 26, 27, 28, 29, 30 31, 32, 33, 34, 35, 36, 37, 38, 39, 40, 41, 42, 43, 44, 45, 46, 47, 48, 49, 50, 51, 52, 53, or 54) methylphosphonate internucleotide bonds and/or a phosphorothioate (PS) internucleotide bonds (e.g., on their 5' end). In certain embodiments, the aptamers comprise one or more (e.g., at least 1, 2, 3, 4, 5, 6, 7, 8, 9, 10 11, 12, 13, 14, 15, 16, 17, 18, 19, 20, 21, 22, 23, 24, 25, 26, 27, 28, 29, 30 31, 32, 33, 34, 35, 36, 37, 38, 39, 40, 41, 42, 43, 44, 45, 46, 47, 48, 49, 50, 51, 52, 53, or 54) triazole internucleotide bonds. In certain embodiments, the aptamers are modified with a cholesterol or a dialkyl lipid.

In some embodiments, the aptamers comprise one or more modified bases (e.g., BzdU, Naphtyl, Triptamino, Isobutyl, 5-Methyl Cytosine, Alkyne (dibenzocyclooctyne, Azide, Maleimide).

In certain embodiments, the aptamers provided herein are DNA aptamers (e.g., D-DNA aptamers or enantiomer L-DNA aptamers). In some embodiments, the aptamers provided herein are RNA aptamers (e.g., D-RNA aptamers

TABLE 1

Exemplary chemical modifications.

| Terminal | Sugar ring | Nitrogen base | Backbone |
|---|---|---|---|
| Inverted-dT | 2'-OH (RNA) | BzdU | Phosphorothioate |
| Biotin | 2'-OMe | Naphtyl | Methylphosphorothioate |
| PEG (0.5-40 kDa) | 2'-F | Triptamino | Phosphorodithioate |
| Cholesterol | 2'-NH2 | Isobutyl | Triazole |
| Albumin | LNA | 5-Methyl Cytosine | Amide (PNA) |
| Chitin (0.5-40 kDa) | UNA | Alkyne (dibenzocyclooctyne) | Alkyne (dibenzocyclooctyne) |
| Chitosan (0.5-40 kDa) | 2'-F ANA | Azide | Azide |
| Cellulose (0.5-40 kDa) | L-DNA | Maleimide | Maleimide |
| Terminal amine (alkyne chain with amine) | CeNA | | |
| Alkyl (dibenzocyclooctyne) | TNA | | |
| Azide | HNA | | |
| Thiol | | | |
| Maleimide | | | |
| NHS | | | |

In certain embodiments, the aptamers comprise a terminal modification. In some embodiments, the aptamers are chemically modified with poly-ethylene glycol (PEG) (e.g., 0.5-40 kDa) (e.g., attached to the 5' end of the aptamer). In some embodiments, the aptamers comprise a 5' end cap (e.g., is an inverted thymidine, biotin, albumin, chitin, chitosan, cellulose, terminal amine, alkyne, azide, thiol, maleimide, NHS). In certain embodiments, the aptamers comprise a 3' end cap (e.g., is an inverted thymidine, biotin, albumin, chitin, chitosan, cellulose, terminal amine, alkyne, azide, thiol, maleimide, NHS).

In certain embodiments, the aptamers provided herein comprise one or more (e.g., at least 1, 2, 3, 4, 5, 6, 7, 8, 9, 10 11, 12, 13, 14, 15, 16, 17, 18, 19, 20, 21, 22, 23, 24, 25, 26, 27, 28, 29, 30 31, 32, 33, 34, 35, 36, 37, 38, 39, 40, 41, 42, 43, 44, 45, 46, 47, 48, 49, 50, 51, 52, 53, or 54) modified sugars. In some embodiments, the aptamers comprise one or more 2' sugar substitutions (e.g. a 2'-fluoro, a 2'-amino, or a 2'-O-methyl substitution). In certain embodiments, the aptamers comprise locked nucleic acid (LNA), unlocked nucleic acid (UNA) and/or 2'deozy-2'fluoro-D-arabino-nucleic acid (2'-F ANA) sugars in their backbone.

or enantiomer L-RNA aptamers). In some embodiments, the aptamers comprise a mixture of DNA and RNA.

Aptamers may be synthesized by methods which are well known to the skilled person. For example, aptamers may be chemically synthesized, e.g. on a solid support. Solid phase synthesis may use phosphoramidite chemistry. Briefly, the synthesis cycle starts with the removal of the acid-labile 5'-dimethoxytrityl protection group (DMT, "Trityl") from the hydroxyl function of the terminal, support-bound nucleoside by UV-controlled treatment with an organic acid. The exposed highly-reactive hydroxyl group is then available to react in the coupling step with the next protected nucleoside phosphoramidite building block, forming a phosphite triester backbone. Next, the acid-labile phosphite triester backbone is oxidized to the stable pentavalent phosphate trimester. If a phosphorothioate modification is desired at a specific backbone position, the acid labile phosphite trimester backbone is sulfuridized at this step, instead of the oxidation process, to generate a P=S bond rather than a P=O. Successively, all the unreacted 5'-hydroxyl groups are acetylated ("capped") in order to block these sites during the next coupling step, avoiding internal mismatch sequences.

Following the capping step, the cycle starts again by removal of the DMT-protection group and successive coupling of the next base according to the desired sequence. Finally, the oligonucleotide is cleaved from the solid support and all protection groups are removed from the backbone and bases.

Aptamer Conjugate

In certain aspects, provided herein are aptamer conjugates comprising an aptamer provided herein linked to a cancer cell-binding moiety. The cancer cell-binding moiety may be, e.g., an aptamer, a small molecule, a polypeptide, a nucleic acid, a protein, or an antibody. In some embodiments, the aptamer is covalently linked to the cancer cell-binding moiety. In some embodiments, the aptamer is non-covalently linked to the cancer cell-binding moiety. In some embodiments, the aptamer is directly linked to the cancer cell-binding moiety. In some embodiments, the aptamer is linked to the cancer cell-binding moiety via a linker.

In some embodiments, the cancer-cell binding moiety binds to an antigen expressed on a cancer cell. In some embodiments, the cancer-cell binding moiety binds to a cancer antigen selected from Prostate-specific antigen (PSA), Prostate Membrane Antigen (PSMA)Cancer antigen 15-3 (CA-15-3), Carcinoembryonic antigen (CEA), Cancer antigen 125 (CA-125), Alpha-fetoprotein (AFP), NY-ESO-1, MAGEA-A3, WT1, hTERT, Tyrosinase, gp100, MART-1, melanA, B catenin, CDC27, HSP70-2-m, HLA-A2-R17OJ, AFP, EBV-EBNA, HPV16-E7, MUC-1, HER-2/neu, Mammaglobin-A or MHC-TAA peptide complexes In some embodiments, the cancer-cell binding moiety induces cell death (e.g., apoptosis) when contacted to a cancer cell (e.g., a human cancer cell). In some embodiments, the cancer cell is a patient-derived cancer cell. In some embodiments, the cancer cell is a solid tumor cell. In certain embodiments, the cancer cell is a colorectal carcinoma cell. In some embodiments, the cancer cell is a breast cancer cell. In some embodiments, the cancer-cell binding moiety induces cell death when contacted to a cancer cell in vitro. In certain embodiments, the cancer-cell binding moiety induces cell death when contacted to a cancer cell in vivo (e.g., in a human and/or an animal model).

Bispecific Personalized Aptamers

In certain aspects, provided herein are bispecific personalized aptamers that comprise (a) a cancer cell-binding strand that specifically binds to an antigen expressed on a cancer cell; (b) a CpG motif; and (c) a CD3-binding strand (e.g., a CD3-binding aptamer disclosed herein), wherein the cancer cell-binding strand is linked to the CD3-binding strand by the CpG motif.

In some embodiments, the cancer cell-binding strand is able to induce cell death (e.g., apoptosis) of a cancer cell (e.g., a human cancer cell) when contacted to the cancer cell. In some embodiments, the cancer cell is a patient-derived cancer cell. In some embodiments, the cancer cell is a solid tumor cell (e.g., a breast cancer cell). In certain embodiments, the cancer cell is a carcinoma cell (e.g., a colorectal carcinoma cell). In some embodiments, the aptamers induce cell death when contacted to the cancer cell in vitro. In certain embodiments, the aptamers induce cell death when contacted to the cancer cell in vivo (e.g., in a human and/or an animal model). In some embodiments, the cancer cell-binding strand binds to a cancer antigen selected from Prostate Membrane Antigen (PSMA), Cancer antigen 15-3 (CA-15-3), Carcinoembryonic antigen (CEA), Cancer antigen 125 (CA-125), Tyrosinase, gp100, MART-1/melan-A, HSP70-2-m, HLA-A2-R17OJ, HPV16-E7, MUC-1, HER-2/neu, Mammaglobin-A or MHC-TAA peptide complexes.

In certain embodiments, the cancer cell-binding strand comprises a nucleic acid sequence that is at least 60% identical (e.g., at least 65% identical, at least 70% identical, at least 75% identical, at least 80% identical, at least 85% identical, at least 90% identical, at least 92% identical, at least 94% identical, at least 96% identical, at least 98% identical) to any one of SEQ ID NOs: 28-51. In some embodiments, the cancer cell-binding strand comprises a nucleic acid sequence of any one of SEQ ID NOs: 28-51. In certain embodiments, the cancer cell-binding strand comprises at least 30 (e.g., at least 35, at least 40, at least 45, at least 50, at least 55, at least 56, at least 57, at least 58, at least 59, at least 60, at least 61, at least 62, at least 63, at least 64, at least 65, at least 66, at least 67, at least 68, at least 69) consecutive nucleotides of any one of SEQ ID NO: 28-47. In some embodiments, the cancer cell-binding strand has a sequence consisting essentially of SEQ ID NOs: 28-51. In certain embodiments, the cancer cell-binding strand has a sequence consisting of SEQ ID NO: 28-51.

TABLE 2

SEQ ID numbers

| Category | Aptamer name | SEQ ID NO: | Sequence 5' to 3' |
|---|---|---|---|
| CD3 Binder | CS6 | 1 | ATCGTATAAGGGCTGCTTAGGATTGCGATAATACGGTCAA |
| | CS7 | 2 | CATTTCATAGGGCTGCTTAGGATTGCGAAGGTAATGCCAG |
| | CS8 | 3 | CCCTTACCCCTTTTAGGTCTGCTTAGGATTGCGAAAAAAG |
| | CS9 | 4 | TTGTAAGGACTGCTTAGGATTGCGAAAACAATATTCGTAT |
| | CS8c | 5 | CTTTTAGGTCTGCTTAGGATTGCGAAAAAAG |
| | Ppos 10 | 6 | TCCATGGGTCTGCTCTAGGATTGCGTTCATGGTCTCCCCG |
| | Ppos 11 | 7 | AATTACAACCTTGGATTGCAAAGGGCTGCTGTGTTGTTTA |
| | Ppos 12 | 8 | ATCGGAGCTGTTCCTTGATACCGATTCAAAAAGTTCGTAC |
| | Ppos 13 | 9 | AATTTGTAGGGACTGCTCAGGATTGCGGATACAAATTAAT |
| | Ppos 14 | 10 | AGACATTGGGGACTGCTCGGGATTGCGAATCTATGTCTCC |
| | Ppos 15 | 11 | CCCTTTTTTAACTAGGTCTGCTTAGGATTGCGAATGTTAA |
| | Ppos 16 | 12 | ACCTCAAAAGCGCGGGCTGCTCAAAGGATTGCGTAGCTTT |
| | Ppos 17 | 13 | GGGGGTTAAGGGCTGCTTAGGATTGCGATAATACGGTCAA |
| | Ppos 18 | 14 | AACATATAACTGCTCAATAATATAGATAAAATACTCACAA |
| | CS1 | 15 | CTCTACCTGACTGTAACCTCTCGCTCCCCCCCATTCGCGC |
| | CS2 | 16 | TTGTCCCTCTACGCCGCCCTTTACTACCACTCCTGCGATT |
| | CS3 | 17 | TCCAGCACACCGACCGCCCCTCTACATTACCCCCTGGACT |
| | CS4 | 18 | CCCCTCCATTCCCCCGCCTCGTCCACCCTACTCCTTAGTC |
| | CS5 | 19 | CATCGACGCCCACACACCACTTCCCGTTCCCCTGCATCAT |

TABLE 2-continued

SEQ ID numbers

| Category | Aptamer name | SEQ ID NO: | Sequence 5' to 3' |
|---|---|---|---|
| Cancer-Cell Targeting Variable Strands | HCT116-VS6 | 28 | TCCTTGTCAGCACTTTCAGAGCACTTTCCCGTAGAACTTAAGGGACATGC |
| | HCT116-VS12 | 29 | GATTGATCTATTTTCCATATCGCGTTGAGTGTAAAGCCACGAAGGGTTAT |
| | MCF7-VS13 | 30 | ATTGGAGTTTTCCAATCAGAAAGGATTCGGTCAGCTGCAC |
| | MCF7-VS16 | 31 | TGGAAACAGCTGCAACTTTTCTGGGACGTGAATGCCTCGC |
| | MCF7-VS19 | 32 | ACTCAAAAATTAGGCAGGTGTAAGTATAACTCGTGCCTGC |
| | A549-VS3 | 33 | GCAGGCGGAAAATGTCAGGGCACGTTGGTCACGTATTTTT |
| | A549-VS20 | 34 | AGCAATCATATGGCTGTGCTCATTTAATAAGCAAGCTGGG |
| CpG motif-Variable Strand (* represents a PS modification) | CpG1'\|HCT116-VS6 | 35 | CGGACGCGAACGCCGACGACGATTCCTTGTCAGCACTTTCAGAGCACTTTCCCGTAGAACTTAAGGGACATGC |
| | CpG1'\|HCT116-VS12 | 36 | CGGACGCGAACCGCGACGACGATGATTGATCTATTTTCCATATCGCGTTGAGTGTAAAGCCACGAAGGGTTAT |
| | 5PS-CpG1'\|HCT116-VS12 | 37 | C*G*G*A*C*GCGAACCGCGACGACGATGATTGATCTATTTTCCATATCGCGTTGAGTGTAAAGCCACGAAGGGTTAT |
| | 10PS-CpG1'\|HCT116-VS12 | 38 | C*G*G*A*C*GCGAACCGCGACG*A*C*G*A*TGATTGATCTATTTTCCATATCGCGTTGAGTGTAAAGCCACGAAGGGTAT |
| | FullPS-CpG1'\|HCT116-VS12 | 39 | C*G*G*A*C*G*C*G*A*A*C*C*G*C*G*A*C*G*A*C*G*A*TGATTGATCTATTTTCCATATCGCGTTGAGTGTAAAGCCACGAAGGGTTAT |
| | CpG1'\|MCF7-VS13 | 40 | CGGACGCGAACCGCGACGACGATATTGGAGTTTTCCAATCAGAAAGGATTCGGTCAGCTGCAC |
| | CpG1'\|MCF7-VS16 | 41 | CGGACGCGAACCGCGACGACGATTGGAAACAGCTGCAACTTTTCTGGGACGTGAATGCCTCGC |
| | CpG1'\|MCF7-VS19 | 42 | CGGACGCGAACCGCGACGACGATACTCAAAAATTAGGCAGGTGTAAGTATAACTCGTGCCTGC |
| | CpG'\|A549-VS3 | 43 | C*G*G*A*C*GCGAACCGCGACGACGATGCAGGCGGAAAATGTCAGGGCACGTTGGTCACGTATTTTT |
| | CpG'\|A549-VS20 | 44 | C*G*G*A*C*GCGAACCGCGACGACGATAGCAATCATATGGCTGTGCTCATTTAATAAGCAAGCTGGG |
| Non-CpG 22b complementary seq-Variable Strand | Non-CpG'\|HCT116-VS6 | 45 | ATTTGTATAATGTCTGATTAAGTTCCTTGTCAGCACTTTCAGAGCACTTTCCCGTAGAACTTAAGGGACATGC |
| | Non-CpG'\|HCT116-VS12 | 46 | ATTTGTATAATGTCTGATTAAGTGATTGATCTATTTTCCATATCGCGTTGAGTGTAAAGCCACGAAGGGTTAT |
| | Non-CpG'\|MCF7-VS13 | 47 | ATTTGTATAATGTCTGATTAAGTATTGGAGTTTTCCAATCAGAAAGGATTCGGTCAGCTGCAC |
| | Non-CpG'\|VS16 | 48 | ATTTGTATAATGTCTGATTAAGTTGGAAACAGCTGCAACTTTTCTGGGACGTGAATGCCTCGC |
| | Non-CpG'\|VS19 | 49 | ATTTGTATAATGTCTGATTAAGTACTCAAAAATTAGGCAGGTGTAAGTATAACTCGTGCCTGC |
| Non-CpG 18b complementary seq-Variable Strand | Non CpG 18b'\|HCT116 VS6 | 50 | CGTTATAATTGTTAATTCTTCCTTGTCAGCACTTTCAGAGCACTTTCCCGTAGAACTTAAGGGACATGC |
| | Non CpG 18b'\|HCT116 VS12 | 51 | CGTTATAATTGTTAATTCTGATTGATCTATTTTCCATATCGCGTTGAGTGTAAAGCCACGAAGGGTTAT |
| CpG motifs | CpG1 | 52 | TCGTCGTCGCGGTTCGCGTCCG |
| | CpG1' | 53 | CGGACGCGAACGCCGACGACGA |
| | CpG2 | 54 | CGTCGTCGGTCGTCGTCGCTCG |
| | CpG2' | 55 | CGAGCGACGACGACCGACGACG |

The terms "identical" or "percent identity," in the context of two or more nucleic acids, refer to two or more sequences or subsequences that are the same or have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/or the like).

In certain embodiments, the cancer cell-binding strand is no more than 120 nucleotides in length (e.g., no more than 115 nucleotides in length, no more than 110 nucleotides in length, no more than 105 nucleotides in length, no more than 100 nucleotides in length, no more than 95 nucleotides in length, no more than 90 nucleotides in length, no more than 85 nucleotides in length, no more than 80 nucleotides in length, no more than 75 nucleotides in length, no more than 70 nucleotides in length, no more than 69 nucleotides in length, no more than 68 nucleotides in length, no more than 67 nucleotides in length, no more than 66 nucleotides in length, no more than 65 nucleotides in length, no more than 64 nucleotides in length, or no more than 63 nucleotides in length). In certain embodiment, the cancer cell-binding strand is about 63 nucleotides in length.

In some embodiments, the CD3-binding strand comprises a nucleic acid sequence that is at least 60% identical (e.g., at least 65% identical, at least 70% identical, at least 75% identical, at least 80% identical, at least 85% identical, at least 90% identical, at least 92% identical, at least 94% identical, at least 96% identical, at least 98% identical) to any one of SEQ ID NOs: 1-21. In some embodiments, the CD3-binding strand comprises a nucleic acid sequence of any one of SEQ ID NOs: 1-21.

In certain embodiments, the CD3-binding strand comprises at least 20 (e.g., at least 25, at least 30, at least 35, at least 40, at least 41, at least 42, at least 43, at least 44, at least 45, at least 46, at least 47, at least 48, at least 49, at least 50, at least 51, at least 52, at least 53) consecutive nucleotides of any one of SEQ ID NOs: 1-21. In some embodiments, the CD3-binding strand provided herein has a sequence consisting essentially of SEQ ID NOs: 1-21. In certain embodiments, the CD3-binding strand provided herein has a sequence consisting of SEQ ID NO: 1-21. In certain embodiments, the CD3-binding is no more than 120 nucleotides in length (e.g., no more than 115 nucleotides in length, no more than 110 nucleotides in length, no more than 105 nucleotides in length, no more than 100 nucleotides in length, no more than 95 nucleotides in length, no more than 90 nucleotides in length, no more than 85 nucleotides in length, no more than 80 nucleotides in length, no more than 75 nucleotides in length, no more than 74 nucleotides in length, or no more than 73 nucleotides in length). In certain embodiments, the CD3-binding strand is about 73 nucleotides in length.

The cancer cell-binding strand and the CD3-binding strand may be linked together by hybridization of a 5' sequence of the cancer cell-binding strand to a 5' sequence of the CD3-binding strand. In certain embodiments, the 5' sequence of the cancer cell-binding strand hybridizes to the 5' sequence of the CD3-binding strand to form a CpG-rich motif, TLR9 agonistic sequence. The cancer cell-binding strand and the CD3-binding strand may be linked together by directly ligating to each of the two ends (e.g., the 5' ends) of a double-strand sequence. In certain embodiments, the double-strand sequence is a CpG motif, a TLR9 agonist sequence.

In some embodiments, the TLR9 agonist sequence comprises a double-stranded region comprising at least one (e.g., 1, 2, 3, 4, 5, 6, 7, 8, 9, 10, 11, 12, 13, 14, 15, 16, 17, 18, 19, 20) CpG motif nucleotides. In some embodiments, the CpG motif induces TLR9-mediated antigen presenting cell (APCs) stimulation and/or increased uptake of tumor antigens. In some embodiments, the TLR9 agonist sequence induces an anti-tumor response. In some embodiments, the TLR9 agonist sequence induces cytokines production.

In some embodiments, the CPG motif sequence is a double-stranded nucleic acid sequence comprising a sequence that is at least 60% identical (e.g., at least 65% identical, at least 70% identical, at least 75% identical, at least 80% identical, at least 85% identical, at least 90% identical, at least 92% identical, at least 94% identical, at least 96% identical, at least 98% identical) to any one of SEQ ID NOs: 52-55. In some embodiments, the CpG motif sequence is a double-stranded nucleic acid sequence comprising a sequence of any one of SEQ ID NOs: 52-55.

In certain embodiments, the CpG motif sequence is a double-stranded nucleic acid sequence comprising at least 12 (e.g., at least 13, at least 14, at least 15, at least 16, at least 17, at least 18, at least 19, at least 20, at least 21, at least 22) consecutive nucleotides of any one of SEQ ID NO: 52-55. In some embodiments, the CpG motif sequence provided herein has a sequence consisting essentially of SEQ ID NOs: 52-55. In certain embodiments, the CpG motif sequence provided herein has a sequence consisting of SEQ ID NO: 52-55.

In certain embodiments, the CpG motif sequence is no more than 35 nucleotides in length (e.g., no more than 34 nucleotides in length, no more than 33 nucleotides in length, no more than 32 nucleotides in length, no more than 31 nucleotides in length, no more than 30 nucleotides in length, no more than 29 nucleotides in length, no more than 28 nucleotides in length, no more than 27 nucleotides in length, no more than 26 nucleotides in length, no more than 25 nucleotides in length, no more than 24 nucleotides in length, no more than 23 nucleotides in length, or no more than 22 nucleotides in length).

The bispecific personalized aptamer provided herein may comprise any combination of the cancer cell-binding strand and the CD3-binding strand described herein.

In some embodiments, the bispecific personalized aptamers provided herein comprise one or more chemical modifications. Exemplary modifications are provided in Table 3.

TABLE 3

| Exemplary chemical modifications. | | | |
|---|---|---|---|
| Terminal | Sugar ring | Nitrogen base | Backbone |
| biotin | 2'-OH (RNA) | BzdU | Phosphorothioate |
| Inverted-dT | 2'-OMe | Naphtyl | Methylphosphorothioate |
| PEG (0.5-40 kDa) | 2'-F | Triptamino | Phosphorodithioate |
| Cholesterol | 2'-NH2 | Isobutyl | Triazole |
| Albumin | LNA | 5-Methyl Cytosine | Amide (PNA) |
| Chitin (0.5-40 kDa) | UNA | Alkyne (dibenzocyclooctyne) | Alkyne (dibenzocyclooctyne) |
| Chitosan (0.5-40 kDa) | 2'-F ANA | Azide | Azide |
| Cellulose (0.5-40 kDa) | L-DNA | Maleimide | Maleimide |
| Terminal amine (alkyne chain with amine) | CeNA | | |
| Alkyl (dibenzocyclooctyne) | TNA | | |
| Azide | HNA | | |
| Thiol | | | |
| Maleimide | | | |
| NHS | | | |

In certain embodiments, the bispecific personalized aptamers comprise a terminal modification. In some embodiments, the bispecific personalized aptamers are chemically modified with poly-ethylene glycol (PEG) (e.g., 0.5-40 kDa) (e.g., attached to the 5' end of the aptamer). In some embodiments, the bispecific personalized aptamers comprise a 5' end cap (e.g., is an inverted thymidine, biotin, albumin, chitin, chitosan, cellulose, terminal amine, alkyne, azide, thiol, maleimide, NHS). In certain embodiments, the bispecific personalized aptamers comprise a 3' end cap (e.g., is an inverted thymidine, biotin, albumin, chitin, chitosan, cellulose, terminal amine, alkyne, azide, thiol, maleimide, NHS).

In certain embodiments, the bispecific personalized aptamers provided herein comprise one or more (e.g., at least 1, 2, 3, 4, 5, 6, 7, 8, 9, 10 11, 12, 13, 14, 15, 16, 17, 18, 19, 20, 21, 22, 23, 24, 25, 26, 27, 28, 29, 30 31, 32, 33, 34, 35, 36, 37, 38, 39, 40, 41, 42, 43, 44, 45, 46, 47, 48, 49, 50, 51, 52, 53, or 54) modified sugars. In some embodiments, the bispecific personalized aptamers comprise one or more 2' sugar substitutions (e.g. a 2'-fluoro, a 2'-amino, or a 2'-O-methyl substitution). In certain embodiments, the bispecific personalized aptamers comprise locked nucleic acid (LNA), unlocked nucleic acid (UNA) and/or 2'deozy-2'fluoro-D-arabinonucleic acid (2'-F ANA) sugars in their backbone.

In certain embodiments, the bispecific personalized aptamers comprise one or more (e.g., at least 1, 2, 3, 4, 5, 6, 7, 8, 9, 10 11, 12, 13, 14, 15, 16, 17, 18, 19, 20, 21, 22, 23, 24, 25, 26, 27, 28, 29, 30 31, 32, 33, 34, 35, 36, 37, 38, 39, 40, 41, 42, 43, 44, 45, 46, 47, 48, 49, 50, 51, 52, 53, or 54) methylphosphonate internucleotide bonds and/or phosphorothioate (PS) internucleotide bonds.

In certain embodiments, the bispecific personalized aptamers may comprise PS modification within the double stranded region (e.g., the CpG motif sequence). For example, the double stranded region (e.g., the CpG motif sequence) of the bispecific personalized aptamers may comprise 1, 2, 3, 4, 5, 6, 7, 8, 9, 10, 11, 12, 13, 14, 15, 16, 17, 18, 19, 20, 21, 22 or 23 phosphorothioate (PS) internucleotide bonds on one or both strands. In some embodiments, the double stranded region (e.g., the CpG motif sequence) of the bispecific personalized aptamers may comprise a partial PS modification. In certain embodiments, 5 nucleotides from 5' ends of the double-stranded CpG motif sequence are modified. In other embodiments, 5 nucleotides from both 5' and 3' ends of the double-stranded CpG motif sequence are modified. In certain embodiments, the double-stranded CpG motif sequence comprises a complete PS modification.

In certain embodiments, the aptamers comprise one or more (e.g., at least 1, 2, 3, 4, 5, 6, 7, 8, 9, 10 11, 12, 13, 14, 15, 16, 17, 18, 19, 20, 21, 22, 23, 24, 25, 26, 27, 28, 29, 30 31, 32, 33, 34, 35, 36, 37, 38, 39, 40, 41, 42, 43, 44, 45, 46, 47, 48, 49, 50, 51, 52, 53, or 54) triazole internucleotide bonds. In certain embodiments, the aptamers are modified with a cholesterol or a dialkyl lipid (e.g., on their 5' ends).

In some embodiments, the aptamers comprise one or more modified bases (e.g., BzdU, Naphtyl, Triptamino, Isobutyl, 5-Methyl Cytosine, Alkyne (dibenzocyclooctyne, Azide, Maleimide).

In certain embodiments, the aptamers provided herein are DNA aptamers (e.g., D-DNA aptamers or enantiomer L-DNA aptamers). In some embodiments, the aptamers provided herein are RNA aptamers (e.g., D-RNA aptamers or enantiomer L-RNA aptamers). In some embodiments, the aptamers comprise a mixture of DNA and RNA.

Pharmaceutical Compositions

In certain aspects, provided herein are pharmaceutical compositions comprising an aptamer (e.g., a therapeutically effective amount of an aptamer) provided herein. In certain aspects, provided herein are pharmaceutical compositions comprising an aptamer conjugate (e.g., a therapeutically effective amount of an aptamer conjugate) provided herein. In some embodiments, the pharmaceutical compositions provided herein further comprise a pharmaceutically acceptable carrier. In some embodiments, the pharmaceutical compositions provided herein are formulated for parenteral administration (e.g., subcutaneous administration). The administration may be an intratumoral injection or a subcutaneous injection or an intravesical instillation.

In certain embodiments, the pharmaceutical compositions are for use in treating cancer. In some embodiments, the cancer is a solid tumor. In certain embodiments, the cancer is a carcinoma (e.g., a colorectal carcinoma). In some embodiments, the cancer is a lung cancer.

"Pharmaceutically acceptable carrier" refers to a substance that aids the administration of an active agent to and absorption by a subject and can be included in the compositions described herein without causing a significant adverse toxicological effect on the patient. Non-limiting examples of pharmaceutically acceptable excipients include water, NaCl, normal saline solutions, Phosphate-buffered solution, $MgCl_2$, KCl, $CaCl_2$, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylase or starch, fatty acid esters, lipids, hydroxymethy cellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compositions described herein. One of skill in the art will recognize that other pharmaceutical excipients are useful.

Therapeutic Methods

In some aspects, provided herein are methods of treating cancer comprising the administration of a pharmaceutical composition comprising one or more aptamers provided herein.

In some aspects, provided herein are methods of treating cancer comprising the administration of a pharmaceutical composition comprising one or more aptamer conjugates provided herein.

In some embodiments, the cancer is a solid tumor. In certain embodiments, the cancer is a colorectal carcinoma. In some embodiments, the cancer is a lung cancer. Thus, in certain aspects, provided herein is a method of delivering an aptamer, an aptamer conjugate, and/or a pharmaceutical composition described herein to a subject.

In certain embodiments, the pharmaceutical compositions, aptamers and aptamer conjugates described herein can be administered in conjunction with any other conventional anti-cancer treatment, such as, for example, radiation therapy and surgical resection of the tumor. These treatments may be applied as necessary and/or as indicated and may occur before, concurrent with or after administration of the pharmaceutical compositions, aptamers, aptamer conjugates, dosage forms, and kits described herein.

In certain embodiments, the method comprises the administration of multiple doses of the aptamer or aptamer conjugate. Separate administrations can include any number of two or more administrations (e.g., doses), including 2, 3, 4, 5, 6, 7, 8, 9, 10, 11, 12, 13, 14, 15, 16, 20, 21, 22, 23, 24, or 25 administrations. In some embodiments, at least 8, 9, 10, 11, 12, 13, 14, or 15 administrations are included. One skilled in the art can readily determine the number of administrations to perform, or the desirability of performing one or more additional administrations, according to methods known in the art for monitoring therapeutic methods and other monitoring methods provided herein. Accordingly, the methods provided herein include methods of providing to the subject one or more administrations of an aptamer, an aptamer conjugate and/or a pharmaceutical composition described herein, where the number of administrations can be determined by monitoring the subject, and, based on the results of the monitoring, determining whether or not to provide one or more additional administrations. Deciding on whether or not to provide one or more additional administrations can be based on a variety of monitoring results, including, but not limited to, stimulation of T cells, cytotoxic activity of T cells, indication of tumor growth or inhibition of tumor growth, appearance of new metastases or inhibition of metastasis, the subject's anti-tumor antibody titer, the overall health of the subject and/or the weight of the subject.

The time period between administrations can be any of a variety of time periods. In some embodiments, the doses may be separated by at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days or 1, 2, 3, or 4 weeks. The time period between administrations can be a function of any of a variety of factors, including monitoring steps, as described in relation to the number of administrations, the time period for a subject to mount an immune response and/or the time period for a subject to clear the aptamers or aptamer conjugates from normal tissue. In one example, the time period can be a function of the time period for a subject to mount an immune response; for example, the time period can be more than the time period for a subject to mount an immune response, such as more than about one week, more than about ten days, more than about two weeks, or more than about a month; in another example, the time period can be less than the time period for a subject to mount an immune response, such as less than about one week, less than about ten days, less than about two weeks, or less than about a month. In another example, the time period can be a function of the time period for a subject to clear the aptamers or aptamer conjugates from normal tissue; for example, the time period can be more than the time period for a subject to clear the aptamers or aptamer conjugates from normal tissue, such as more than about an hour, more than about a day, more than about two days, more than about three days, more than about five days, or more than about a week; in another example, the time period can be less than the time period for a subject to clear the aptamers or aptamer conjugates from normal tissue, such as less than about an hour, less than about a day, less than about two days, less than about three days, less than about five days, or less than about a week.

The administered dose of an aptamer or an aptamer conjugate described herein is the amount of the aptamer or the aptamer conjugate that is effective to achieve the desired therapeutic response for a particular patient, composition, and mode of administration, with the least toxicity to the patient or the maximal feasible dose. The effective dosage level can be identified using the methods described herein and depends upon a variety of pharmacokinetic and pharmacodynamic factors including the activity of the particular compositions administered, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. In general, an effective dose of a cancer therapy is the amount of the therapeutic agent which is the lowest dose effective to produce a therapeutic effect. Such an effective dose generally depends upon the factors described above.

Examples of routes of administration include oral administration, rectal administration, topical administration, inhalation (nasal) or injection. Administration by injection includes intravenous (IV), intratumoral (IT), intralesional, peritumoral, intramuscular (IM), and subcutaneous (SC) administration. The compositions described herein can be administered in any form by any effective route, including but not limited to oral, parenteral, enteral, intravenous, intratumoral, intraperitoneal, topical, transdermal (e.g., using any standard patch), intradermal, ophthalmic, (intra) nasally, local, non-oral, such as aerosol, inhalation, subcutaneous, intramuscular, buccal, sublingual, (trans)rectal, vaginal, intra-arterial, and intrathecal, transmucosal (e.g., sublingual, lingual, (trans)buccal, (trans)urethral, vaginal (e.g., trans- and perivaginally), implanted, intravesical, intrapulmonary, intraduodenal, intragastrical, and intrabronchial. In some embodiments, the aptamers or aptamer conjugates described herein are administered orally, rectally, topically, intravesically, by injection into or adjacent to a draining lymph node, intravenously, by inhalation or aerosol, or subcutaneously. In some embodiments, the administration is parenteral administration (e.g., subcutaneous administration). The administration may be an intratumoral injection or a peritumoral injection.

The dosage regimen can be any of a variety of methods and amounts, and can be determined by one skilled in the art according to known clinical factors. As is known in the medical arts, dosages for any one patient can depend on many factors, including the subject's species, size, body surface area, age, sex, immunocompetence, tumor dimensions, general health and specific biomarkers, the particular microorganism to be administered, duration and route of administration, the kind and stage of the disease, for example, tumor size, and other compounds such as drugs being administered concurrently.

The methods of treatment described herein may be suitable for the treatment of a primary tumor, a secondary tumor or metastasis, as well as for recurring tumors or cancers. The dose of the pharmaceutical compositions described herein may be appropriately set or adjusted in accordance with the dosage form, the route of administration, the degree or stage of a target disease, and the like.

In some embodiments, the dose administered to a subject is sufficient to prevent cancer, delay its onset, or slow or stop its progression or prevent a relapse of a cancer, reduce tumor burden, or contribute to the disease-free survival, time to progression or overall survival of the subject. One skilled in the art will recognize that dosage will depend upon a variety of factors including the strength of the particular compound employed, as well as the age, species, condition, and body weight of the subject. The size of the dose will also be determined by the route, timing, and frequency of administration as well as the existence, nature, and extent of any adverse side-effects that might accompany the administration of a particular compound and the desired physiological effect.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. An effective dosage and treatment protocol can be determined by routine and conventional means, starting, e.g., with a low dose in laboratory animals and then increasing the dosage while monitoring the effects, and systematically varying the dosage regimen as well. Animal studies are commonly used to determine the maximal tolerable dose ("MTD") of bioactive agent per kilogram weight. Those skilled in the art regularly extrapolate doses for efficacy, while avoiding toxicity, in other species, including humans.

In accordance with the above, in therapeutic applications, the dosages of the aptamers or aptamer conjugates provided herein may vary depending on the specific aptamer or aptamer conjugate, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and most preferably causing complete regression of the cancer.

Examples of cancers that may treated by methods described herein include, but are not limited to, hematological malignancy, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophilic leukemia, blast cell leukemia, bovine leukemia, chronic myelocytic leukemia, leukemia cutis, embryonal leukemia, cosinophilic leukemia, Gross' leukemia, Rieder cell leukemia, Schilling's leukemia, stem cell leukemia, subleukemic leukemia, undifferentiated cell leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, cpiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma villosum, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, chondrosarcoma, fibrosarcoma, lymphosarcoma, melanosarcoma, myxosarcoma, osteosarcoma, endometrial sarcoma, stromal sarcoma, Ewing's sarcoma, fascial sarcoma, fibroblastic sarcoma, giant cell sarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, rhabdosarcoma, serocystic sarcoma, synovial sarcoma, telangiectaltic sarcoma, Hodgkin's Disease, Non-Hodgkin's Lymphoma, multiple myeloma, neuroblastoma, bladder cancer, breast cancer, ovarian cancer, lung cancer, colorectal cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma subungal melanoma, superficial spreading melanoma, plasmacytoma, colorectal cancer, rectal cancer.

In some embodiments, the methods and compositions provided herein relate to the treatment of a sarcoma. The term "sarcoma" generally refers to a tumor which is made up of a substance like the embryonic connective tissue and is generally composed of closely packed cells embedded in a fibrillar, heterogeneous, or homogeneous substance. Sarcomas include, but are not limited to, chondrosarcoma, fibrosarcoma, lymphosarcoma, melanosarcoma, myxosarcoma, osteosarcoma, endometrial sarcoma, stromal sarcoma, Ewing's sarcoma, fascial sarcoma, fibroblastic sarcoma, giant cell sarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

Additional exemplary neoplasias that can be treated using the methods and compositions described herein include Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, and adrenal cortical cancer.

In some embodiments, the cancer treated is a melanoma. The term "melanoma" is taken to mean a tumor arising from the melanocytic system of the skin and other organs. Non-limiting examples of melanomas are Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma subungal melanoma, and superficial spreading melanoma.

Particular categories of tumors that can be treated using methods and compositions described herein include lymphoproliferative disorders, breast cancer, ovarian cancer, prostate cancer, cervical cancer, endometrial cancer, bone cancer, liver cancer, stomach cancer, colon cancer, colorectal cancer, pancreatic cancer, cancer of the thyroid, head and neck cancer, cancer of the central nervous system, cancer of the peripheral nervous system, skin cancer, kidney cancer, as well as metastases of all the above. Particular types of tumors include hepatocellular carcinoma, hepatoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, pulmonary squamous cell carcinoma, basal cell carcinoma, adenocarcinoma (well differentiated, moderately differentiated, poorly differentiated or undifferentiated), bronchioloalveolar carcinoma, renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pincaloma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

Cancers treated in certain embodiments also include precancerous lesions, e.g., actinic keratosis (solar keratosis), moles (dysplastic nevi), acitinic chelitis (farmer's lip), cutaneous horns, Barrett's esophagus, atrophic gastritis, dyskeratosis congenita, sideropenic dysphagia, lichen planus, oral submucous fibrosis, actinic (solar) clastosis and cervical dysplasia.

Cancers treated in some embodiments include non-cancerous or benign tumors, e.g., of endodermal, ectodermal or mesenchymal origin, including, but not limited to cholangioma, colonic polyp, adenoma, papilloma, cystadenoma, liver cell adenoma, hydatidiform mole, renal tubular adenoma, squamous cell papilloma, gastric polyp, hemangioma, osteoma, chondroma, lipoma, fibroma, lymphangioma, leiomyoma, rhabdomyoma, astrocytoma, nevus, meningioma, and ganglioneuroma.

In certain embodiments, the cancer is a solid tumor (e.g., breast cancer, head and neck squamous cell carcinoma, adenoid cystic carcinoma, bladder cancer, pancreatic cancer, hepatocellular carcinoma, melanoma, merkel cell carcinoma, or a colorectal carcinoma). In some embodiment, the solid tumor is accessible for intratumoral administration. In certain embodiment, the cancer is a sarcoma (e.g., soft tissue sarcoma). In certain embodiments, the cancer is a hematologic cancer (e.g., a lymphoma).

Treatment of Immune Disorders

In certain embodiments, the aptamers provided here can inhibit immune responses by blocking T cell activation. In some aspects, provided herein are methods of treating autoimmune or inflammatory diseases and/or inhibiting transplant rejection comprising the administering to a subject a pharmaceutical composition comprising one or more aptamers provided herein.

The methods described herein can be used to treat any subject in need thereof. As used herein, a "subject in need thereof" includes any subject that has an inflammatory disease, an immune disorder, and/or who has received an organ and/or tissue transplant, as well as any subject with an increased likelihood of acquiring a such a disease or disorder or receiving such a transplant.

The pharmaceutical compositions described herein can be used, for example, as a pharmaceutical composition for preventing or treating (reducing, partially or completely, the adverse effects of) inflammation associated with an autoimmune disease, such as chronic inflammatory bowel disease, systemic lupus erythematosus, psoriasis, muckle-wells syndrome, rheumatoid arthritis, multiple sclerosis, or Hashimoto's disease; an allergic disease, such as a food allergy, pollenosis, or asthma; an infectious disease, such as an infection with *Clostridium difficile*; an inflammatory disease such as a TNF-mediated inflammatory disease (e.g., an inflammatory disease of the gastrointestinal tract, such as pouchitis, a cardiovascular inflammatory condition, such as atherosclerosis, or an inflammatory lung disease, such as chronic obstructive pulmonary disease); a pharmaceutical composition for suppressing rejection in organ transplantation or other situations in which tissue rejection might occur; a supplement, food, or beverage for improving immune functions; or a reagent for suppressing the proliferation or function of immune cells.

In some embodiments, the methods provided herein are useful for the treatment of inflammation. In certain embodiments, the inflammation of any tissue and organs of the body, including musculoskeletal inflammation, vascular inflammation, neural inflammation, digestive system inflammation, ocular inflammation, inflammation of the reproductive system, and other inflammation, as discussed below.

The pharmaceutical compositions described herein can be used, for example, as a pharmaceutical composition for preventing or treating (reducing, partially or completely, the adverse effects of) inflammation associated with an immune disorder of the musculoskeletal system. Immune disorders of the musculoskeletal system include, but are not limited to, those conditions affecting skeletal joints, including joints of the hand, wrist, elbow, shoulder, jaw, spine, neck, hip, knew, ankle, and foot, and conditions affecting tissues connecting muscles to bones such as tendons. Examples of such immune disorders, which may be treated with the methods and compositions described herein include, but are not limited to, arthritis (including, for example, osteoarthritis, rheumatoid arthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic).

The pharmaceutical compositions described herein can be used, for example, as a pharmaceutical composition for preventing or treating (reducing, partially or completely, the adverse effects of) inflammation associated with an ocular immune disorder. Ocular immune disorders refers to an immune disorder that affects any structure of the eye, including the eyelids. Examples of ocular immune disorders which may be treated with the methods and compositions described herein include, but are not limited to, blepharitis, blepharochalasis, conjunctivitis, dacryoadenitis, keratitis, keratoconjunctivitis sicca (dry eye), scleritis, trichiasis, and uveitis The pharmaceutical compositions described herein can be used, for example, as a pharmaceutical composition for preventing or treating (reducing, partially or completely, the adverse effects of) inflammation associated with nervous system immune disorders. Examples of nervous system immune disorders which may be treated with the methods and compositions described herein include, but are not limited to, encephalitis, Guillain-Barre syndrome, meningitis, neuromyotonia, narcolepsy, multiple sclerosis, myelitis and schizophrenia.

The pharmaceutical compositions described herein can be used, for example, as a pharmaceutical composition for preventing or treating (reducing, partially or completely, the adverse effects of) inflammation associated with the vasculature or lymphatic system. Examples of inflammation of the vasculature or lymphatic system which may be treated with the methods and compositions described herein include, but are not limited to, arthrosclerosis, arthritis, phlebitis, vasculitis, and lymphangitis.

The pharmaceutical compositions described herein can be used, for example, as a pharmaceutical composition for preventing or treating (reducing, partially or completely, the adverse effects of) inflammation associated with digestive system immune disorders. Examples of digestive system immune disorders which may be treated with the methods and pharmaceutical compositions described herein include, but are not limited to, cholangitis, cholecystitis, enteritis, enterocolitis, gastritis, gastroenteritis, inflammatory bowel disease, ileitis, and proctitis. Inflammatory bowel diseases include, for example, certain art-recognized forms of a group of related conditions. Several major forms of inflammatory bowel diseases are known, with Crohn's disease (regional bowel disease, e.g., inactive and active forms) and ulcerative colitis (e.g., inactive and active forms) the most common of these disorders. In addition, the inflammatory bowel disease encompasses irritable bowel syndrome, microscopic colitis, lymphocytic-plasmocytic enteritis, coeliac disease, collagenous colitis, lymphocytic colitis and cosinophilic enterocolitis. Other less common forms of IBD include indeterminate colitis, pseudomembranous colitis (necrotizing colitis), ischemic inflammatory bowel disease, Behcet's disease, sarcoidosis, scleroderma, IBD-associated dysplasia, dysplasia associated masses or lesions, and primary sclerosing cholangitis.

The pharmaceutical compositions described herein can be used, for example, as a pharmaceutical composition for preventing or treating (reducing, partially or completely, the adverse effects of) inflammation associated with reproductive system immune disorders. Examples of reproductive system immune disorders which may be treated with the methods and pharmaceutical compositions described herein include, but are not limited to, cervicitis, chorioamnionitis, endometritis, epididymitis, omphalitis, oophoritis, orchitis, salpingitis, tubo-ovarian abscess, urethritis, vaginitis, vulvitis, and vulvodynia.

The methods and pharmaceutical compositions described herein may be used to treat autoimmune conditions. Such conditions include, but are not limited to, acute disseminated alopecia universalise, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, type 2 diabetes, giant cell arteritis, goodpasture's syndrome, Grave's disease, Guillain-Barre syndrome, Hashimoto's disease, Henoch-Schonlein purpura, Kawasaki's disease, lupus erythematosus, microscopic colitis, microscopic polyarteritis, mixed connective tissue disease, Muckle-Wells syndrome, multiple sclerosis, myasthenia gravis, opsoclonus myoclonus syndrome, optic neuritis, ord's thyroiditis, pemphigus, polyarteritis nodosa, polymyalgia, rheumatoid arthritis, Reiter's syndrome, Sjogren's syndrome, temporal arteritis, Wegener's granulomatosis, warm autoimmune haemolytic anemia, interstitial cystitis, Lyme disease, morphea, psoriasis, sarcoidosis, scleroderma, ulcerative colitis, and vitiligo.

The methods and pharmaceutical compositions described herein may be used to treat T-cell mediated hypersensitivity diseases. Such conditions include, but are not limited to, contact hypersensitivity, contact dermatitis (including that due to poison ivy), uticaria, skin allergies, respiratory allergies (hay fever, allergic rhinitis, house dustmite allergy) and gluten-sensitive enteropathy (Celiac disease).

Other immune disorders which may have an inflammatory component and may be treated with the methods and pharmaceutical compositions include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonoitis, pharyngitis, pleuritis, pneumonitis, prostatistis, pyelonephritis, and stomatisi, transplant rejection (involving organs such as kidney, liver, heart, lung, pancreas (e.g., islet cells), bone marrow, cornea, small bowel, skin allografts, skin homografts, and heart valve xengrafts, sewrum sickness, and graft vs host disease), acute pancreatitis, chronic pancreatitis, acute respiratory distress syndrome, Sexary's syndrome, congenital adrenal hyperplasis, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensistivity reactions, allergic conjunctivitis, keratitis, herpes zoster ophthalmicus, iritis and oiridocyclitis, chorioretinitis, optic neuritis, symptomatic sarcoidosis, fulminating or disseminated pulmonary tuberculosis chemotherapy, idiopathic thrombocytopeniaurpura in adults, secondary thrombocytopenia in adults, acquired (autoimmune) haemolytic anemia, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis, Type 1 diabetes, asthma, inflammatory bowel disease, systemic lupus erythematosus, psoriasis, chronic obstructive pulmonary disease, and inflammation accompanying infectious conditions (e.g., sepsis).

EXAMPLES

Example 1-Materials and Methods for Examples 2-3

A. Materials a. Random library

Random library 9.0 ("Lib 9.0") was purchased from IDT. The library contains a vast repertoire of approximately $10^{15}$ different 40 nt-long random sequences flanked by two 20 nt unique sequences at the 3' and 5' acting as a primer for PCR amplification during the SELEX procedure. The lyophilized library was reconstituted in ultra-pure water (UPW) to a final concentration of 1 mM. The random library sequence was: 5'-TCACTATCGGTCCAGACGTA-40N-TATTGCGCCGAGGTTCTTAC-3' (SEQ ID NO: 23), where N represents a random oligonucleotide selected from a mixture of equally represented T, A, C, and G nucleotides (1:1:1:1 ratio).

Pre-SELEX Preparation:

Following reconstitution, the library underwent QC validation for size exclusion using HPLC ProSEC 300S column (Agilent).

b. Library Primers and Caps

A set of 20 nt primers and caps were purchased from IDT (Table 4). Caps were used to hybridize to the Library's primer sites during incubation with cells in order to refrain from the possibility of primer sequences interacting with the random 40 nt sequence site. A mixture of 3' and 5' caps (Table 4) in each SELEX round was used in a 3:1 caps-to-library ratio.

The forward primer was purchased from IDT labelled with Cy-5 at the 5' site for sequence amplification that was detected in a fluorescence assay. The lyophilized primers were reconstituted in ultra-pure water (UPW) to a concentration of 100 μM.

TABLE 4

Random library, primers and caps sequences

| Auxiliary sequences | SEQ ID NO: | Sequence 5' to 3' |
|---|---|---|
| Random Library | 23 | TCACTATCGGTCCAGACGTA-40N-TATTGCGCCGAGGTTCTTAC |
| Forward Primer | 24 | TCACTATCGGTCCAGACGTA |
| Forward labeled Cy-5 | 25 | /Cy5/TCACTATCGGTCCAGACGTA |
| Reverse/3' cap | 26 | GTAAGAACCTCGGCGCAATA |
| 5' cap | 27 | TACGTCTGGACCGATAGTGA | c. Aptamer Folding Buffer

Phosphate-buffered saline (minus Magnesium and Calcium) was supplemented with 1 mM Magnesium Chloride ($MgCl_2$). The folding buffer was sterilized with PVDF membrane filter unit 0.22 μm and kept at 4° C.

d. PBMC

PBMC were isolated using Ficoll (Lymphoprep, Axis-Shield) density gradient centrifugation following the manufacturer's protocol.

Frozen Cynomolgus Monkey PBMCs (NHP-PC001) were purchased from Creative Biolabs.

e. Human PanT and B cell isolation of human Pan T cells was performed by using Pan T cells isolation kit (Miltenyi Biotec, 130-096-535) following the manufacturer's protocol. Isolation of human Pan B cells was performed by using Pan B cells isolation kit (Miltenyi Biotec, 130-101-638) following the manufacturer's protocol f. Antibodies, Proteins and Enzymes αCD3&-FITC (Cat. #130-113-690)/APC (Cat. #130-113-687)/VioBlue (Cat. #130-114-519)/APC-Vio770 (Cat. #130-113-688), αCD4-FITC (Cat. #130-114-531), αCD8-FITC (Cat. #130-113-719)/PE-Vio770 (Cat. #130-113-159) and matching isotype controls were purchased from Miltenyi Biotech. αCD38 OKT3 clone (Cat. #317302) was purchased from BioLegend.

Recombinant Human CD3 epsilon protein (Fc Chimera His Tag) (ab220590), Recombinant Cynomolgus CD3 epsilon protein (Fc Chimera His Tag) (ab220531), and Recombinant Mouse CD3 epsilon protein (His tag) (ab240841) where purchased from Abcam. Human IgG1 isotype was used as a negative counter selection (InVivoMAb, BE0297). Protein G magnetic beads purchased from ThermoFisher (88847).

Herculase II Fusion DNA Polymerase (600675) that is used for Asymetric PCR (A-PCR) purchased from Agilent and real-time-PCR iTaq Universal SYBRGreen Supermix (1725124) purchased from BIO-RAD.

g. Cell-Lines

Jurkat, Daudi and Kasumi-1 cell-lines were purchased from ATCC. Jurkat cell (ATCC TIB-152), Daudi cells (ATCC CCL-213) and Kasumi-1 (ATCC CRL-2724) were grown in RPMI-1640 supplemented with 10% fetal calf serum (FCS) and 1% Penicillin and streptomycin (Pen/Strep). All cells were cultured at 37° C. and 5% CO2.

g. Aptamers

Each aptamer was diluted to the desired concentration with the folding buffer. The aptamers were heated for 5 minutes at 95° C., followed by a rapid cooling for 10 minutes on ice, and room temperature (RT) incubation for 10 minutes. Folded aptamer was then added to the medium-suspended cells.

Lyophilized aptamers were kept in dark at RT until reconstituted in PBS-supplemented with 1 mM $MgCl_2$ to a concentration of 100 UM and stored at −20° C. in the dark.

B. Experimental Methods a. Binding SELEX Protocol

The binding SELEX was conducted for 11 sequential rounds using CD38-Fc protein coupled to protein G magnetic beads (Positive selection), IgG1 protein coupled to protein G magnetic beads or with beads only (Negative selections, starting from round 3 onwards).

A. Beads-Protein Complex Preparation

Magnetic protein G beads were vortexed and washed once with PBS and then mixed with 100 ul of protein for 10 min at RT under gentle shaking condition. Then, the beads were separated by a magnet, the supernatant was discarded and the beads re-suspended with 350 ul of Folding buffer×1 containing 2% BSA.

For verification of the beads-protein complex formation, a small sample (before DNA added) was treated with FC-blocker (Miltenyi), stained with αCD3ε and analysed by flow cytometry B. Initial Library and Enriched Round Library Preparation and Folding Protocol The library is initially reconstituted to 1 mM. Working concentration in the first round was 14.3 μM, while in rounds 2-11, a concentration of 0.25-0.5 UM of enriched library was used. For each round the following components were used:

TABLE 5

Calculating library concentrations

| Component | Concentration | Calculation |
|---|---|---|
| Enriched library | 0.25-0.5 μM | $C_{\mu M} = \dfrac{C_{\frac{ng}{\mu l}} \times 1{,}000}{330 \text{ gr/mole} \times [90 \text{ nt}(lib \text{ length})]}$ |
| | | $C_{\mu M} \times V_{Elution} = [0.2 \text{ up to } 0.5]\,\mu M \times V_{pool}$ |
| Mix caps 5' + 3' | 50 uM | $\dfrac{V_{Elution} \times C_{Elution}}{50\,\mu M} \times 3 = V_{mix\,caps}$ |
| Folding buffer | X0 | $\dfrac{V_{Elution} \times V_{mix\,caps}}{9} = V_{FBX10}$ |
| Folding buffer | X1 | Adjust volume to 350 ul |

The libraries underwent DNA folding per the following protocol: were heated for 5 minutes at 95° C., followed by a rapid cooling for 10 minutes on ice, and maintained until use at 4° C.

C. SELEX

Once the enriched library was folded, 350 ul of enriched library rounds was added to 350 ul of CD3ε-FC-bead (positive selection rounds 1-11) or to Beads only/IgG$_1$-beads complex (counter selection, rounds 3-11). Incubation time, protein amount and wash steps varied by the SELEX rounds.

In positive selection, the supernatant, "unbound to positive" fraction, was removed kept at −20° C. until NGS preparation. For washes, the beads were precipitated with a magnet, the supernatant was discarded and the beads were re-suspended with 1 ml of folding buffer×1. After the washing step, the beads suspend in 300 ul ultra-pure water (UPW) and the DNA eluted at 95° C. for 10 min. Finally, the beads precipitated with magnet, and supernatant "bound to positive" was collected for the PCR stage.

If a negative SELEX round was implemented, than the 350 ul of enriched library rounds was added to 350 ul of beads only/IgG beads complex and the supernatant collected fractions proceeded to positive selection stage. The binding fraction to the negative samples, called "bound to negative", were eluted and kept at −20° C. until NGS preparation.

D. PCR Amplification Protocol

The eluted DNA fractions ("bound" and "unbound") were used, each, as a template for Asymmetrical PCR (A-PCR) amplification. The PCR reaction was modulated for each round. The PCR components and the amplification protocol are shown in table 6 and table 7, respectively.

TABLE 6

PCR components

| Reagent | Stock | Volume |
|---|---|---|
| UPW | | Adjust to reaction final volume |
| Buffer | x5 | x1 |
| dNTPs mix | 10 mM | 0.8 mM |
| Forward primer | 10 μM | 2.5 uM |
| Reverse primer | 10 μM | 0.25 uM |
| Template | | 15% |
| DNA polymerase enzyme | | 1% |

TABLE 7

PCR amplification protocol for enriched library

| Number of cycles | Temperature | Duration |
|---|---|---|
| 1 | 95° C. | 3 min |
| 18-36 | 95° C. | 30 sec |
| | 58° C. | 30 sec |
| | 72° C. | 30 sec |
| Final | 4° C. | ∞ |

E. PCR ssDNA Purification

The PCR products were concentrated with 10K Amicon (Millipore, UFC5010BK) and purified using HLPC ProSEC 300S size exclusion column (Agilent). After purification, the DNA underwent buffer exchange with ssDNA clean kit (ZYMO, D7011), concentration was measured using Nano-Drop and the DNA was diluted for a new SELEX round.

b. Assessment of Library Pools Binding to Target Protein by Real-Time-PCR

Magnetic protein G beads were vortexed and washed once with PBS and then re-suspended with protein (CD38 or IgG1) for 10 min at RT under gentle shaking condition. Then, the beads were precipitated under the magnetic field, the supernatant was discarded and the beads re-suspended with 125 ul of Folding buffer×1 and 2% BSA. Next, the library pools from rounds 3, 6, 9, 11, and the initial random library were folded (95° C. 5 min, ice 10 min, and maintenance at 4° C.). 125 ul of each of the folded DNA libraries was mixed with the beads-protein complex for 1 hr at 4° C. in a gentle shaking. After incubation, the beads were precipitated with a magnet and washed 3 times with 1 ml folding buffer. Finally, the DNA binding fraction was eluted at 95° C. with 100 ul UPW for 10 min and subsequently used as a template in real-time-PCR with SYBRGreen Supermix (BIO-RAD).

c. Assessment of Individual Aptamers Binding to Target Protein Protein-Aptamers Binding Assay by HPLC 1 μM of folded Cy5 labeled aptamer was mixed with 5 μM of protein to a final volume of 60 ul and incubated for 1 hr at 4° C. or 37° C. Next, to detect the Cy-labelled aptamers, samples were analyzed at 570 nm absorption via HPLC ProSEC 300S size exclusion column (Agilent).

d. Assessment of Individual Aptamers Binding to Cells by with Flow Cytometry 0.5-2×10$^6$ cells (isolated Pan T cells, B cells, hPBMCs, Cynomolgus PBMCs, Jurkat, and Daudi) were washed and re-suspended in 0.2-1.ml folding buffer that contains 0.1% BSA and 0.01% tRNA.

0.25-1.25 μM of single DNA candidate were fluorescently labelled by mixing with CpG'-Cy5 tag (1:1 ratio) and folded (95° C. 5 min, ice 10 min, and maintenance at 4° C.). Next, the labelled DNA aptamers were incubated with the cells for 1 hr at 4° C. or 37° C. in V shape 96 well plate under gentle shaking conditions (hPBMCs and Cyno PBMCS were added αCD8/αCD4 in the final 15 min of incubation). After incubation, cells were washed 3 times with folding buffer×1 and analysed after each wash using flow cytometry (Cyto-Flex).

e. Competitive CD3 epsilon epitopes binding assay 0.25× $10^6$ Jurkat cells were washed once, re-suspended in folding buffer×1 containing 0.1% BSA and 0.01% tRNA and incubated for 15 min with 1:20 dilution of αCD3 clone OKT3 (BioLegend, 317302) or αCD3 clone REA613 (Miltenyi, 130-114-519) or with buffer. Next, 0.25 µM of folded Cy5 labelled aptamers were incubated with the cells for 1 hr at 37° C. under gentle shaking condition. After incubation, cells were washed 3 times with folding buffer×1 and analysed after each wash using flow cytometry (CytoFlex).

f. CS6 Effective Concentration 50 (EC50) Quantification $5×10^4$ Jurkat cells were washed and re-suspended in ×1 folding buffer that contain 0.1% BSA and 0.01% tRNA. 0.1-80 nM of CS6 aptamer were labelled with CpG'-Cy5 tag (1:1 ratio) and folded (950 C 5 min, ice 10 min, and maintenance at 40 C). Next, the DNA aptamers were mixed with the cells and incubated for 1 hr at 370 C in V shape 96 well plate under gentle shaking conditions. After incubation, the cells were washed twice with folding buffer×1 and analysed via flow cytometry (CytoFlex).

Example 2-Identification of CD3-Targeting Aptamer Via Binding SELEX

Selection of the CD3 binding aptamers was described herein. The T cell targeting aptamers were identified via Binding SELEX and Hybrid Binding Cell-SELEX using recombinant CD3e protein and recombinant protein plus T cells, respectively. The final lead was characterized for its binding to the target protein and T-Cells.

This disclosure describes the identification and characterization of the T cell engaging aptamers from a random library of $10^{15}$ potential aptamers using the SELEX methodology in a novel application. This aptamer moiety, as part of the bispecific therapeutic entity was designed to be constant across different patients.

Figure 1B:
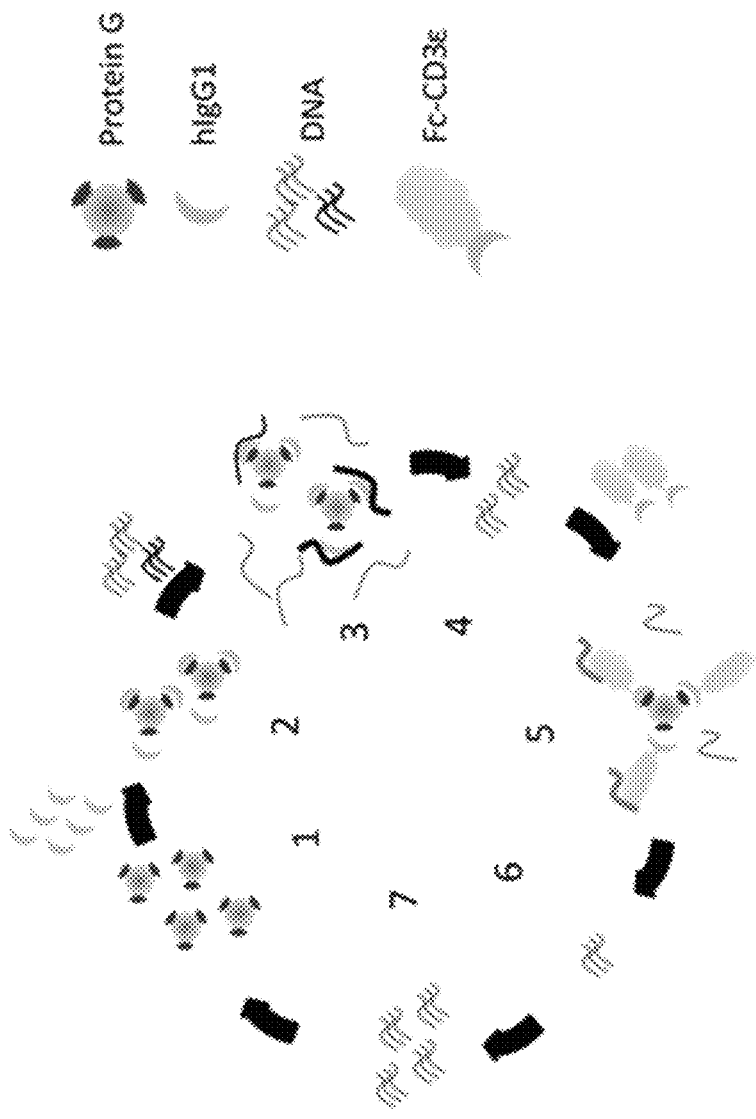

Binding SELEX was conducted using recombinant Human CD3 epsilon protein Fc chimera for a total of eleven (11) rounds. For counter negative selection, either beads only (rounds 1-6) or beads conjugated to Human IgG1 (rounds 7-11) were used in order to rid of all aptamers which bind non-specifically to the magnetic beads or to the Fc component of the recombinant protein (FIG. 1). After round 11 of the SELEX, enriched aptamer libraries are subjected to sequencing and analysis via specific algorithm. Single candidates are identified and undergo verification.

Figure 2A:
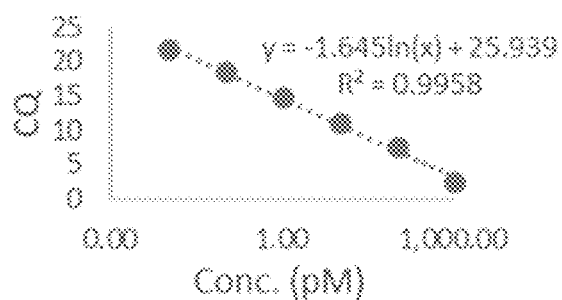
FIGS. 2A and 2B show the binding SELEX comparative assay. Binding assay was performed on target protein CD3ε-beads complex (black) or control protein IgG1 (gray) with initial random library (Rnd Lib) and library enriched pools from Rounds 3(R3), 6(R6), 9(R9), and 11(R11). Post incubation and wash the library DNA was eluted and concentration in the supernatant was evaluated via real-time-PCR. The standard curve was performed with a random library (top). (B) Binding of Cy5 fluorescently labeled libraries to Jurkat T cell line and to Pan B cells was demonstrated by flow cytometry. Dot plots and histogram graphs are shown. Flow data quantification of Cy5 median fluorescence intensity (MFI).
Figure 2A:
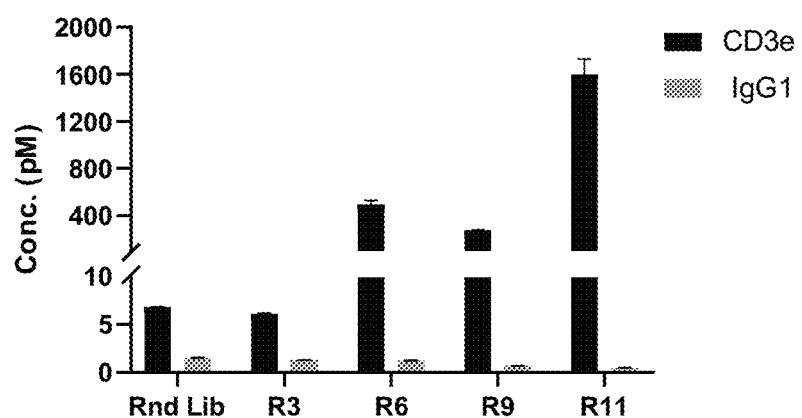

FIG. 1.B depicts the SELEX stages: counter selection starts with protein G magnetic beads (1) that are conjugated to IgG1 (2) and incubated with DNA aptamer library pool from the previous stage (3). Next, unbound DNA aptamers are collected for positive selection (4) and are incubated with FC-CD3ε-conjugated beads (5) here, the bound fraction (6) undergoes PCR amplification and HPLC purification for the next round 1. SELEX Rounds Comparative Assay Original random library 'No. 9.0' and library pools eluted from rounds 3, 6, 9 and 11 were tested for their binding to hCD38. Each round was amplified by PCR using 5' primer labelled with Cy-5 following incubation with Beads-Fc-CD38 complex for 1 hr at 4° C. As a negative control, the variant pools where incubate with Beads-IgG1 complex (FIG. 2A). The amount of amplified DNA, which was precipitated with the target protein, was found much higher in libraries from rounds 6, 9 and 11 than in the random initial library used in the binding SELEX. The results showed specific and strong enrichment as of round six compared with the initial library. Further, there was another increment in the specific binding observed in round 11.

Figure 2B:
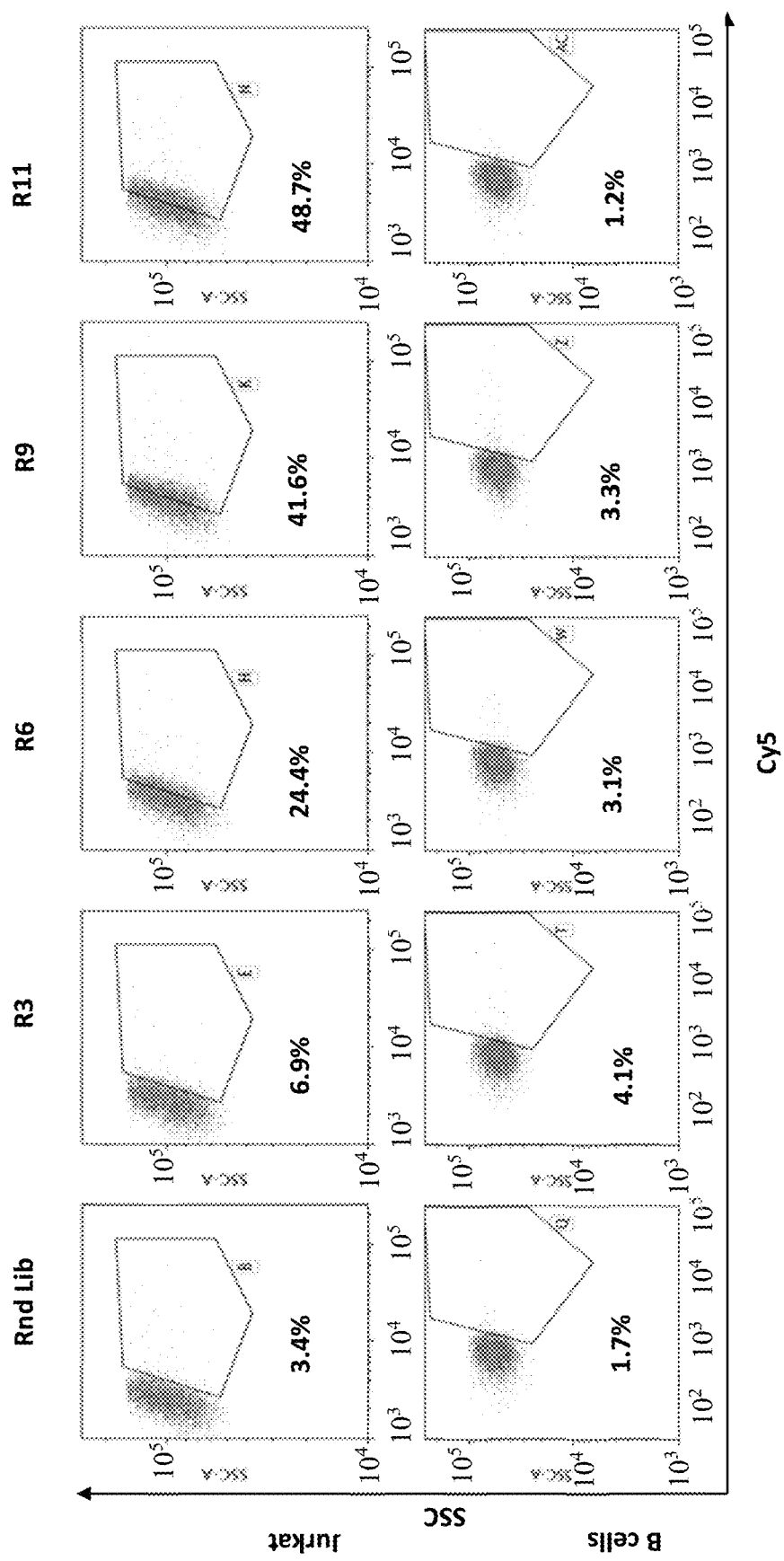
Figure 2B:
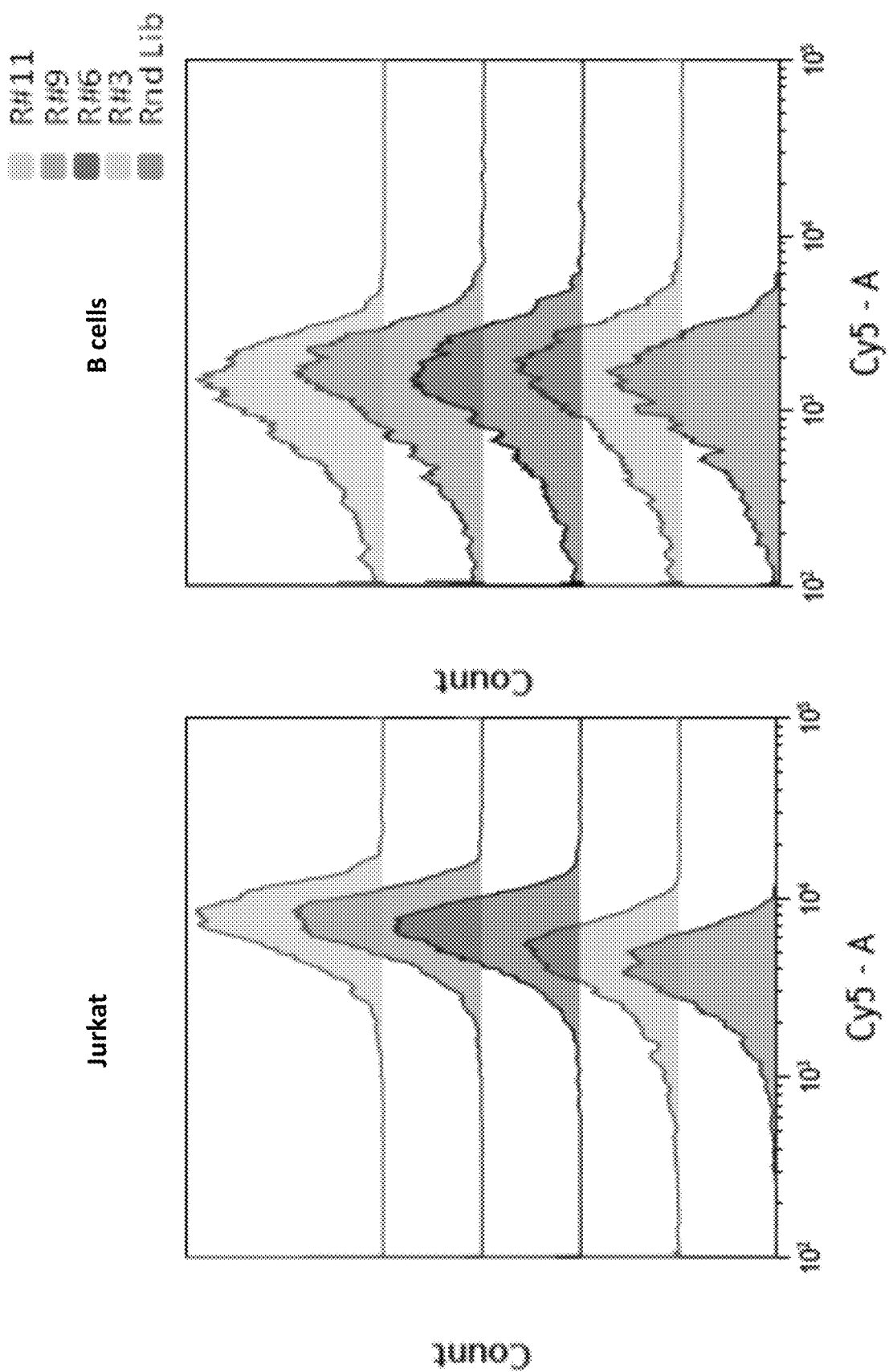
Figure 2B:
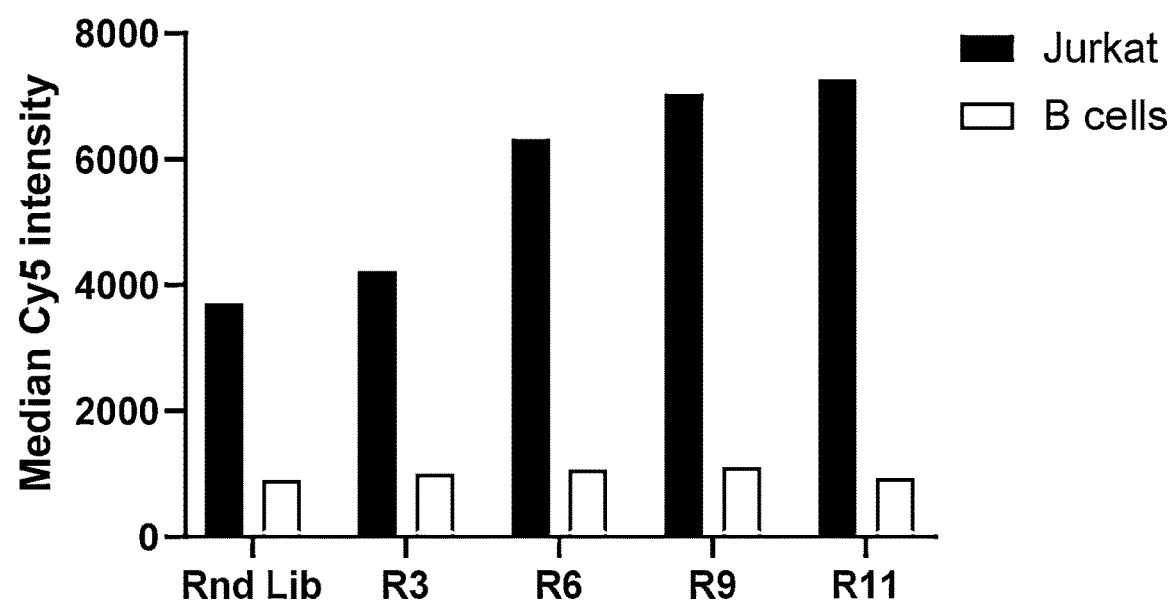

After demonstrating round-to-round enrichment using the recombinant CD3 protein, we tested whether such enrichment is observed also in a whole-cell context. Jurkat T cells were incubated with the same Cy5 tagged library pools, washed, and analysed by flow cytometry. As a negative control, isolated Pan B cells were used (FIG. 2B.).

Similarly to the protein data, a specific and strong round-to-round enrichment for the target cells was demonstrated.

2. NGS Results

Enriched libraries eluted in rounds 8, 9, 10 and 11 ("bound"), as well as the supernatant of positive selection rounds ("unbound"), were subjected to sequencing using the high-throughput NGS Illumina NextSeq500.

Post sequencing, the data was analyzed via an algorithm which allocated single candidates for downstream binding assays. The algorithm utilizes statistical estimators, tests, and metrics.

Figure 3A:
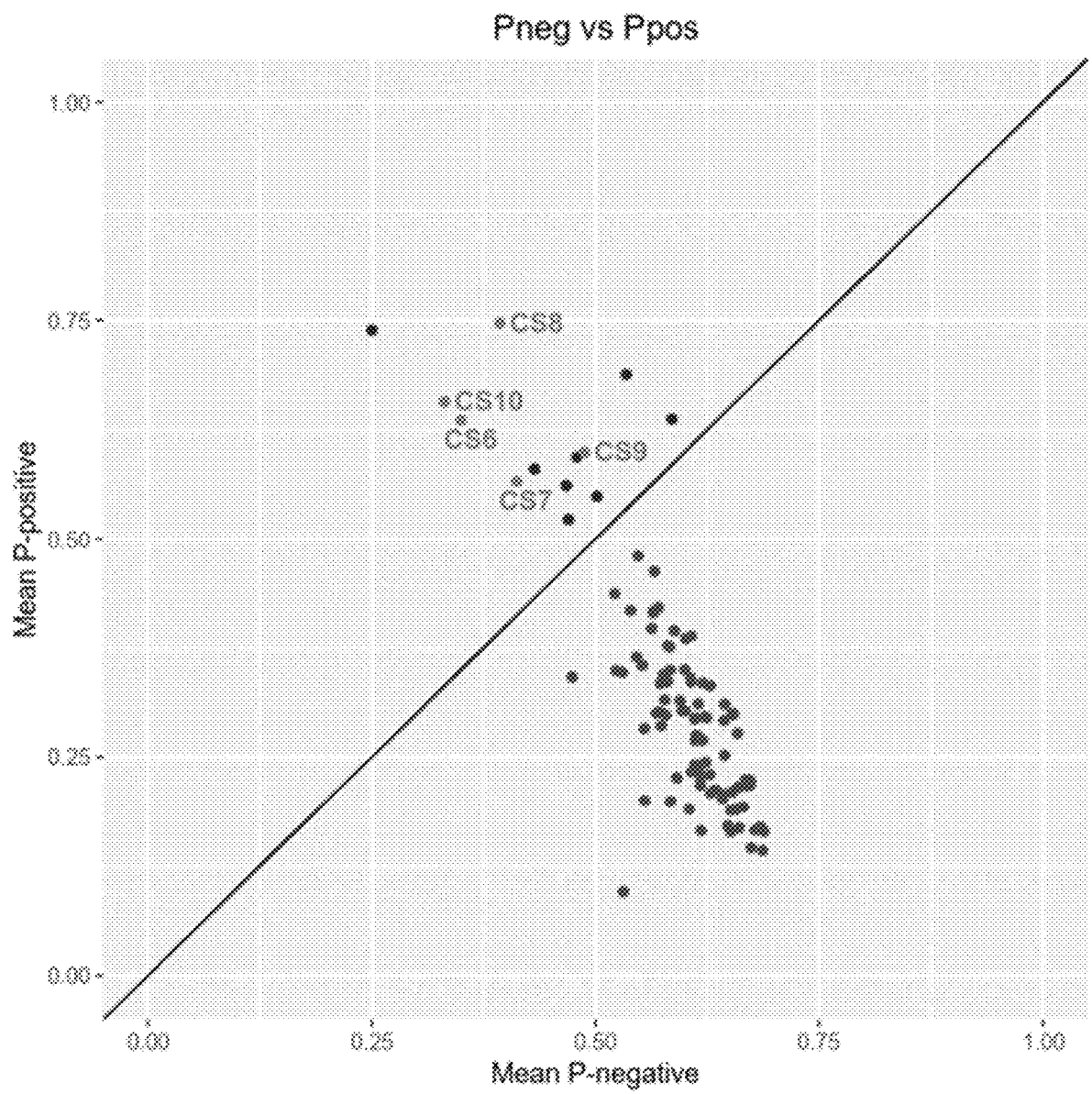
FIGS. 3A-3C show next generation sequencing (NGS) analysis results.

The mean P-positive and P-negative scores of the top 100 most abundant aptamers in the last round, were plotted (FIG. 3A), and aptamers with significant bound to unbound ratio as described above in #6 (p<0.05; Poisson test, consistent in all rounds) were highlighted and selected for experimental validations (termed CD3-CS6-9, ID SEQ NO 1-5). The additional 9 aptamers with high mean P-positive values (P-positive >0.5) were assigned an identifier (CD3_Ppos10-18 ID SEQ NO. 6-14)). The identified CD3 binding aptamers are listed in Table 8

TABLE 8

CD3-binding aptamers

| Aptamer name | SEQ ID NO: | Sequence 5' to 3' |
|---|---|---|
| CS6 | 1 | ATCGTATAAGGGCTGCTTAGGATTGCGATAATACGGTCAA |
| CS7 | 2 | CATTTCATAGGGCTGCTTAGGATTGCGAAGGTAATGCCAG |
| CS8 | 3 | CCCTTACCCCTTTTAGGTCTGCTTAGGATTGCGAAAAAAG |
| CS9 | 4 | TTGTAAGGACTGCTTAGGATTGCGAAAACAATATTCGTAT |
| CS8c | 5 | CTTTTAGGTCTGCTTAGGATTGCGAAAAAAG |
| Ppos 10 | 6 | TCCATGGGTCTGCTCTAGGATTGCGTTCATGGTCTCCCCG |
| Ppos 11 | 7 | AATTACAACCTTGGATTGCAAAGGGCTGCTGTGTTGTTTA |
| Ppos 12 | 8 | ATCGGAGCTGTTCCTTGATACCGATTCAAAAAGTTCGTAC |
| Ppos 13 | 9 | AATTTGTAGGGACTGCTCAGGATTGCGGATACAAATTAAT |
| Ppos 14 | 10 | AGACATTGGGGACTGCTCGGGATTGCGAATCTATGTCTCC |

TABLE 8-continued

CD3-binding aptamers

| Aptamer name | SEQ ID NO: | Sequence 5' to 3' |
|---|---|---|
| Ppos 15 | 11 | CCCTTTTTTAACTAGGTCTGCTTAGGATTGC GAATGTTAA |
| Ppos 16 | 12 | ACCTCAAAAGCGCGGGCTGCTCAAAGGATTG CGTAGCTTT |
| Ppos 17 | 13 | GGGGGTTAAGGGCTGCTTAGGATTGCGATAA TACGGTCAA |
| Ppos 18 | 14 | AACATATAACTGCTCAATAATATAGATAAAA TACTCACAA |

Figure 3B:
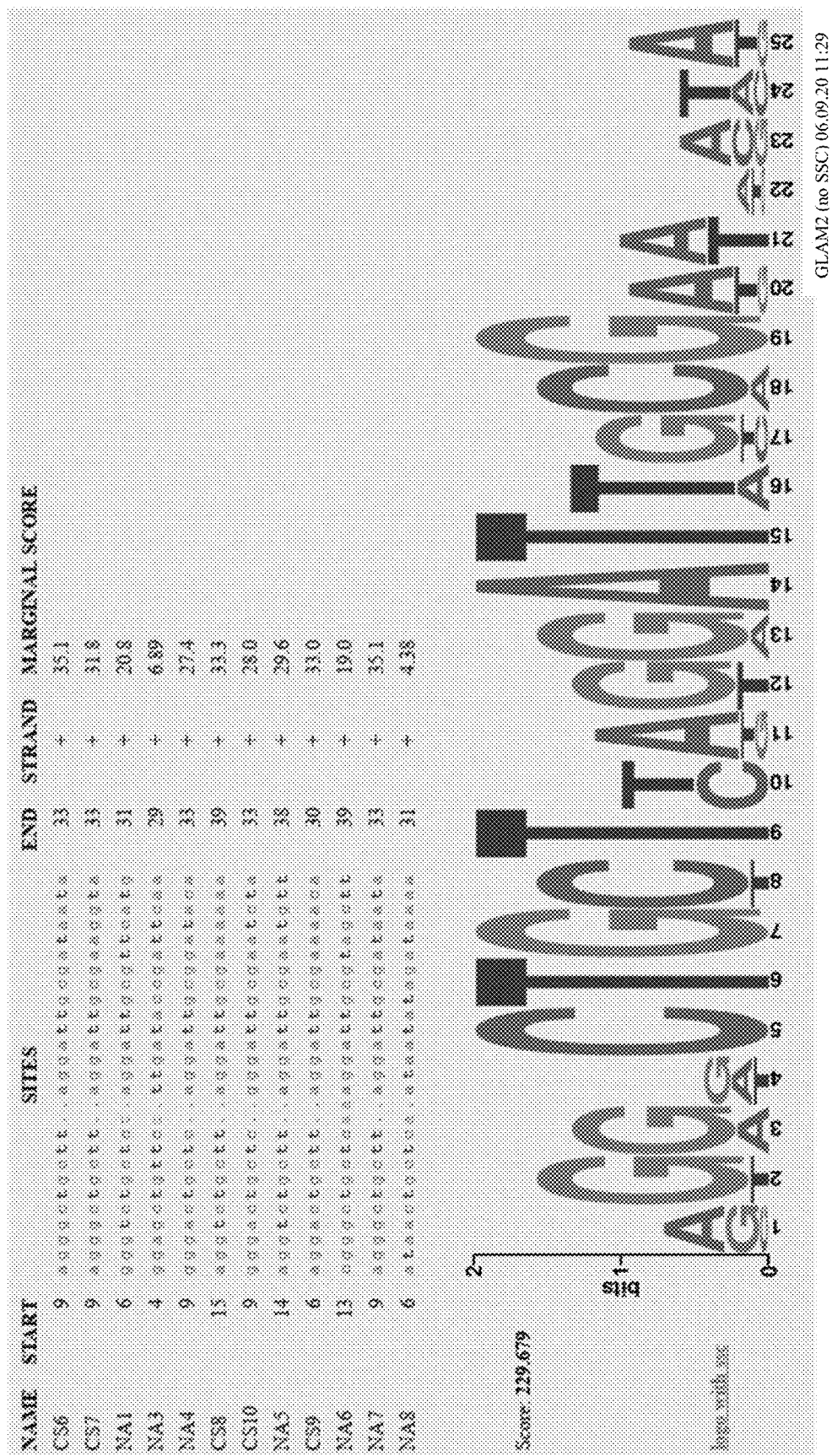
Figure 3B:
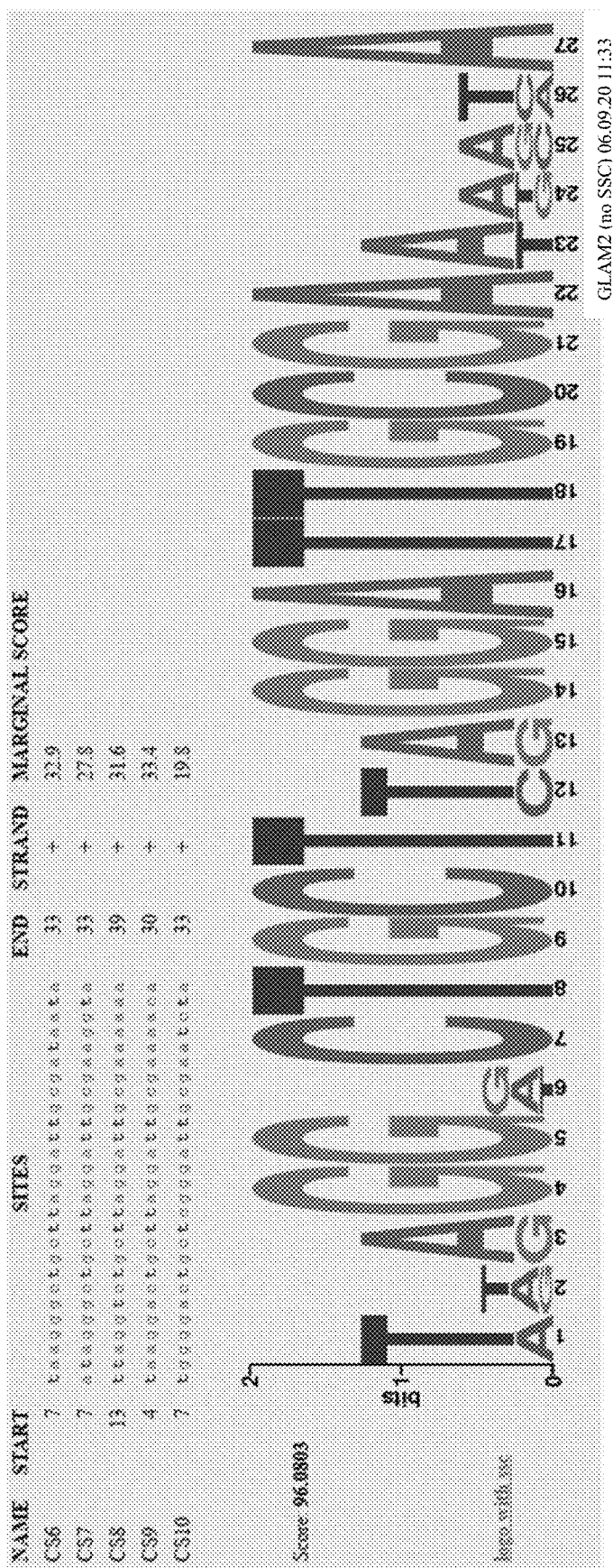
Figure 3C:
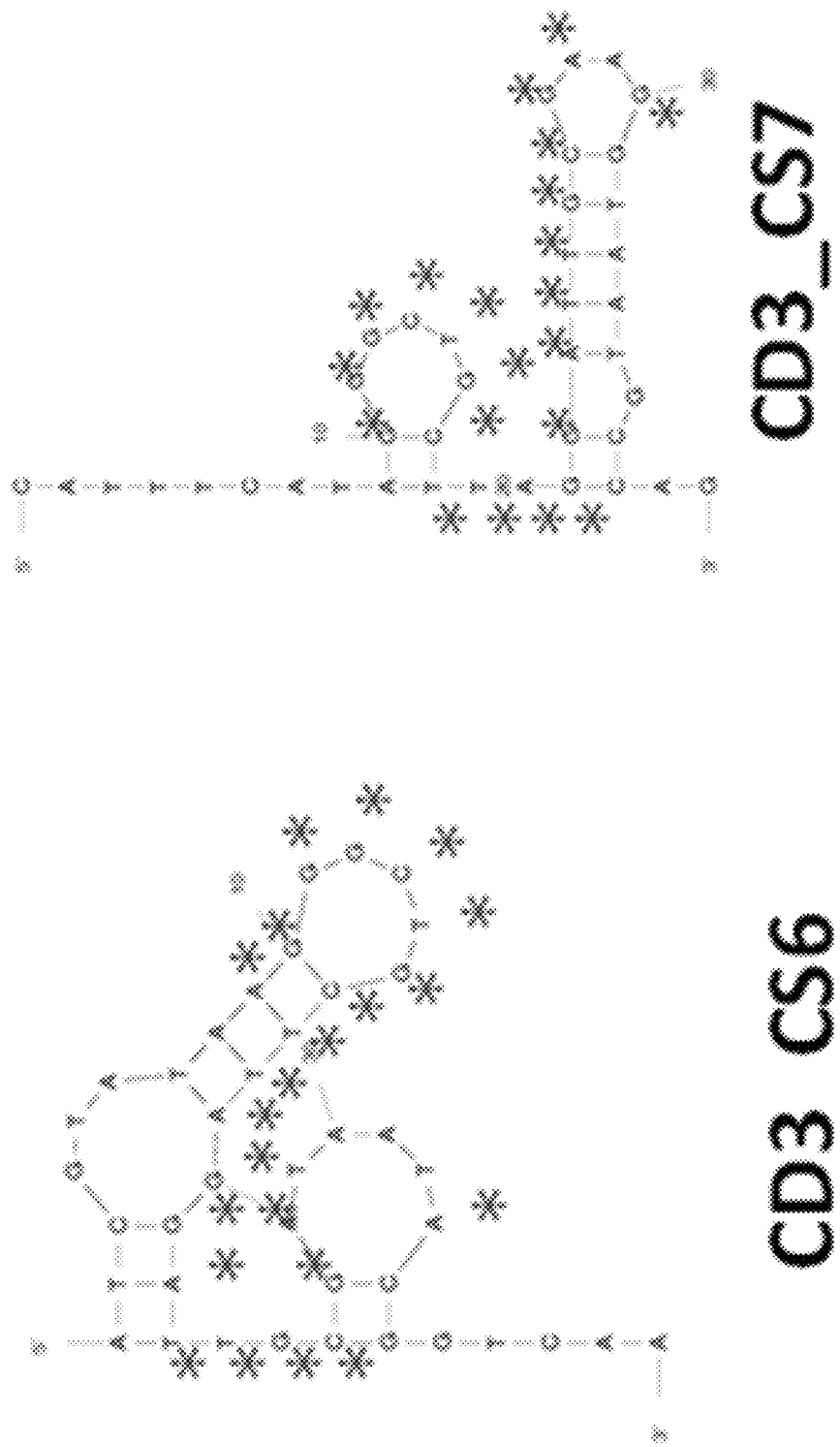
Figure 3C:
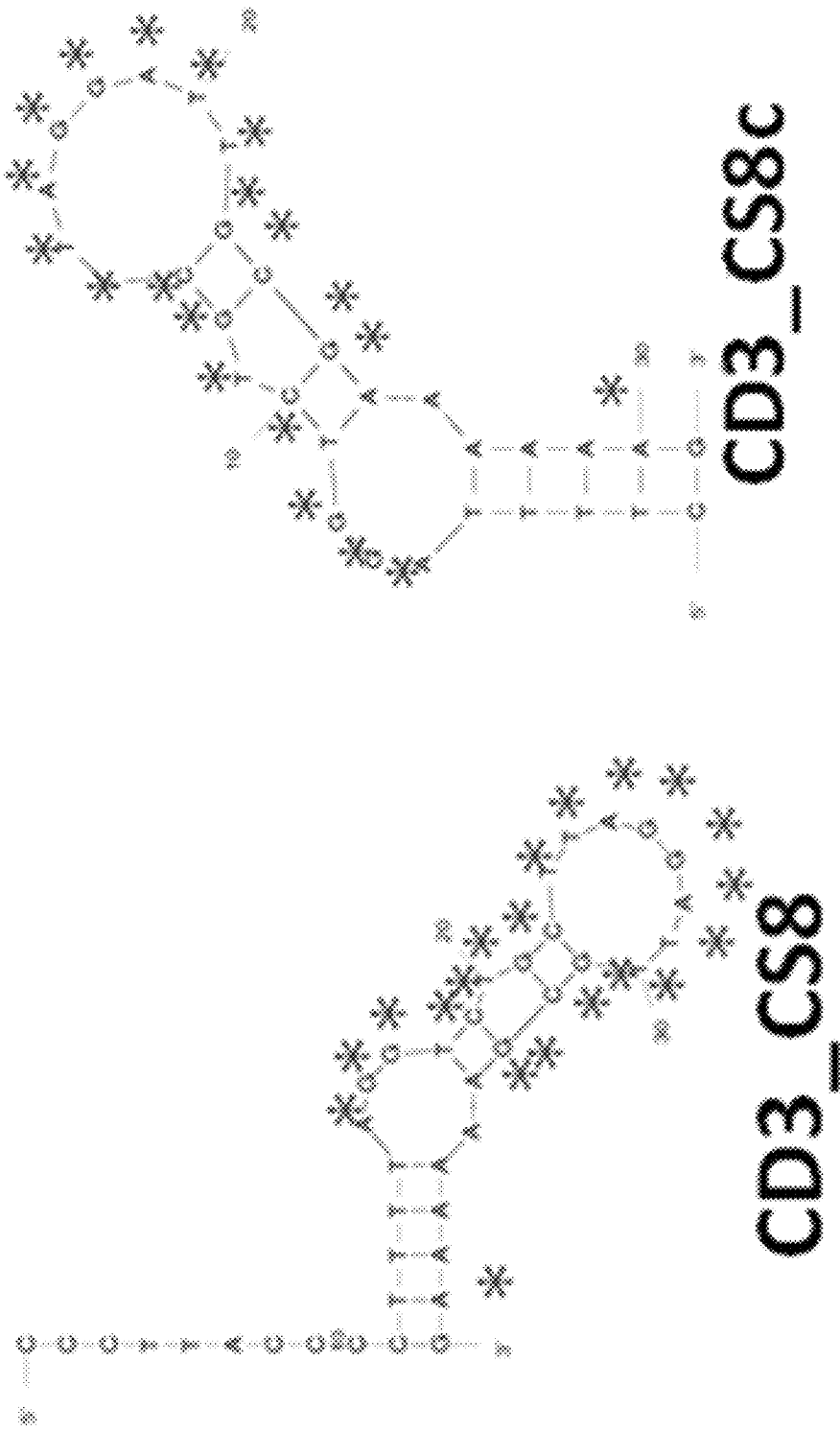
Figure 3C:
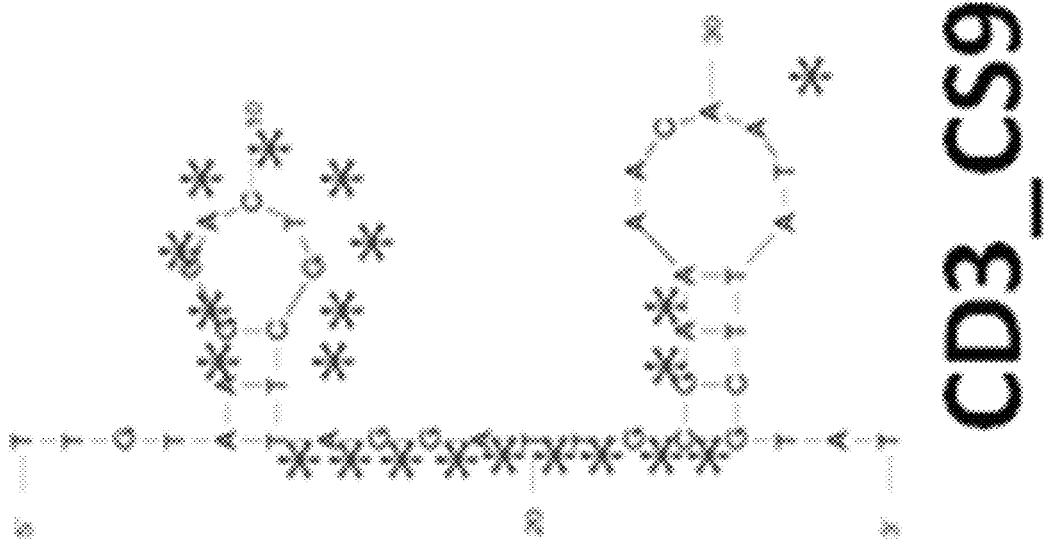

Next, the 14 aptamers with high mean P-positive values (P-positive >0.5) (see Table 8) underwent multiple sequence alignment and a shared motif was found (FIG. 3B upper). In comparison, the highlighted candidates (CS6-9) were also aligned and a more robust motif was discovered (FIG. 3B bottom). In addition, structure prediction analysis was carried by analytic software (mfold, NUPACK) (FIG. 3C). This analysis demonstrated that candidates fold into a complex secondary structure mainly around the motif region. Following this result and in an optimization attempt, CD3_CS8 was further edited by trimming the first 9 nucleotides (denoted CD3_CS8cut) which seemed irrelevant to the formation of the secondary structure around the presented motif in CS_CD8. Top 5 candidates were further confirmed to possess a negative Delta G scores and were selected for individual binding assays.

In addition to the binding SELEX described above, a hybrid methodology was implemented, in which the process included also whole-cell SELEX rounds

TABLE 9

Alternative CD3-binding aptamers

| Aptamer name | SEQ ID NO: | Sequence 5' to 3' |
|---|---|---|
| CS1 | 15 | CTCTACCTGACTGTAACCTCTCGCTCC CCCCCATTCGCGC |
| CS2 | 16 | TTGTCCCTCTACGCCGCCCTTTACTAC CACTCCTGCGATT |
| CS3 | 17 | TCCAGCACACCGACCGCCCCTCTACAT TACCCCCTGGACT |
| CS4 | 18 | CCCCTCCATTCCCCCGCCTCGTCCACC CTACTCCTTAGTC |
| CS5 | 19 | CATCGACGCCCACACACCACTTCCCGT TCCCCTGCATCAT |

Figure 4:
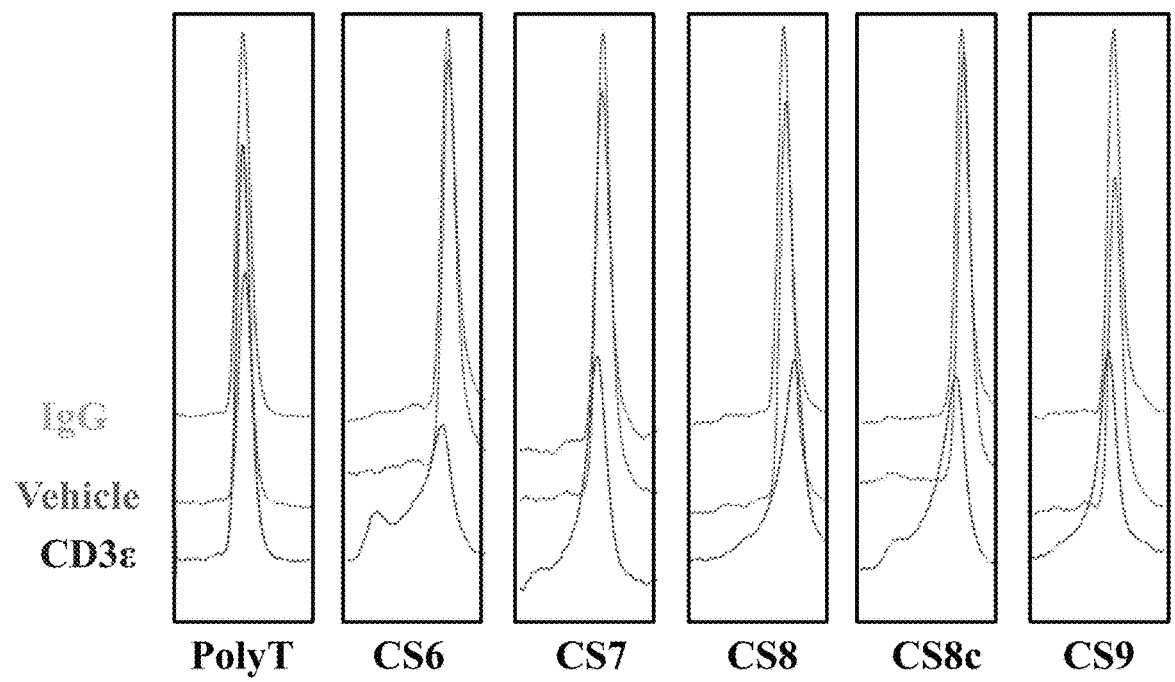
FIG. 4 shows aptamer sequences binding to target protein by HPLC. Folded and Cy5-labelled aptamer candidates were assayed for recombinant Human CD38 (hCD38) binding. Aptamers were incubated for 1 hr at 37° C. with hCD3e or with the negative control IgG1. PolyT were used as a negative control sequence
Figure 5A:
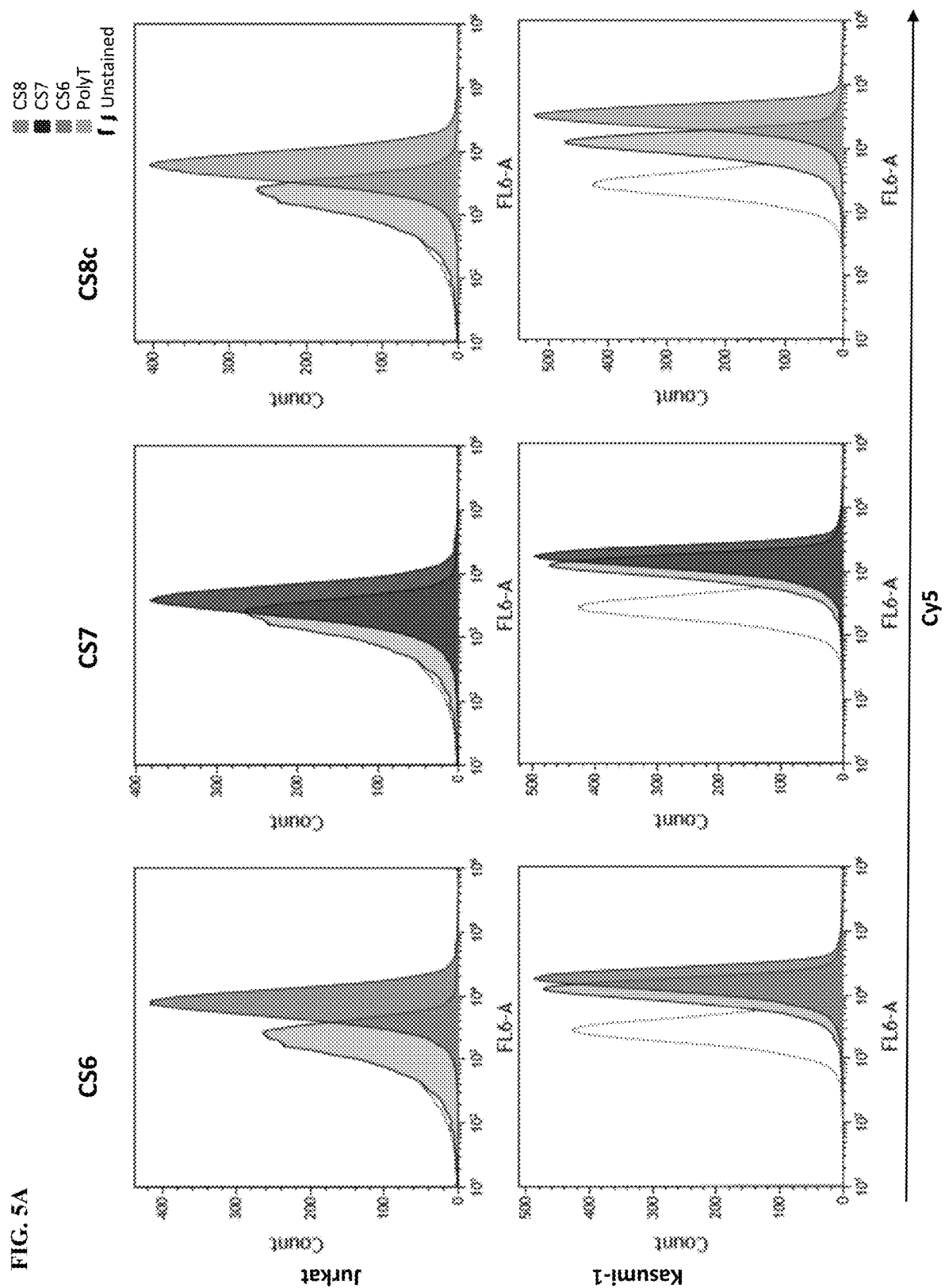
FIGS. 5A-5C show CS6 binding to T cells as demonstrated via flow cytometry. Jurkat cells and Kasumi-1 cells were incubate with CpG'-Cy5 labelled CS6, CS7 and CS8c, and analyzed by flow cytometry.
Figure 5A:
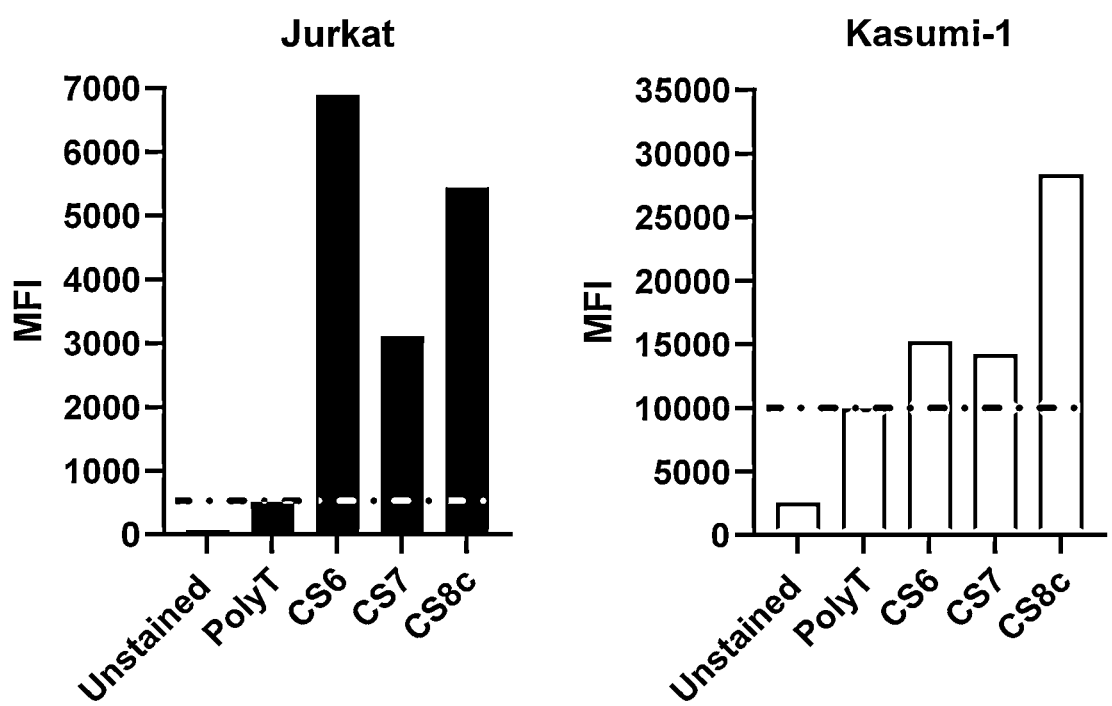

Example 3-Individual CD3 Binding Aptamers Validation a. Aptamer Candidates Demonstrate Binding to Human CD38 Via HPLC Top five candidates (CS6, CS7, CS8, CS8c, and CS9 SEQ ID NO. 1-5) were synthesized with a 5(5') phosphothioated CpG motif and assayed for Human CD38 (hCD38) binding via the HPLC size exclusion column. In this method, the aptamers were labelled with Cy5 complementary sequence to the CpG site (Cy5-CpG'). Then, the folded-labelled candidates are incubated, each, with the CD38-recombinant protein or with negative control IgG1 (1 hr at 37° C. and 4° C.) and analyzed by HPLC ProSEC 300S size exclusion column (Agilent) at 570 nm absorption. Upon protein binding, the aptamer-protein complex has a greater mass than a free aptamer and as a result, the retention time (RT) at the column is expected to be shorter. Inversely, in the case of non-binding aptamer, the RT in the presence of protein will be the same as in the absence of the protein. As a control, PolyT sequence was used. All five candidates demonstrated a binding to CD3 epsilon target protein at varying levels (FIG. 4)

b. Aptamer Candidates Demonstrate Specific Binding to Jurkat T Cell Line and Primary Human Pan T Cell by Flow Cytometry After CS6, CS7 and CS8c candidates demonstrated specific binding to CD3e recombinant protein, they were assayed for binding to their target in the native, whole-cell context, on the surface of T cells by flow cytometry. For this purpose, Jurkat T lymphocyte cell line (Acute T cell leukemia, ATCC TIB-152), previously reported to exhibit TCR expression, were used. The first binding assay with cells conducted at 4° C. for 1 hr. As a negative control, the myeloblast Kasumi-1 cell line was used (Acute myeloblastic leukemia, ATCC CRL-2724) All three candidates were found to differentially bind the target cells as compared with control cells while CS6 and CS7 demonstrated better specificity than CS8c. (FIG. 5A)

Figure 5B:
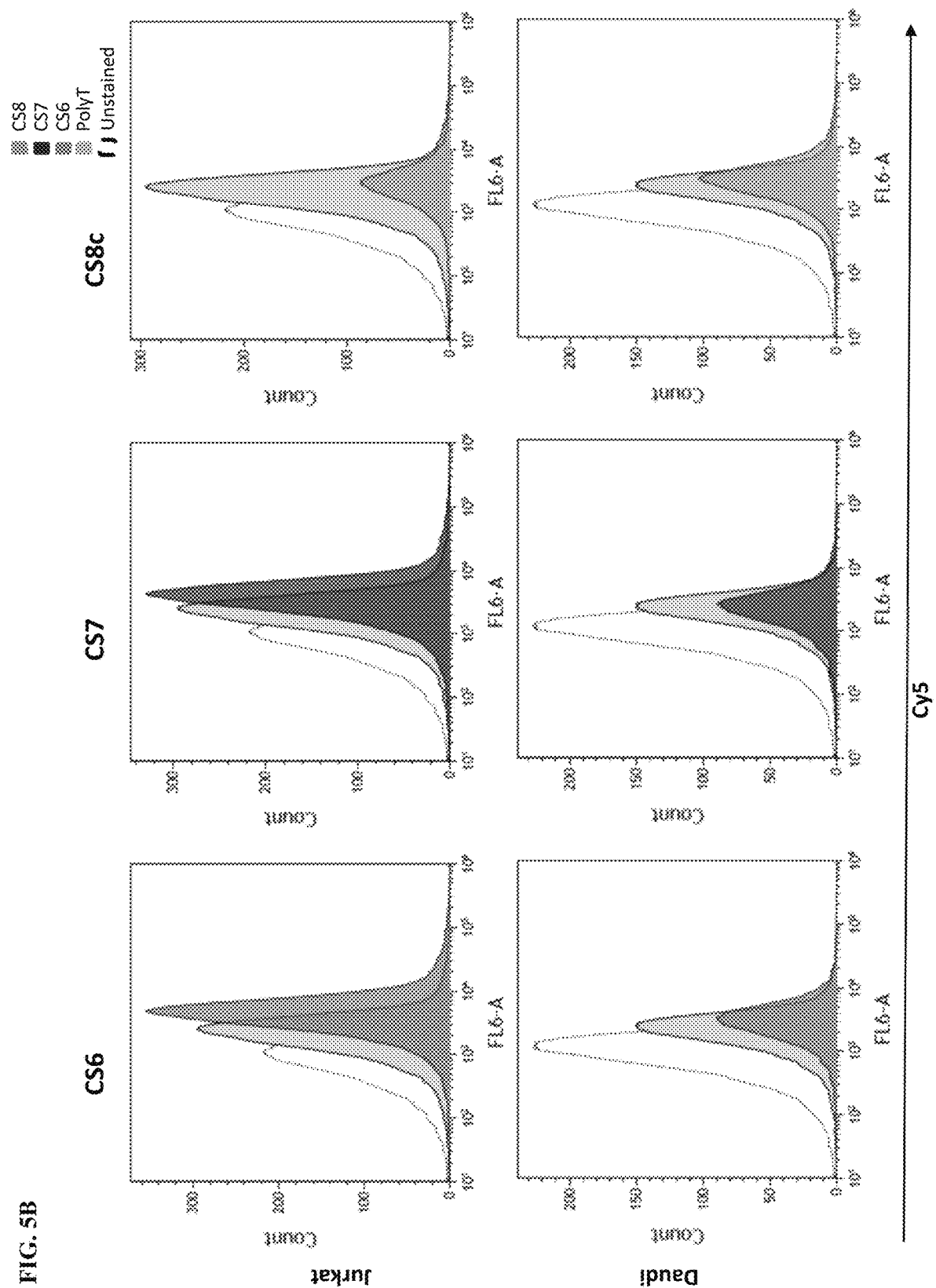
Figure 5B:
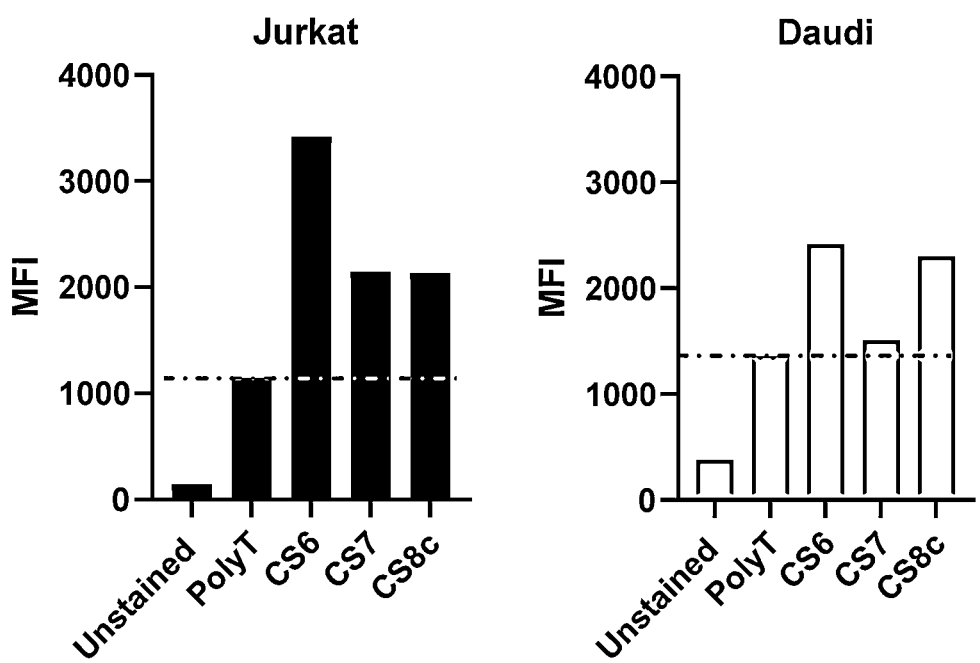

Next, to better mimic physiological conditions, the three candidates were assayed for binding Jurkat at 37° C. Here, as a negative control, B lymphoblast Daudi cell line was used (lymphoblast, ATCC CCL-213) (FIG. 5B). In this experiment, the three candidates bound the target cells when CS6 showed the highest binding level.

Figure 5C:
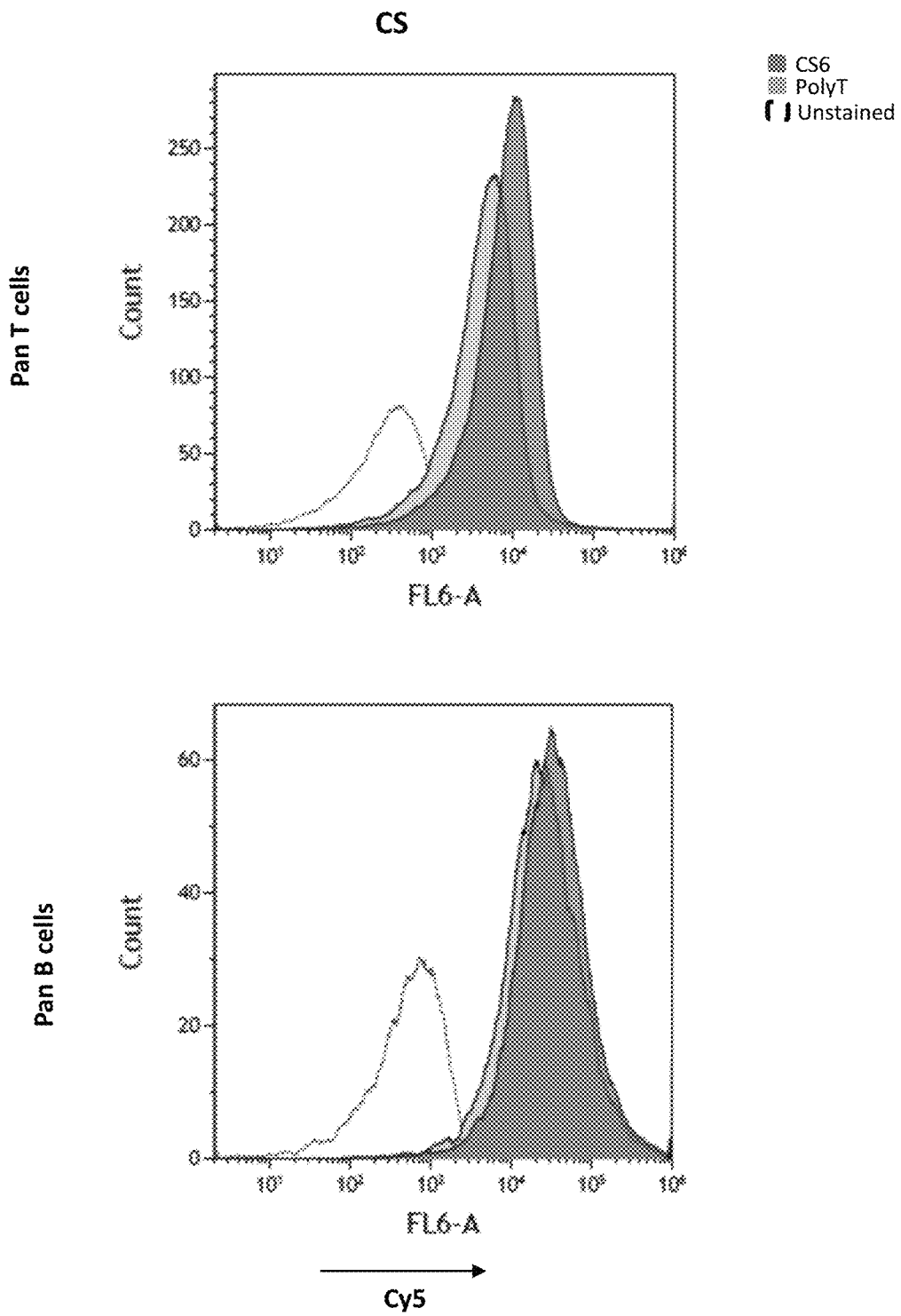
Figure 5C:
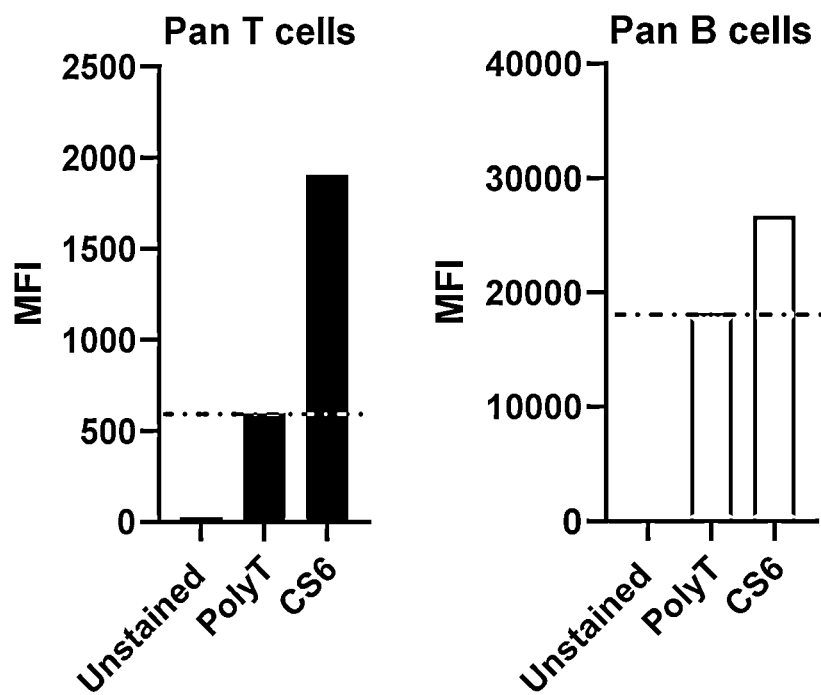
Figure 5C:
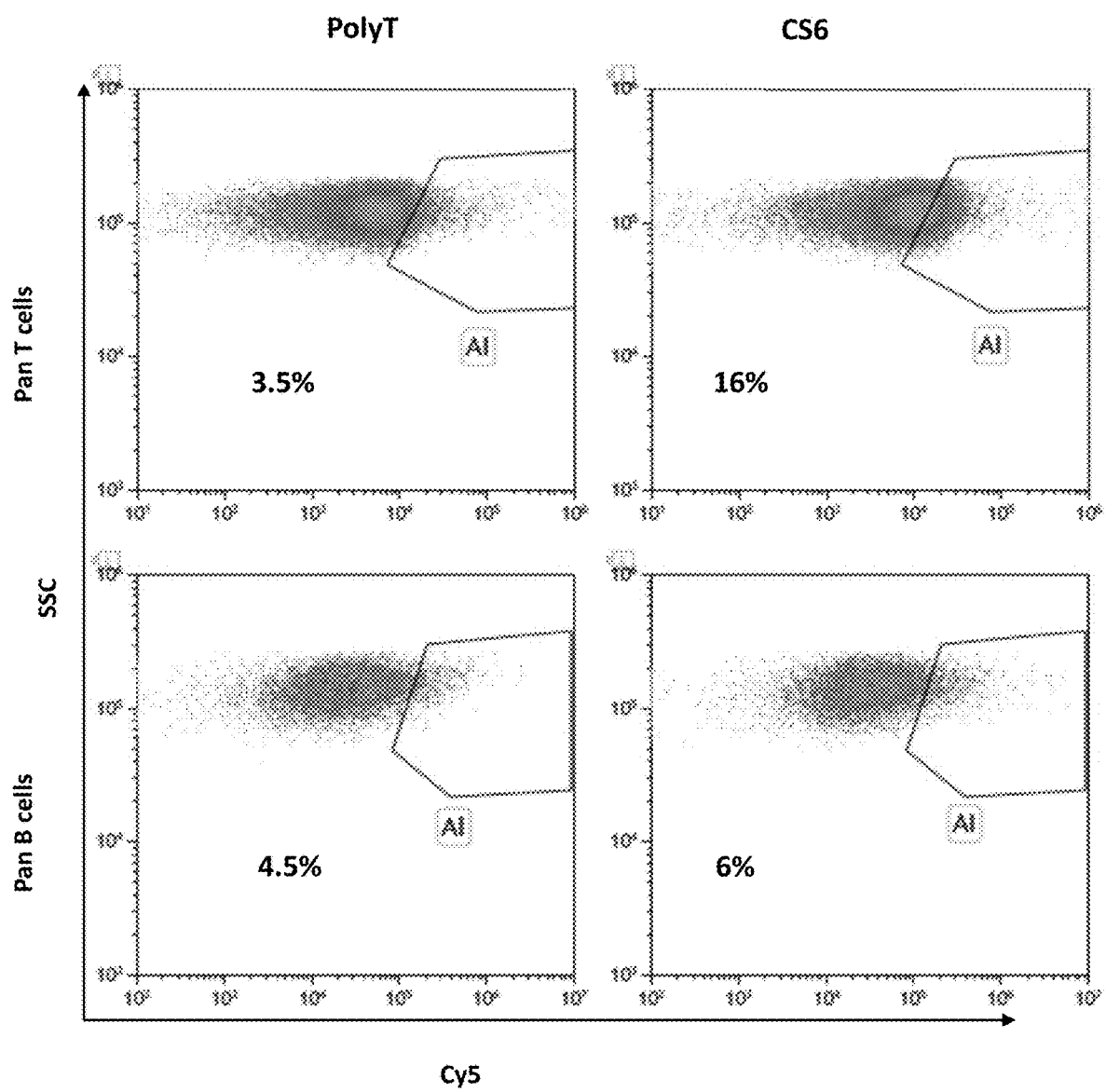

CS6 was selected for further exploring and characterization. It was found to bind normal primary Pan T cells and not Pan B cells at 37° C. under blocking conditions (FIG. 5C)

Figure 6:
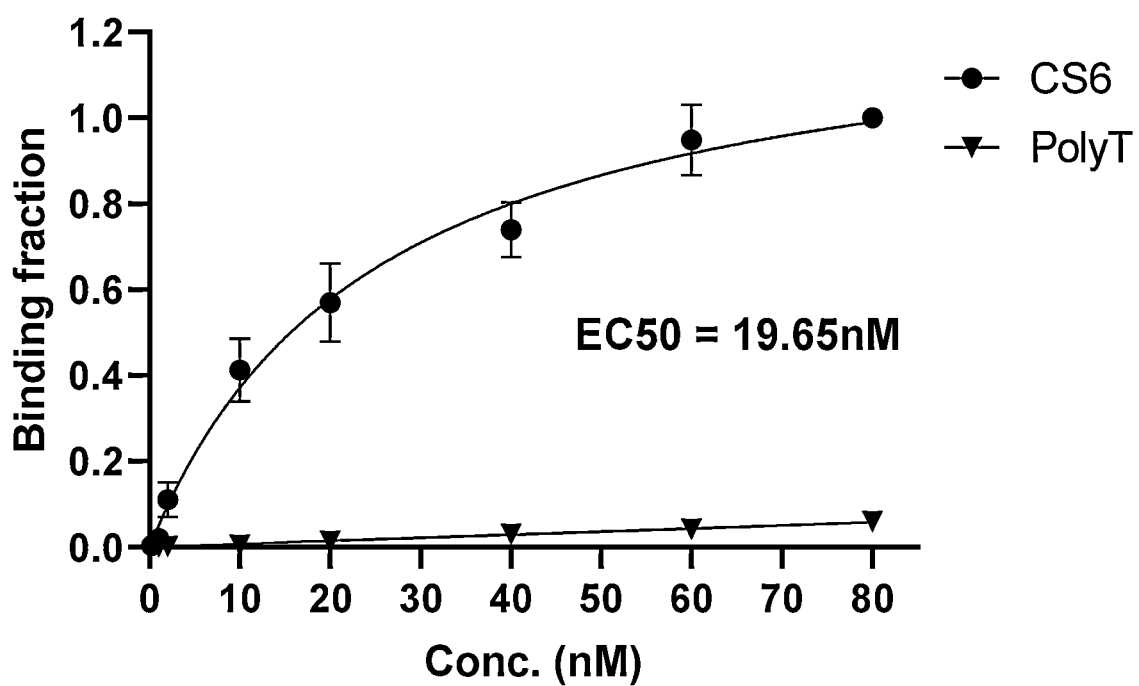
FIG. 6 show CS6 effective concentration. Jurkat cells were incubated with serially-diluted concentrations of CpG'-Cy5 labelled CS6 and analyzed by flow cytometry to determine compound's $EC_{50}$.

Subsequently CS6 effective concentration 50 ($EC_{50}$) was evaluated. A serial dilution of -Cy5 labelled aptamer was incubated with Jurkat cells for 1 hr at 37° C. and assessed for binding via flow cytometry (FIG. 6). The calculated $EC_{50}$ value was 19.65 nM.

Example 4-Material and Methods for Example 5

A. Materials a. Animals

Female NSG mice, 7-8 weeks' old were purchased from Jackson Labs b. Cell Lines and Peripheral Mononuclear Cells (PBMCs)

HCT-116 human colorectal cell line (ATCC® CCL-247TM) were cultured according to ATCC instructions.

PBMCs were isolated by Ficoll density gradient centrifugation from peripheral blood from healthy donors using Lymphoprep™ (Axis-Shield) following the manufacturer's protocol. Isolated PBMCs were frozen in medium of FBS+ 20% DMSO. Cell viability test and immunophenotyping of lymphocytes subpopulations (DuraClone) and activation markers were conducted post isolation and upon thawing, at injection day c. Aptamers Cancer-targeting aptamer arm, Variable Strand 12 (VS12, SEQ ID NO: 22) was derived from a functional enrichment process as described in PCT Application No. PCT/IB19/ 01082 using HCT-116 colon carcinoma cell line as target cells. CS6 T cell engager sequence (SEQ ID NO: 21) was derived from SELEX binding process as described in Examples 2-3. Aptamers were synthesized as one oligonucleotide chain and were column purified. Complementary CpG-motif sequences were added to both cancer-targeting and immune engager aptamers to allow hybridization and the generation of bispecific aptamer conjugate.

The non-specific Poly T oligonucleotide was used as a control. Two Poly T strands were also hybridized to form a duplex but in this case, the hybridization domain is not a functional one. Full length sequences are founds in Table 10.

TABLE 10

T cell engager and tumor-targeting sequences, with chemical modifications and CpG hybridization motives to generate aptamer conjugates

| Aptamer name | SEQ ID NO: | Sequence 5' to 3' |
|---|---|---|
| 5PS-CpG\|CS6 | 20 | T*C*G*T*C*GTCGCGGTTCGCGTCC GTATCGTATAAGGGCTGCTTAGGATT GCGATAATACGGTCAA |
| 5PS-CpG\|CS6\|invdT | 21 | T*C*G*T*C*GTCGCGGTTCGCGTCC GTATCGTATAAGGGCTGCTTAGGATT GCGATAATACGGTCAA/invdT |
| 5PS-CpG'\|HCT116-VS12\|invdT | 22 | C*G*G*A*C*GCGAACCGCGACGACG ATGATTGATCTATTTTCCATATCGCG TTGAGTGTAAAGCCACGAAGGGTTA T/invdT | c. Formulation Buffer/Vehicle
Phosphate-buffered saline (minus Magnesium and Calcium) supplemented with 1 mM Magnesium Chloride ($MgCl_2$). The folding buffer is sterilized by filtration and used immediately.
B. Experimental Methods
a. Bispecific Personalized Aptamer Formulation
Formulation procedure includes the following steps:
1. Reconstitution
Each strand is diluted/reconstituted (if lyophilized) to the desired concentration in the formulation buffer.
2. Aptamer Folding:
  a. Strands are heated for 5 minutes at 95° C.
  b. Rapid cooling for 10 minutes on ice.
  c. Incubation for 10 minutes at RT.
3. Bispecific Entity Formation
b. The Two Strands (Cancer-Targeting Variable Strand and the Immune Engager Strand) are then Mixed Together and Incubated in a Rotator for 30 Minutes at RT. Xenograft Model Induction and Interventions
Female NSG mice were injected subcutaneous (SC) into the mouse right flank with $2\times10^6$ HCT-116 tumor cells admixed with $0.5\times10^6$ thawed human PBMC in a 1:4 ratio with Cultrex®. At day 7, IV re-boost of PBMCs of the same donor was performed and $8\times10^5$ cells were injected to each mouse.
Regimen of SC interventions is detailed in Table 11.

TABLE 11 in vivo treatment schedule

| Group | Intervention | RoA | Number of interventions | Days of treatment |
|---|---|---|---|---|
| 1 | Vehicle | SC | 10 | 0, 1, 2, 3, 4, 6, 7, 8, 9, 10 |
| 2 | CS6-VS12 | SC | 10 | 0, 1, 2, 3, 4, 6, 7, 8, 9, 10 |
| 3 | Poly T-Poly T | SC | 10 | 0, 1, 2, 3, 4, 6, 7, 8, 9, 10 | a. Tumor Volume Method of Evaluation
Change in tumor volume was monitored by calipers three times per week. Tumor volume was estimated as follows: Tumor Volume (mm3)=(length×width$^2$)/2
b. Statistical Methods
All quantitative data are expressed as the mean±SEM. Either ANOVA or Student t-test were used, when appropriate, in order to evaluate significance of difference between groups.

Example 5-Proof-of-Concept (POC) for Novel Bispecific T Cell Engager Efficacy

Figure 7:
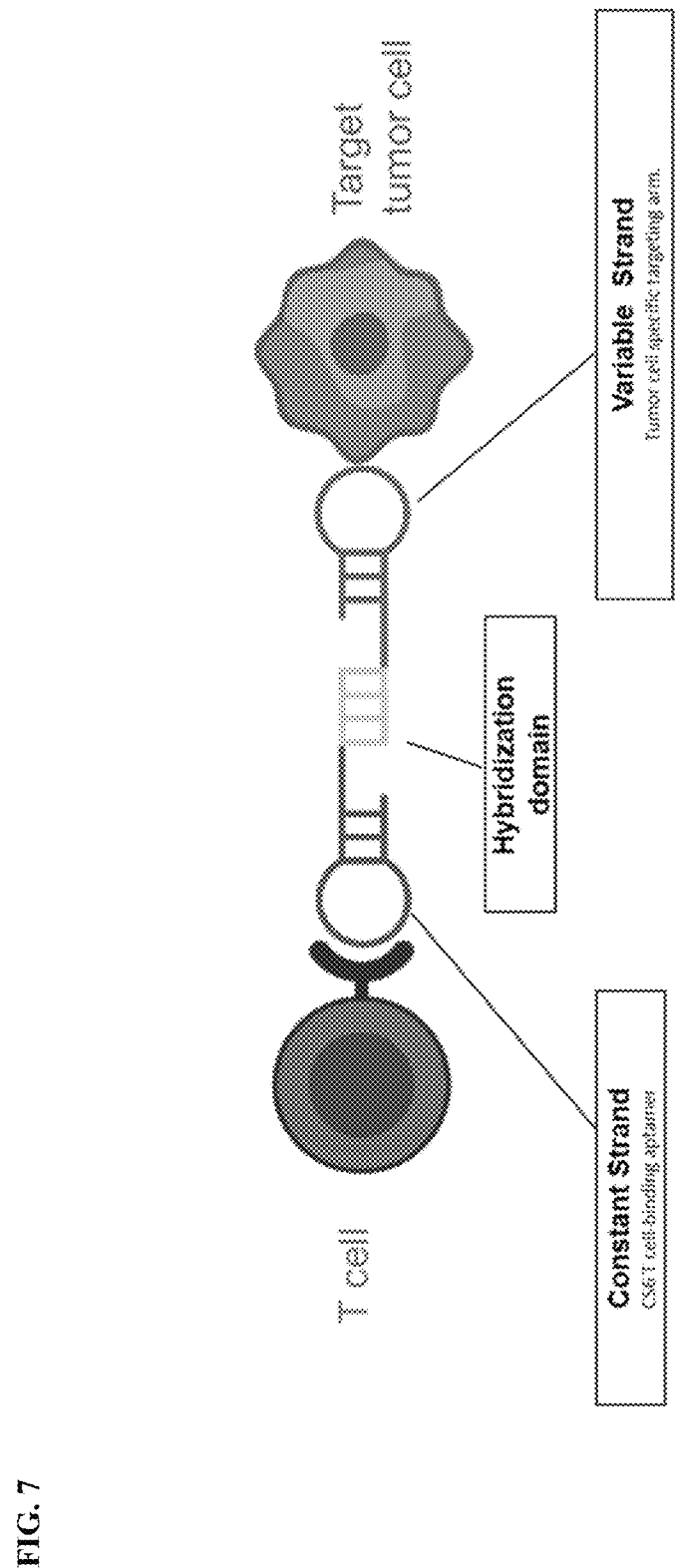
FIG. 7 provides a schematic representation of an exemplary use of T cell engager aptamer as an aptamer conjugate. In this example, the T cell-binding aptamer is linked to a cancer-targeting, second aptamer, to yield a bispecific aptamer entity. Depicted are the three different domains of the therapeutic agent.
Figure 8A:
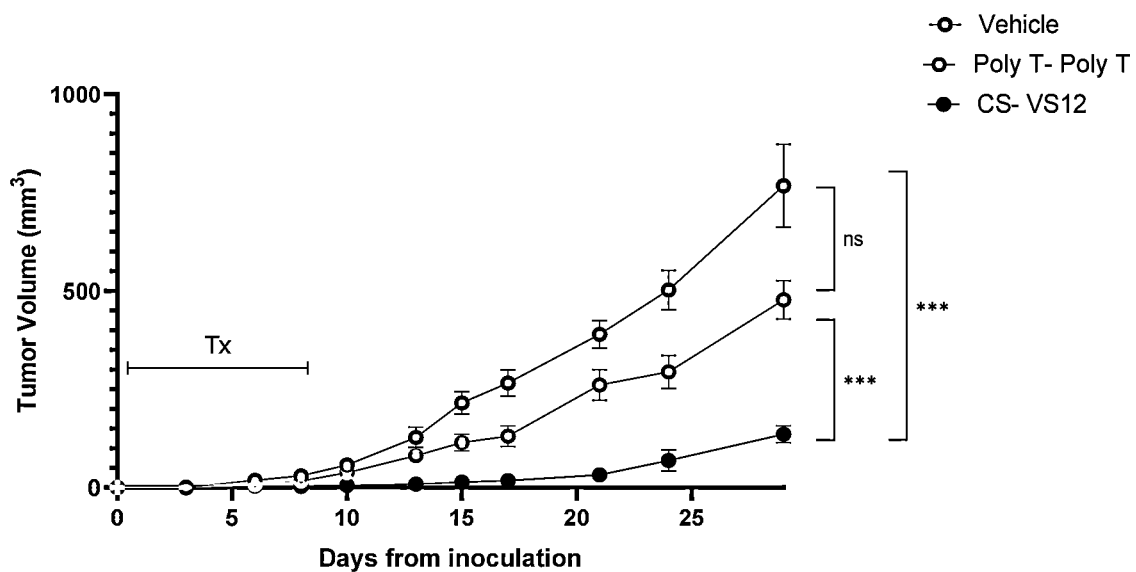
FIGS. 8A and B show in vivo efficacy of the exemplary bispecific T cell engager aptamer, comprised of CS6 aptamer (SEQ ID NO 21) hybridized to HCT116, colon carcinoma cell line-targeting aptamer sequence (named VS12. SEQ ID NO 22). Female NSG mice were implanted SC with HCT-116 tumor cells admixed with human PBMC followed by a treatment with T cell engager bispecific personalized aptamers for a total of 10 doses administered SC. HCT116 tumor volume was monitored for CS6-VS12 treatment, PolyT-PolyT (non-specific DNA aptamer) and Vehicle mice groups (A). Individual mice growth curves are depicted in FIG. 8B. *** indicates significant difference (($p \leq 0.001$).

1. Representative Structures of Bispecific Conjugate Aptamers
In some aspects, personalized cancer therapeutics described herein are composed of a heterodimeric structure with three separate domains (FIG. 7).
In some embodiments, bispecific personalized, conjugated aptamers are designed to target specific neoantigens and surface molecules displayed by cancer cells of patients and to facilitate both direct lethality of cancer cells as well as immune-associated responses. In some embodiments, efficacy is achieved through three separate modes-of-actions (MoAs) incorporated into a single therapeutic entity, as described below:
A. Variable Strand: Direct Killing of Cancer Cells by Personalized Aptamer
In some embodiments, this moiety is selected through a process initiating from a random pool of $10^{15}$ potential leads and is described in detail in the PCT Application No. PCT/IB19/01082. Briefly, the personalized process is designed to identify aptamers that best facilitate targeted killing of cancer cells while not harming healthy cells. The patient-specific strand is identified by conducting Binding and Functional Enrichment Processes (Cell and Functional SELEX), screening candidates with high-throughput microscopy, and confirming the activity and specificity of top candidates, while including selectivity tests and attempting to rule out off-target effects.
B. Constant Strand: A T Cell Engager Aptamer
In some embodiments, this aptamer arm is T cell-targeting and designed to mediate target cancer cell lysis through engaging immune cells
C. CpG Motif with TLR9-Agonistic Activity
The two aptamer arms of the bispecific structure are bridged together by nucleic-base hybridization of single stranded overhangs of complementary sequences. This hybridization domain is CpG rich and designed to induce TLR9-mediated antigen presenting cell (APCs) stimulation and increased uptake of tumor antigens. Stimulated APCs would subsequently migrate to the tumor draining lymph nodes and cross-present the engulfed tumor antigens to cytotoxic T lymphocytes, resulting in an adaptive, systemic, anti-tumor immune response.
2. In Vivo POC of CD3-Targeting Bispecific Aptamer Conjugate in HCT116 Tumor Xenograft Model
HCT-116 cells and human PBMCs mix (E:T 1:4 ratio) were co-injected in an admix manner followed by administration of Bispecific personalized aptamer (CS6-VS12, SEQ ID NO. 21 and 22), Poly T duplex or Vehicle.
FIG. 8A describes HCT116 tumor growth kinetics. Treatment with the Bispecific aptamer CS6-VS12, but not with the non-specific oligonucleotide PolyT, significantly attenuated the growth of HCT116 tumors after a total of 10 interventions. As of day 30, mice began to be scarified due to ethical volume for endpoint.).

Figure 8B:
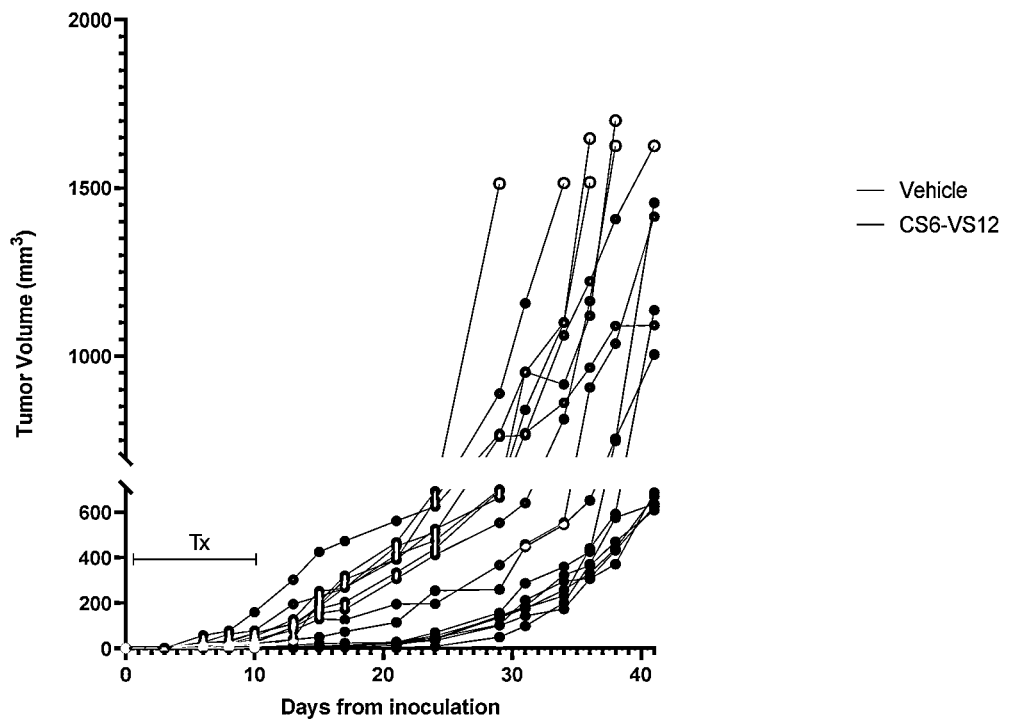

Individual mice tumor volume are presented until Day 41 (31 days after last intervention). Inhibition in tumor growth was demonstrated in all CS6-VS12 treated mice (FIG. 8B).

Figure 9:
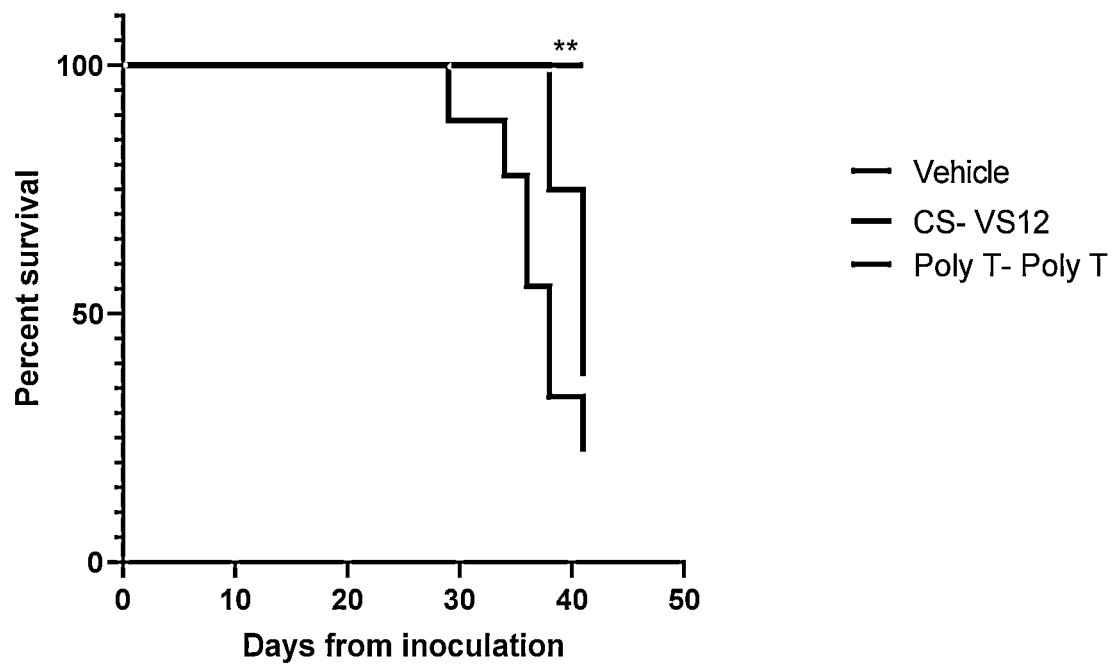
FIG. 9 depicts Kaplan-Meier survival analysis of treated Mice. ** indicates significant difference (($p \leq 0.01$).

Tumor growth reduction was translated to a benefit in survival for the bispecific-treated group, as compared to Vehicle FIG. 9 shows that till Day 41 of the experiment 8 out of 8 mice of the CS6-VS12 group survived, compared to 2 out of 9 mice (22.2%) and 3 out of 8 mice (37.5%) of the vehicle and poly T groups, respectively.

Taken together, the in vivo results from this model indicate the efficacy and potency of CS6-VS12 treatment.

Example 6-Bispecific Personalized Aptamers

F. Representative Structures of Bispecific Personalized Aptamers

In some aspects, personalized cancer therapeutics described herein are composed of a heterodimeric structure with three separate domains (FIG. 7).

In certain aspects, the platform described herein is designed to yield patient-tailored cancer therapeutics to treat patients with individualized solutions optimized for the unique set of conditions and potential drug targets presented by each patient as reflected by fresh sample tissues of their tumors. In some embodiments, bispecific personalized aptamers are designed to target specific neoantigens and surface molecules displayed by cancer cells of patients and to facilitate both direct lethality of cancer cells as well as immune-associated responses. In some embodiments, efficacy is achieved through three separate modes-of-actions (MoAs) incorporated into a single therapeutic entity, as described below:

1. Personalized Strand: Direct Killing of Cancer Cells by Personalized Aptamer

Figure 10:
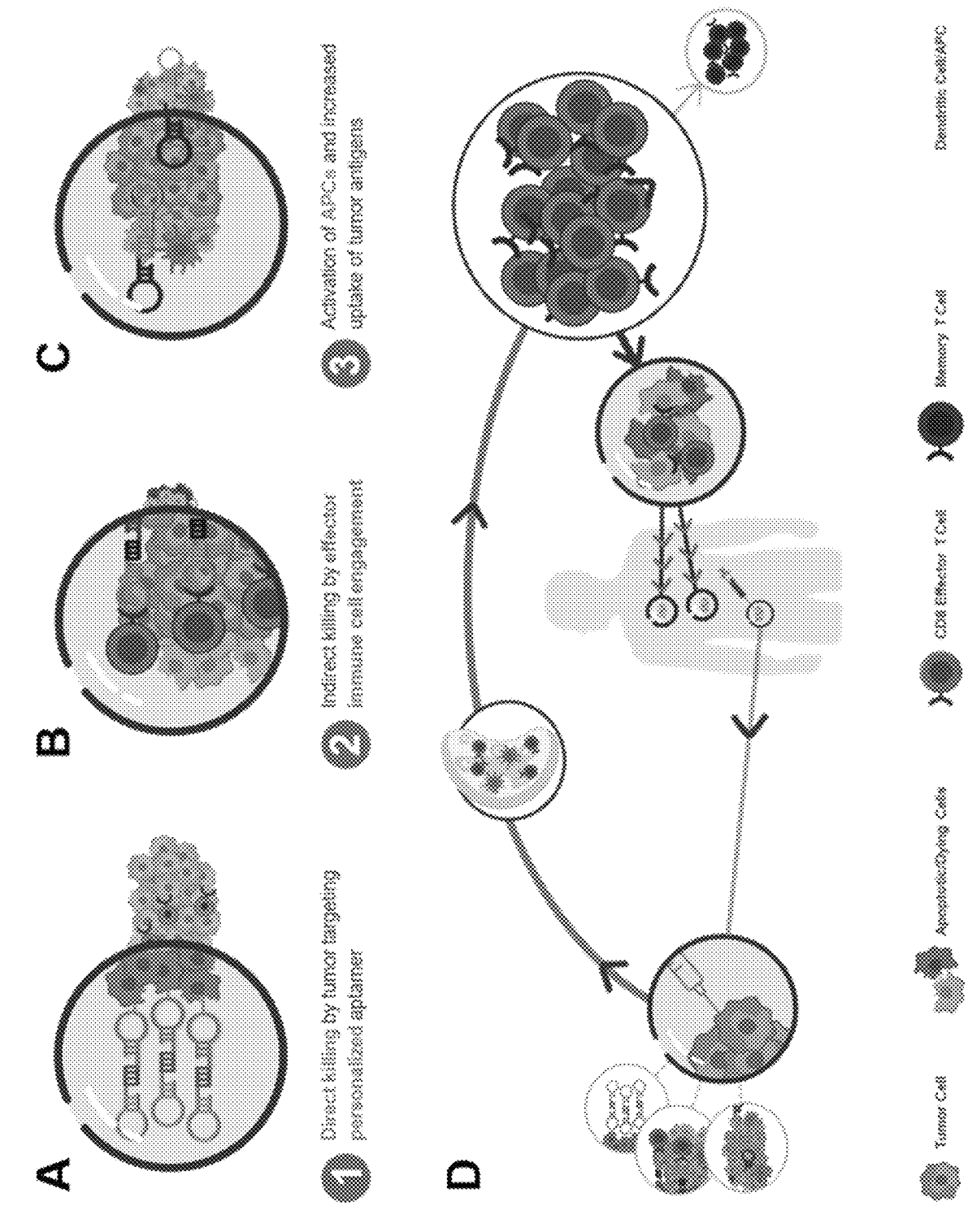
FIG. 10 shows three modes-of-actions (MoAs) in solid tumors for an intratumorally administered bispecific personalized aptamer (panels A-C) and its downstream systemic effect (panel D).

In some embodiments, this moiety is selected through a process initiating from a random pool of $10^{15}$ potential leads and is described in detail in the PCT Application No. PCT/IB19/01082. Briefly, the personalized process is designed to identify aptamers that best facilitate targeted killing of cancer cells while not harming healthy cells. The patient-specific strand is identified by conducting Binding and Functional Enrichment Processes (Cell and Functional SELEX), screening candidates with high-throughput microscopy, and confirming the activity and specificity of top candidates, while including selectivity tests and attempting to rule out off-target effects. (FIG. 10A).

2. Immune-Modulating Strand: Cancer Cell Lysis Through T or NK Cell-Mediated Cytotoxicity In some embodiments, this aptamer arm is a CD3 binding aptamer disclosed herein (e.g., comprising a sequence of any one of SEQ ID NO. 1-21) (FIG. 10B). This immune-modulating arm could potentially be designed to be shared across different patients.

3. CpG Motif with TLR9-Agonistic Activity

In some embodiments, the two aptamer arms of the bispecific structure are bridged together by nucleic-base hybridization of single stranded overhangs of complementary sequences. This hybridization domain is CpG rich and designed to induce TLR9-mediated antigen presenting cell (APCs) stimulation and increased uptake of tumor antigens (FIG. 10C). Stimulated APCs would subsequently migrate to the tumor draining lymph nodes and cross-present the engulfed tumor antigens to cytotoxic T lymphocytes, resulting in an adaptive, systemic, anti-tumor immune response (FIG. 10D).

G. Personalized Process for Each Patient

Figure 11:
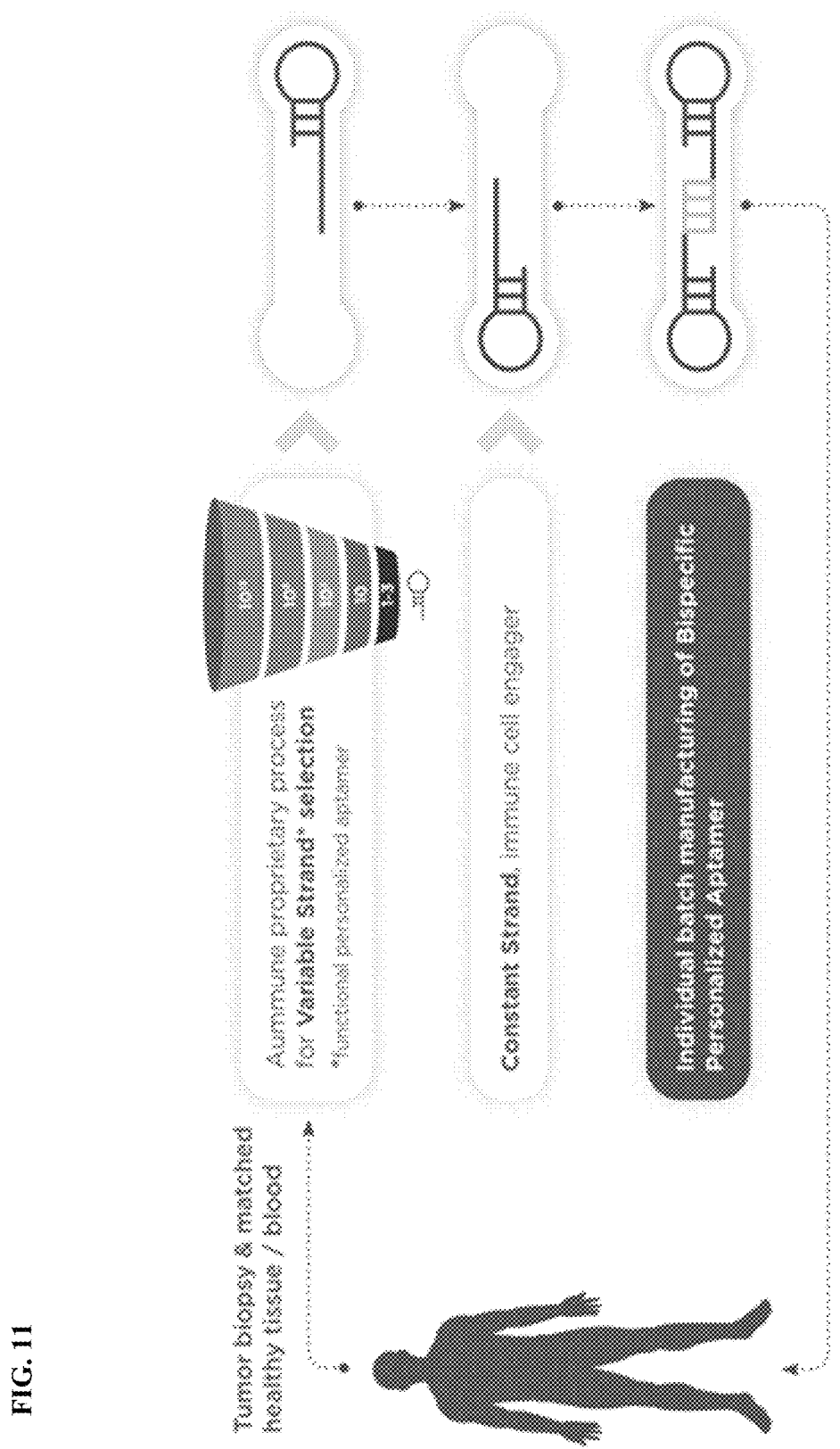
FIG. 11 shows critical steps in the personalized process for each patient.

In some embodiments, as a cancer therapeutic platform, the personalized process contains several critical steps (FIG. 11):

1. Receipt of two types of primary matched samples from the subject
   a. Tumor biopsy
   b. Healthy tissue to be used as a negative control which will consist of either normal tissue from the site of biopsy or Peripheral Blood Mononuclear Cells (PBMCs).
2. Implementation of the selection process described herein to identify a personalized aptamer which induces tumor cell death while leaving healthy cell intact;
3. Manufacturing and hybridization of both strands to yield bispecific personalized aptamers;
4. Bispecific personalized aptamer is administered to the respective individual subject.

Example 7-In Vivo Efficacy of Bispecific Aptamers

Figure 12:
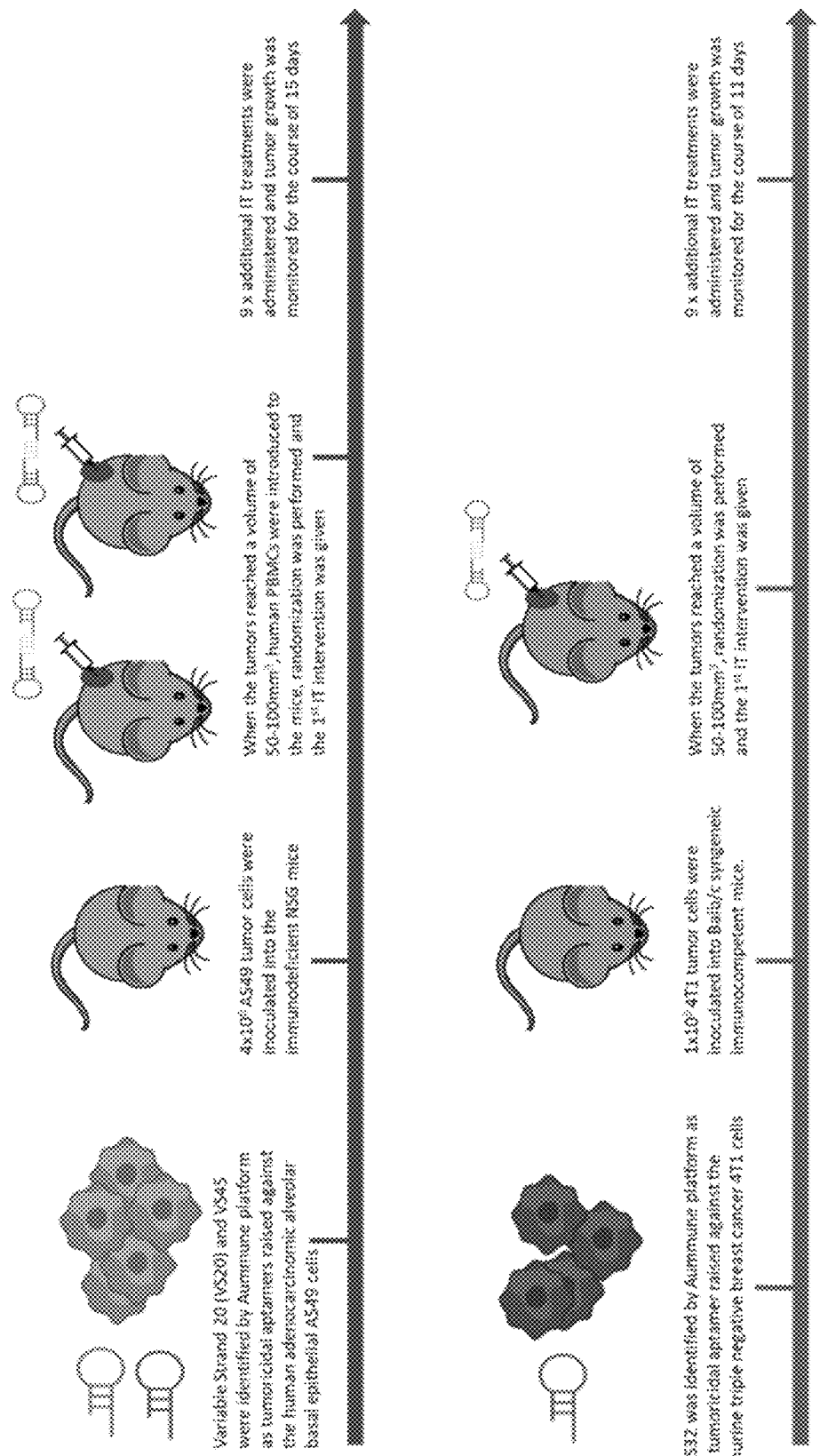
FIG. 12 is a schematic illustration of a study design for identifying customized Variable Strands and testing bispecific aptamers on two established tumor mouse models.

Intratumoral administration of bispecific aptamers was tested. Two tumor cell lines were used to identify tumor-specific aptamers to serve as Variable Strands using the apatamer identification process disclosed herein. Specifically, tumorocidal aptamers VS20 and VS45 were identified using human alveolar adenocarcinoma A549 cells and tumorocidal aptamer VS32 was identified using murine triple negative breast cancer 4T1 cells. Subsequently, the CS6 CD3e targeting aptamer was hybridized to each of the tumorocidal aptamers. The sequences of each of these aptamers is provided in Table 12. Each of the three bispecific compounds were tested for functionality in vivo using the process illustrated in FIG. 12.

TABLE 12

Exemplary aptamer sequences

| Aptamer | SEQ ID NO. | Sequence |
|---|---|---|
| 5PS-CpG' \| A549-VS20 \| invdT | 56 | C*G*G*A*C*GCGAACCGCGACGACGATAG CAATCATATGGCTGTGCTCATTTAATAAGC AAGCTGGG/invdT |
| 5PS-CpG' \| A549-VS45 \| invdT | 57 | C*G*G*A*C*GCGAACCGCGACGACGATGT GTTAGTGATGCGAGCTCCTTACCATTAGAT AGAGGCTG/InvdT/ |
| 5PS-CpG' \| 4T1-VS32 \| invdT | 58 | C*G*G*A*C*GCGAACCGCGACGACGATAA ACTCTATCGTCCAGAGAGAATGTCTGCCTA CTGATTTG/invdT |
| 5PS-CpG \| CS6 \| invdT | 21 | T*C*G*T*C*GTCGCGGTTCGCGTCCGTAT CGTATAAGGGCTGCTTAGGATTGCGATAAT ACGGTCAA/invdT |

Figure 13:
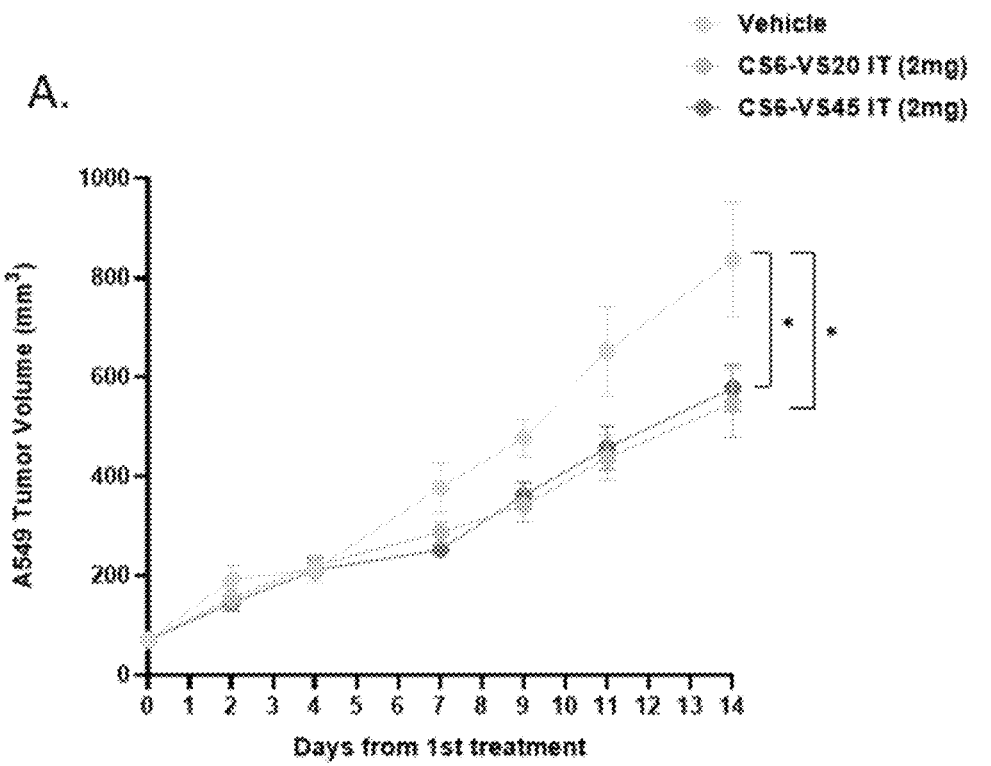
FIG. 13 shows that intratumoral administration of bispecific personalized aptamers significantly attenuates tumor growth. Panel (A) shows A549 tumor volume in mice treated with CS6-VS20, CS6-VS45, and Vehicle for 14 days following administration. Panel (B) shows 4T1 tumor volume in mice treated with CS6-VS32 and Vehicle for 14 days following administration. Two-way ANOVA was implemented for statistical analysis. * Indicates significant difference ($p \leq 0.05$) *** Indicates significant difference ($p \leq 0.001$).
Figure 13:
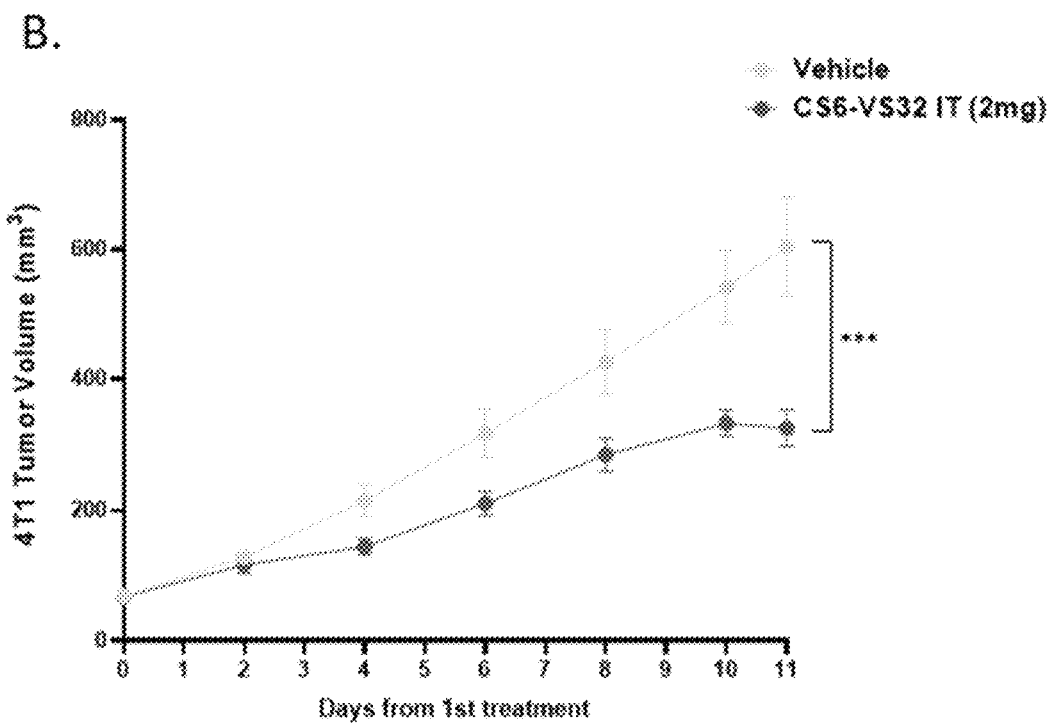

As illustrated in FIG. 13, each of the bispecific entities tested (CS6-VS20, CS6-VS45, and CS6-VS32) effectively led to significant attenuation of corresponding tumor growth in vivo when administered at a 2 mg total dose intratumorally into established tumors (50-100 mm3).

Figure 14:
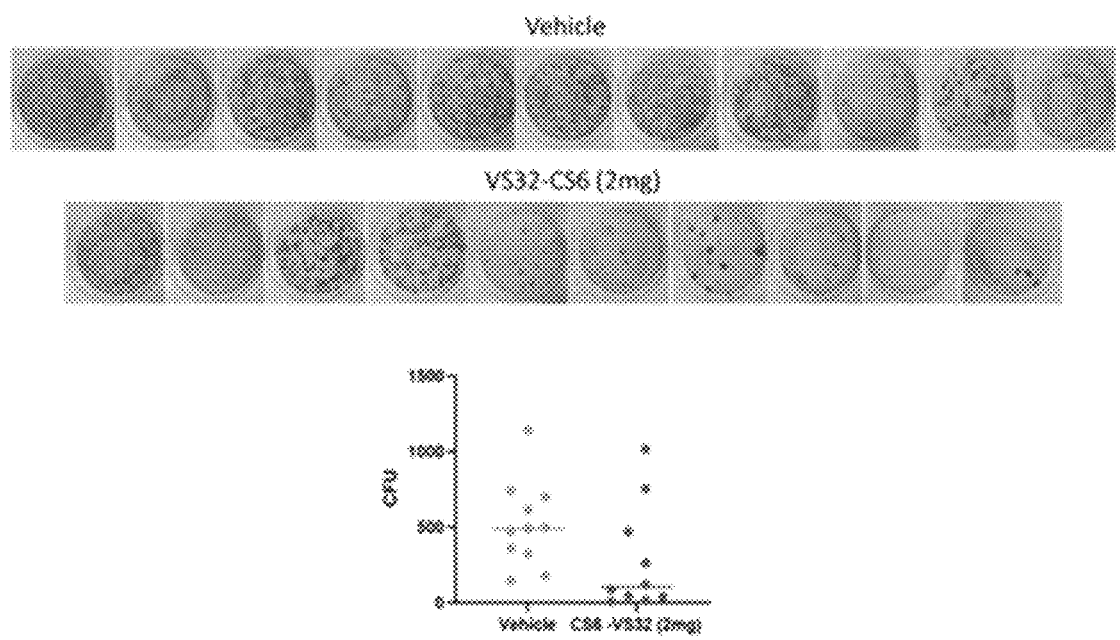
FIG. 14 shows the systemic effect of bispecific personalized aptamer CS6-VS32 administration. In panel (A), lungs were collected at termination of the experiment and cells were plated on 6-thioguanine and colonies were counted after 12-14 days. In panel (B), serum was collected at termination day and was analyzed using mouse IL-6 ELISA assay. Each circle represents a mouse in the tested group (left) spleens were harvested at termination and weighted. Bars represent mean±SEM (right).
Figure 14:
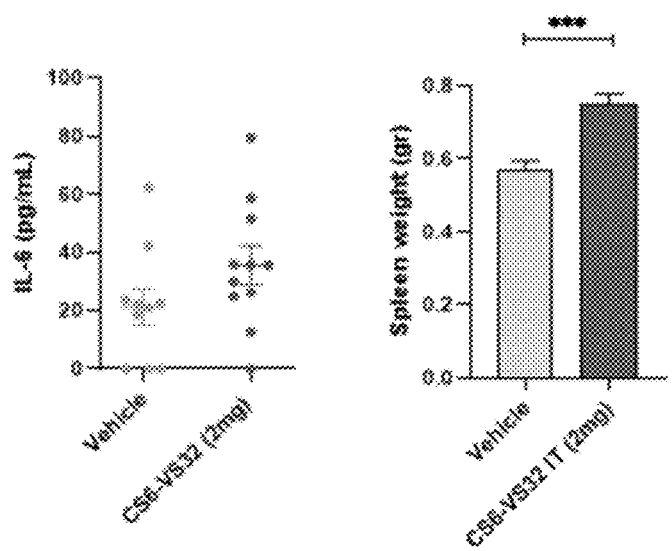

In the 4T1 syngeneic immunocompetent mouse model, intratumoral administration of CS6-VS32 (2 mg) further demonstrated an effect beyond the local growth inhibition of the injected tumor lesion. 4T1 tumors have the capacity to spontaneously metastasize to a variety of organs, including liver and lung. Since 4T1 cells are 6-thioguanine resistant, clonogenic assays were used to measure metastatic foci in the lungs of treated mice. As can be seen in FIG. 14A, reduction of lung metastasis was observed.

In addition, indications for CpG motif/TLR9 activation were assessed and a slight increase in circulating IL-6 and in spleen weights were reported as well for the treated mice group (FIG. 14B).

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An aptamer comprising the nucleic acid sequence of SEQ ID NO: 1, SEQ ID NO: 2, SEQ ID NO: 3, SEQ ID NO: 20, or SEQ ID NO: 21.

2. The aptamer of claim 1, wherein the aptamer binds to a T cell.

3. The aptamer of claim 1, wherein the aptamer binds to a T cell antigen CD3.

4. The aptamer of claim 1, wherein the aptamer induces in vitro or in vivo:
   (a) T cell-mediated cytotoxicity;
   (b) cell death of a cancer cell through T cell-mediated cytotoxicity;
   (c) cytokine secretion; and/or
   (d) T cell activation.

5. The aptamer of claim 4, wherein the aptamer induces cell death of a cancer cell and the cancer cell is a patient-derived cancer cell.

6. The aptamer of claim 4, wherein the aptamer induces cell death of a cancer cell and the cancer cell is a breast cancer cell or a colorectal carcinoma cell.

7. An aptamer of claim 1, wherein the aptamer comprises a chemical modification.

8. An aptamer conjugate comprising an aptamer of claim 1.

9. The aptamer conjugate of claim 8, wherein the aptamer is directly linked to a second aptamer, or is linked to a second aptamer via a linker.

10. The aptamer conjugate of claim 8, wherein the aptamer is linked to a second aptamer, a small molecule, a polypeptide, a nucleic acid, a protein, or an antibody.

11. A method comprising administering to a subject an aptamer of claim 1.

12. A method comprising administering to a subject an aptamer conjugate of claim 8.

13. The aptamer of claim 1, wherein the aptamer comprises the sequence of SEQ ID NO: 1.

14. The aptamer of claim 1, wherein the aptamer comprises the sequence of SEQ ID NO: 2.

15. The aptamer of claim 1, wherein the aptamer comprises the sequence of SEQ ID NO: 3.

16. The aptamer of claim 1, wherein the aptamer comprises the sequence of SEQ ID NO: 20.

17. The aptamer of claim 1, wherein the aptamer comprises the sequence of SEQ ID NO: 21.

* * * * *